(12) United States Patent
Salahieh et al.

(10) Patent No.: US 10,413,412 B2
(45) Date of Patent: Sep. 17, 2019

(54) METHODS AND APPARATUS FOR ENDOVASCULARLY REPLACING A HEART VALVE

(71) Applicant: BOSTON SCIENTIFIC SCIMED, INC., Maple Grove, MN (US)

(72) Inventors: Amr Salahieh, Saratoga, CA (US); Jean-Pierre Dueri, Los Gatos, CA (US); Hans F. Valencia, Santa Clara, CA (US); Brian D. Brandt, Morgan Hill, CA (US); Dwight P. Morejohn, Davis, CA (US); Claudio Argento, Los Gatos, CA (US); Tom Saul, El Granada, CA (US); Ulrich R. Haug, Campbell, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/927,417

(22) Filed: Mar. 21, 2018

(65) Prior Publication Data

US 2018/0206991 A1    Jul. 26, 2018

Related U.S. Application Data

(63) Continuation of application No. 15/138,863, filed on Apr. 26, 2016, now Pat. No. 9,956,075, which is a
(Continued)

(51) Int. Cl.
*A61F 2/24* (2006.01)
*A61F 2/90* (2013.01)
*A61F 2/95* (2013.01)

(52) U.S. Cl.
CPC .............. *A61F 2/2439* (2013.01); *A61F 2/24* (2013.01); *A61F 2/243* (2013.01); *A61F 2/2409* (2013.01);
(Continued)

(58) Field of Classification Search
CPC ........ A61F 2/24; A61F 2/2439; A61F 2/2409; A61F 2/2412; A61F 2/2418; A61F 2/243;
(Continued)

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| CN | 1338951 A | 3/2002 |
|---|---|---|
| DE | 19532846 A1 | 3/1997 |

(Continued)

OTHER PUBLICATIONS

US 8,062,356 B2, 11/2011, Salahieh et al. (withdrawn)
(Continued)

*Primary Examiner* — Alvin J Stewart
(74) *Attorney, Agent, or Firm* — Seager, Tufte & Wickhem LLP

(57) ABSTRACT

The invention includes methods of and apparatus for endovascularly replacing a heart valve of a patient. One aspect of the invention provides a method including the steps of endovascularly delivering a replacement valve and an expandable anchor to a vicinity of the heart valve in an unexpanded configuration; and applying an external non-hydraulically expanding or non-pneumatically expanding actuation force on the anchor to change the shape of the anchor, such as by applying proximally and/or distally directed force on the anchor using a releasable deployment tool to expand and contract the anchor or parts of the anchor. Another aspect of the invention provides an apparatus including a replacement valve; an anchor; and a deployment tool comprising a plurality of anchor actuation elements adapted to apply a non-hydraulically expanding or non-
(Continued)

pneumatically expanding actuation force on the anchor to reshape the anchor.

20 Claims, 54 Drawing Sheets

Related U.S. Application Data continuation of application No. 14/494,922, filed on Sep. 24, 2014, now Pat. No. 9,320,599, which is a continuation of application No. 13/157,733, filed on Jun. 10, 2011, now Pat. No. 8,858,620, which is a continuation of application No. 11/532,019, filed on Sep. 14, 2006, now abandoned, which is a continuation of application No. 10/982,388, filed on Nov. 5, 2004, now Pat. No. 7,959,666, which is a continuation-in-part of application No. 10/746,120, filed on Dec. 23, 2003, now abandoned.

(52) U.S. Cl.
CPC .......... *A61F 2/2412* (2013.01); *A61F 2/2418* (2013.01); *A61F 2/2436* (2013.01); *A61F 2/90* (2013.01); *A61F 2/2433* (2013.01); *A61F 2002/9528* (2013.01); *A61F 2220/005* (2013.01); *A61F 2220/0016* (2013.01); *A61F 2220/0058* (2013.01); *A61F 2230/005* (2013.01); *A61F 2230/008* (2013.01); *A61F 2230/0054* (2013.01); *A61F 2230/0078* (2013.01); *A61F 2250/006* (2013.01)

(58) Field of Classification Search
CPC ... A61F 2/90; A61F 2/2433; A61F 2002/9528
See application file for complete search history.

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Lowell |
| 3,113,586 A | 12/1963 | Edmark |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A * | 10/1986 | Kornberg ............... A61B 17/04 600/36 |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |

(56) References Cited

U.S. PATENT DOCUMENTS

| | | |
|---|---|---|
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,873,906 A | 2/1999 | Lau et al. |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,010,530 A | 1/2000 | Goicoechea |
| 6,022,370 A | 2/2000 | Tower |
| 6,027,520 A | 2/2000 | Tsugita et al. |
| 6,027,525 A | 2/2000 | Suh et al. |
| 6,042,554 A | 3/2000 | Rosenman et al. |
| 6,042,598 A | 3/2000 | Tsugita et al. |
| 6,042,607 A | 3/2000 | Williamson, et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A * | 12/2000 | Patterson .............. A61F 2/90 606/159 |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 * | 2/2001 | Hedges .............. A61B 17/221 606/108 |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Alba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |

(56) References Cited

U.S. PATENT DOCUMENTS

| | | | |
|---|---|---|---|
| 6,270,513 B1 | 8/2001 | Tsugita et al. | |
| 6,277,555 B1 | 8/2001 | Duran et al. | |
| 6,287,339 B1* | 9/2001 | Vazquez | A61F 2/2403 623/2.11 |
| 6,299,637 B1 | 10/2001 | Shaolian et al. | |
| 6,302,906 B1 | 10/2001 | Goicoechea et al. | |
| 6,309,417 B1 | 10/2001 | Spence et al. | |
| 6,319,281 B1 | 11/2001 | Patel | |
| 6,327,772 B1 | 12/2001 | Zadno-Azizi et al. | |
| 6,336,934 B1 | 1/2002 | Gilson et al. | |
| 6,336,937 B1 | 1/2002 | Vonesh et al. | |
| 6,338,735 B1 | 1/2002 | Stevens | |
| 6,346,116 B1 | 2/2002 | Brooks et al. | |
| 6,348,063 B1 | 2/2002 | Yassour et al. | |
| 6,352,554 B2 | 3/2002 | Paulis | |
| 6,352,708 B1 | 3/2002 | Duran et al. | |
| 6,361,545 B1 | 3/2002 | Macoviak et al. | |
| 6,363,938 B2 | 4/2002 | Saadat et al. | |
| 6,364,895 B1 | 4/2002 | Greenhalgh | |
| 6,371,970 B1 | 4/2002 | Khosravi et al. | |
| 6,371,983 B1 | 4/2002 | Lane | |
| 6,379,383 B1 | 4/2002 | Palmaz et al. | |
| 6,398,807 B1 | 6/2002 | Chouinard et al. | |
| 6,402,736 B1 | 6/2002 | Brown et al. | |
| 6,409,750 B1 | 6/2002 | Hyodoh et al. | |
| 6,416,510 B1 | 7/2002 | Altman et al. | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,303 B1 | 10/2002 | Amplatz et al. | |
| 6,468,660 B2 | 10/2002 | Ogle et al. | |
| 6,475,239 B1 | 11/2002 | Campbell et al. | |
| 6,482,228 B1 | 11/2002 | Norred | |
| 6,485,501 B1 | 11/2002 | Green | |
| 6,485,502 B2 | 11/2002 | Michael et al. | |
| 6,488,704 B1 | 12/2002 | Connelly et al. | |
| 6,494,909 B2 | 12/2002 | Greenhalgh | |
| 6,503,272 B2 | 1/2003 | Duerig et al. | |
| 6,508,803 B1 | 1/2003 | Horikawa et al. | |
| 6,508,833 B2 | 1/2003 | Pavcnik et al. | |
| 6,527,800 B1 | 3/2003 | McGuckin et al. | |
| 6,530,949 B2 | 3/2003 | Konya et al. | |
| 6,530,952 B2 | 3/2003 | Vesely | |
| 6,537,297 B2 | 3/2003 | Tsugita et al. | |
| 6,540,768 B1 | 4/2003 | Diaz et al. | |
| 6,562,058 B2 | 5/2003 | Seguin et al. | |
| 6,569,196 B1 | 5/2003 | Vesely | |
| 6,572,643 B1 | 6/2003 | Gharibadeh | |
| 6,585,766 B1 | 7/2003 | Huynh et al. | |
| 6,592,546 B1 | 7/2003 | Barbut et al. | |
| 6,592,614 B2 | 7/2003 | Lenker et al. | |
| 6,605,112 B1 | 8/2003 | Moll et al. | |
| 6,610,077 B1 | 8/2003 | Hancock et al. | |
| 6,616,682 B2 | 9/2003 | Joergensen et al. | |
| 6,622,604 B1 | 9/2003 | Chouinard et al. | |
| 6,623,518 B2* | 9/2003 | Thompson | A61F 2/91 606/108 |
| 6,623,521 B2 | 9/2003 | Steinke et al. | |
| 6,632,243 B1 | 10/2003 | Zadno-Azizi et al. | |
| 6,635,068 B1 | 10/2003 | Dubrul et al. | |
| 6,635,079 B2* | 10/2003 | Unsworth | A61F 2/90 623/1.11 |
| 6,652,571 B1 | 11/2003 | White et al. | |
| 6,652,578 B2 | 11/2003 | Bailey et al. | |
| 6,663,588 B2 | 12/2003 | DuBois et al. | |
| 6,663,663 B2 | 12/2003 | Kim et al. | |
| 6,669,724 B2 | 12/2003 | Park et al. | |
| 6,673,089 B1 | 1/2004 | Yassour et al. | |
| 6,673,109 B2 | 1/2004 | Cox | |
| 6,676,668 B2 | 1/2004 | Mercereau et al. | |
| 6,676,692 B2* | 1/2004 | Rabkin | A61F 2/95 604/104 |
| 6,676,698 B2 | 1/2004 | McGuckin et al. | |
| 6,682,543 B2 | 1/2004 | Barbut et al. | |
| 6,682,558 B2 | 1/2004 | Tu et al. | |
| 6,682,559 B2 | 1/2004 | Myers et al. | |
| 6,685,739 B2 | 2/2004 | DiMatteo et al. | |
| 6,689,144 B2 | 2/2004 | Gerberding | |
| 6,689,164 B1 | 2/2004 | Seguin | |
| 6,692,512 B2 | 2/2004 | Jang | |
| 6,695,864 B2 | 2/2004 | Macoviak et al. | |
| 6,695,865 B2 | 2/2004 | Boyle et al. | |
| 6,702,851 B1 | 3/2004 | Chinn et al. | |
| 6,712,842 B1 | 3/2004 | Gifford et al. | |
| 6,712,843 B2 | 3/2004 | Elliott | |
| 6,714,842 B1 | 3/2004 | Ito | |
| 6,719,789 B2 | 4/2004 | Cox | |
| 6,723,116 B2 | 4/2004 | Taheri | |
| 6,730,118 B2 | 5/2004 | Spenser et al. | |
| 6,730,377 B2 | 5/2004 | Wang | |
| 6,733,525 B2 | 5/2004 | Yang et al. | |
| 6,736,846 B2 | 5/2004 | Cox | |
| 6,752,828 B2 | 6/2004 | Thornton | |
| 6,755,854 B2 | 6/2004 | Gillick et al. | |
| 6,758,855 B2 | 7/2004 | Fulton et al. | |
| 6,764,503 B1 | 7/2004 | Ishimaru | |
| 6,764,509 B2 | 7/2004 | Chinn et al. | |
| 6,767,345 B2 | 7/2004 | Germain et al. | |
| 6,769,434 B2 | 8/2004 | Liddicoat et al. | |
| 6,773,454 B2 | 8/2004 | Wholey et al. | |
| 6,776,791 B1* | 8/2004 | Stallings | A61F 2/07 623/1.11 |
| 6,786,925 B1* | 9/2004 | Schoon | A61B 17/064 623/2.11 |
| 6,790,229 B1 | 9/2004 | Berreklouw | |
| 6,790,230 B2 | 9/2004 | Beyersdorf et al. | |
| 6,790,237 B2 | 9/2004 | Stinson | |
| 6,792,979 B2 | 9/2004 | Konya et al. | |
| 6,797,002 B2 | 9/2004 | Spence et al. | |
| 6,814,746 B2 | 11/2004 | Thompson et al. | |
| 6,821,297 B2 | 11/2004 | Snyders | |
| 6,830,585 B1 | 12/2004 | Artof et al. | |
| 6,837,901 B2* | 1/2005 | Rabkin | A61F 2/95 623/1.11 |
| 6,840,957 B2 | 1/2005 | DiMatteo et al. | |
| 6,843,802 B1 | 1/2005 | Villalobos et al. | |
| 6,849,085 B2 | 2/2005 | Marton | |
| 6,863,668 B2 | 3/2005 | Gillespie et al. | |
| 6,866,650 B2 | 3/2005 | Stevens et al. | |
| 6,866,669 B2 | 3/2005 | Buzzard et al. | |
| 6,872,223 B2 | 3/2005 | Roberts et al. | |
| 6,872,226 B2 | 3/2005 | Cali et al. | |
| 6,875,231 B2 | 4/2005 | Anduiza et al. | |
| 6,881,220 B2 | 4/2005 | Edwin et al. | |
| 6,887,266 B2 | 5/2005 | Williams et al. | |
| 6,890,340 B2 | 5/2005 | Duane | |
| 6,893,459 B1 | 5/2005 | Macoviak | |
| 6,893,460 B2 | 5/2005 | Spenser et al. | |
| 6,905,743 B1 | 6/2005 | Chen et al. | |
| 6,908,481 B2 | 6/2005 | Cribier | |
| 6,911,036 B2 | 6/2005 | Douk et al. | |
| 6,911,043 B2 | 6/2005 | Myers et al. | |
| 6,936,058 B2 | 8/2005 | Forde et al. | |
| 6,936,067 B2 | 8/2005 | Buchanan | |
| 6,939,352 B2 | 9/2005 | Buzzard et al. | |
| 6,951,571 B1 | 10/2005 | Srivastava | |
| 6,953,332 B1 | 10/2005 | Kurk et al. | |
| 6,964,673 B2 | 11/2005 | Tsugita et al. | |
| 6,969,395 B2 | 11/2005 | Eskuri | |
| 6,972,025 B2 | 12/2005 | WasDyke | |
| 6,974,464 B2 | 12/2005 | Quijano et al. | |
| 6,974,474 B2 | 12/2005 | Pavcnik et al. | |
| 6,974,476 B2 | 12/2005 | McGuckin et al. | |
| 6,979,350 B2 | 12/2005 | Moll et al. | |
| 6,984,242 B2 | 1/2006 | Campbell et al. | |
| 6,989,027 B2 | 1/2006 | Allen et al. | |
| 7,004,176 B2 | 2/2006 | Lau | |
| 7,011,681 B2* | 3/2006 | Vesely | A61F 2/2409 623/1.11 |
| 7,018,406 B2 | 3/2006 | Seguin et al. | |
| 7,025,791 B2 | 4/2006 | Levine et al. | |

(56) References Cited

U.S. PATENT DOCUMENTS

| | | | |
|---|---|---|---|
| 7,037,331 B2 * | 5/2006 | Mitelberg | A61F 2/91 623/1.11 |
| 7,041,132 B2 | 5/2006 | Quijano et al. | |
| 7,097,658 B2 | 8/2006 | Oktay | |
| 7,097,659 B2 | 8/2006 | Woolfson et al. | |
| 7,122,020 B2 | 10/2006 | Mogul | |
| 7,125,418 B2 | 10/2006 | Duran et al. | |
| 7,141,063 B2 | 11/2006 | White et al. | |
| 7,166,097 B2 | 1/2007 | Barbut | |
| 7,175,653 B2 | 2/2007 | Gaber | |
| 7,175,654 B2 | 2/2007 | Bonsignore et al. | |
| 7,175,656 B2 | 2/2007 | Khairkhahan | |
| 7,189,258 B2 | 3/2007 | Johnson et al. | |
| 7,191,018 B2 | 3/2007 | Gielen et al. | |
| 7,201,772 B2 | 4/2007 | Schwammenthal et al. | |
| 7,235,093 B2 * | 6/2007 | Gregorich | A61F 2/91 623/1.11 |
| 7,258,696 B2 * | 8/2007 | Rabkin | A61F 2/95 606/191 |
| 7,267,686 B2 | 9/2007 | DiMatteo et al. | |
| 7,276,078 B2 | 10/2007 | Spenser et al. | |
| 7,322,932 B2 | 1/2008 | Xie et al. | |
| 7,326,236 B2 | 2/2008 | Andreas et al. | |
| 7,329,279 B2 | 2/2008 | Haug et al. | |
| 7,374,560 B2 | 5/2008 | Ressemann et al. | |
| 7,374,571 B2 | 5/2008 | Pease et al. | |
| 7,381,219 B2 | 6/2008 | Salahieh et al. | |
| 7,381,220 B2 | 6/2008 | Macoviak et al. | |
| 7,399,315 B2 | 7/2008 | Iobbi | |
| 7,445,631 B2 | 11/2008 | Salahieh et al. | |
| 7,470,285 B2 | 12/2008 | Nugent et al. | |
| 7,473,417 B2 | 1/2009 | Zeltinger et al. | |
| 7,491,232 B2 | 2/2009 | Bolduc et al. | |
| 7,510,574 B2 | 3/2009 | Lê et al. | |
| 7,524,330 B2 | 4/2009 | Berreklouw | |
| 7,530,995 B2 | 5/2009 | Quijano et al. | |
| 7,544,206 B2 | 6/2009 | Cohn | |
| 7,569,071 B2 | 8/2009 | Haverkost et al. | |
| 7,601,159 B2 | 10/2009 | Ewers et al. | |
| 7,622,276 B2 | 11/2009 | Cunanan et al. | |
| 7,628,802 B2 | 12/2009 | White et al. | |
| 7,628,803 B2 | 12/2009 | Pavcnik et al. | |
| 7,632,298 B2 | 12/2009 | Hijlkema et al. | |
| 7,641,687 B2 | 1/2010 | Chinn et al. | |
| 7,674,282 B2 | 3/2010 | Wu et al. | |
| 7,712,606 B2 | 5/2010 | Salahieh et al. | |
| 7,722,638 B2 | 5/2010 | Deyette et al. | |
| 7,722,662 B2 | 5/2010 | Steinke et al. | |
| 7,722,666 B2 | 5/2010 | Lafontaine | |
| 7,736,388 B2 | 6/2010 | Goldfarb et al. | |
| 7,748,389 B2 | 7/2010 | Salahieh et al. | |
| 7,758,625 B2 | 7/2010 | Wu et al. | |
| 7,763,065 B2 | 7/2010 | Schmid et al. | |
| 7,771,467 B2 | 8/2010 | Svensson | |
| 7,780,725 B2 | 8/2010 | Haug et al. | |
| 7,799,065 B2 | 9/2010 | Pappas | |
| 7,803,185 B2 | 9/2010 | Gabbay | |
| 7,824,442 B2 | 11/2010 | Salahieh et al. | |
| 7,824,443 B2 | 11/2010 | Salahieh et al. | |
| 7,833,262 B2 | 11/2010 | McGuckin et al. | |
| 7,846,204 B2 | 12/2010 | Letac et al. | |
| 7,857,845 B2 | 12/2010 | Stacchino et al. | |
| 7,892,292 B2 | 2/2011 | Stack et al. | |
| 7,914,574 B2 | 3/2011 | Schmid et al. | |
| 7,918,880 B2 | 4/2011 | Austin | |
| 7,927,363 B2 | 4/2011 | Perouse | |
| 7,938,851 B2 | 5/2011 | Olson et al. | |
| 7,947,071 B2 | 5/2011 | Schmid et al. | |
| 7,959,666 B2 | 6/2011 | Salahieh et al. | |
| 7,959,672 B2 | 6/2011 | Salahieh et al. | |
| 7,967,853 B2 | 6/2011 | Eidenschink et al. | |
| 7,988,724 B2 | 8/2011 | Salahieh et al. | |
| 8,048,153 B2 | 11/2011 | Salahieh et al. | |
| 8,052,749 B2 | 11/2011 | Salahieh et al. | |
| 8,133,270 B2 | 3/2012 | Kheradvar et al. | |
| 8,136,659 B2 | 3/2012 | Salahieh et al. | |
| 8,157,853 B2 | 4/2012 | Laske et al. | |
| 8,167,894 B2 | 5/2012 | Miles et al. | |
| 8,172,896 B2 | 5/2012 | McNamara et al. | |
| 8,182,528 B2 | 5/2012 | Salahieh et al. | |
| 8,192,351 B2 | 6/2012 | Fishler et al. | |
| 8,226,707 B2 | 7/2012 | White | |
| 8,226,710 B2 | 7/2012 | Nguyen et al. | |
| 8,231,670 B2 | 7/2012 | Salahieh et al. | |
| 8,236,049 B2 | 8/2012 | Rowe et al. | |
| 8,246,678 B2 | 8/2012 | Salahieh et al. | |
| 8,252,051 B2 | 8/2012 | Chau et al. | |
| 8,252,052 B2 | 8/2012 | Salahieh et al. | |
| 8,277,500 B2 | 10/2012 | Schmid et al. | |
| 8,287,584 B2 | 10/2012 | Salahieh et al. | |
| 8,308,798 B2 | 11/2012 | Pintor et al. | |
| 8,317,858 B2 | 11/2012 | Straubinger et al. | |
| 8,323,335 B2 | 12/2012 | Rowe et al. | |
| 8,328,868 B2 | 12/2012 | Paul et al. | |
| 8,343,213 B2 | 1/2013 | Salahieh et al. | |
| 8,348,999 B2 | 1/2013 | Kheradvar et al. | |
| 8,366,767 B2 | 2/2013 | Zhang | |
| 8,376,865 B2 | 2/2013 | Forster et al. | |
| 8,377,117 B2 | 2/2013 | Keidar et al. | |
| 8,398,708 B2 * | 3/2013 | Meiri | A61B 17/0487 623/2.11 |
| 8,403,983 B2 | 3/2013 | Quadri et al. | |
| 8,414,644 B2 | 4/2013 | Quadri et al. | |
| 8,414,645 B2 | 4/2013 | Dwork et al. | |
| 8,512,394 B2 | 8/2013 | Schmid et al. | |
| 8,523,936 B2 | 9/2013 | Schmid et al. | |
| 8,540,762 B2 | 9/2013 | Schmid et al. | |
| 8,545,547 B2 | 10/2013 | Schmid et al. | |
| 8,579,962 B2 | 11/2013 | Salahieh et al. | |
| 8,591,570 B2 | 11/2013 | Revuelta et al. | |
| 8,603,160 B2 | 12/2013 | Salahieh et al. | |
| 8,617,235 B2 | 12/2013 | Schmid et al. | |
| 8,617,236 B2 | 12/2013 | Paul et al. | |
| 8,623,074 B2 | 1/2014 | Ryan | |
| 8,623,076 B2 | 1/2014 | Salahieh et al. | |
| 8,623,078 B2 | 1/2014 | Salahieh et al. | |
| 8,668,733 B2 | 3/2014 | Haug et al. | |
| 8,828,078 B2 | 9/2014 | Salahieh et al. | |
| 8,840,662 B2 | 9/2014 | Salahieh et al. | |
| 8,840,663 B2 | 9/2014 | Salahieh et al. | |
| 8,852,272 B2 | 10/2014 | Gross et al. | |
| 8,858,620 B2 | 10/2014 | Salahieh et al. | |
| 8,894,703 B2 | 11/2014 | Salahieh et al. | |
| 8,992,608 B2 | 3/2015 | Haug et al. | |
| 8,998,976 B2 | 4/2015 | Gregg et al. | |
| 9,005,273 B2 | 4/2015 | Salahieh et al. | |
| 9,011,521 B2 | 4/2015 | Haug et al. | |
| 9,039,756 B2 | 5/2015 | White | |
| 9,149,358 B2 | 10/2015 | Tabor et al. | |
| 9,168,136 B2 | 10/2015 | Yang et al. | |
| 9,180,005 B1 | 11/2015 | Lashinski et al. | |
| 9,211,266 B2 * | 12/2015 | Iwazawa | A61K 9/7007 |
| 9,265,608 B2 * | 2/2016 | Miller | A61F 2/2445 |
| 9,320,599 B2 | 4/2016 | Salahieh et al. | |
| 9,326,853 B2 | 5/2016 | Olson et al. | |
| 9,370,421 B2 | 6/2016 | Crisostomo et al. | |
| 9,393,115 B2 | 7/2016 | Tabor et al. | |
| 9,492,276 B2 | 11/2016 | Lee et al. | |
| 9,532,872 B2 | 1/2017 | Salahieh et al. | |
| 9,539,091 B2 | 1/2017 | Yang et al. | |
| 9,597,432 B2 * | 3/2017 | Nakamura | A61L 27/222 |
| 9,649,212 B2 * | 5/2017 | Fargahi | A61F 2/966 |
| 9,775,709 B2 * | 10/2017 | Miller | A61F 2/2445 |
| 9,901,445 B2 * | 2/2018 | Backus | A61F 2/2412 |
| 9,956,075 B2 | 5/2018 | Salahieh et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0039450 A1 | 11/2001 | Pavcnik et al. | |
| 2001/0041928 A1 | 11/2001 | Pavcnik et al. | |
| 2001/0041930 A1 | 11/2001 | Globerman et al. | |

(56) References Cited

U.S. PATENT DOCUMENTS

| | | |
|---|---|---|
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1* | 5/2002 | Forde ............... A61F 2/01 623/1.11 |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120323 A1 | 8/2002 | Thompson et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1* | 12/2002 | Bolea ............... A61F 2/90 623/1.11 |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Klyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1* | 11/2004 | Swanson ............... A61F 2/2487 623/1.11 |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043585 A1* | 2/2005 | Datta ............... A61F 2/0077 600/153 |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |

(56) References Cited

U.S. PATENT DOCUMENTS

| | | |
|---|---|---|
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0256532 A1* | 11/2005 | Nayak .............. A61B 17/0057 606/151 |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0212110 A1 | 9/2006 | Osborne et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0088431 A1 | 4/2007 | Bourang et al. |
| 2007/0100427 A1* | 5/2007 | Perouse .................... A61F 2/07 623/1.11 |
| 2007/0112355 A1 | 5/2007 | Salahieh et al. |
| 2007/0118214 A1 | 5/2007 | Salahieh et al. |
| 2007/0155010 A1* | 7/2007 | Farnsworth ............ A61L 27/18 435/399 |
| 2007/0162107 A1 | 7/2007 | Haug et al. |
| 2007/0173918 A1 | 7/2007 | Dreher et al. |
| 2007/0203503 A1* | 8/2007 | Salahieh ............ A61B 17/0644 606/108 |
| 2007/0203560 A1 | 8/2007 | Forster et al. |
| 2007/0244552 A1 | 10/2007 | Salahieh et al. |
| 2007/0265701 A1 | 11/2007 | Gurskis et al. |
| 2007/0288089 A1 | 12/2007 | Gurskis et al. |
| 2008/0004696 A1 | 1/2008 | Vesely |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0109070 A1* | 5/2008 | Wagner ............... A61L 27/3843 623/1.41 |
| 2008/0125859 A1 | 5/2008 | Salahieh et al. |
| 2008/0140189 A1 | 6/2008 | Nguyen et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0262592 A1* | 10/2008 | Jordan ..................... A61F 2/95 623/1.11 |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0082844 A1 | 3/2009 | Zacharias et al. |
| 2009/0093877 A1 | 4/2009 | Keidar et al. |
| 2009/0163951 A1 | 6/2009 | Simmons et al. |
| 2009/0171456 A1 | 7/2009 | Kveen et al. |
| 2009/0210052 A1 | 8/2009 | Forster et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2009/0319037 A1* | 12/2009 | Rowe .................... A61F 2/2445 623/2.11 |
| 2010/0004739 A1 | 1/2010 | Vesely |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |

(56) References Cited

U.S. PATENT DOCUMENTS

| | | |
|---|---|---|
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0268332 A1 | 10/2010 | Tuval et al. |
| 2010/0280495 A1 | 11/2010 | Paul et al. |
| 2010/0298931 A1 | 11/2010 | Quadri et al. |
| 2011/0040366 A1 | 2/2011 | Goetz et al. |
| 2011/0098805 A1 | 4/2011 | Dwork et al. |
| 2011/0257735 A1 | 10/2011 | Salahieh et al. |
| 2011/0264191 A1* | 10/2011 | Rothstein .............. A61F 2/2418 623/1.11 |
| 2011/0264196 A1 | 10/2011 | Savage et al. |
| 2011/0264203 A1 | 10/2011 | Dwork et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1* | 1/2012 | Olson ................... A61F 2/2418 623/1.11 |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0078357 A1 | 3/2012 | Conklin |
| 2012/0089224 A1 | 4/2012 | Haug et al. |
| 2012/0100182 A1* | 4/2012 | Mooney ................ A61K 39/39 424/400 |
| 2012/0132547 A1 | 5/2012 | Salahieh et al. |
| 2012/0165957 A1* | 6/2012 | Everland .............. A61F 2/0045 623/23.72 |
| 2012/0179244 A1 | 7/2012 | Schankereli et al. |
| 2012/0197379 A1 | 8/2012 | Laske et al. |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0046373 A1 | 2/2013 | Cartledge et al. |
| 2013/0066342 A1 | 3/2013 | Dell et al. |
| 2013/0071441 A1* | 3/2013 | Iwazawa .............. A61K 9/7007 424/400 |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0123796 A1* | 5/2013 | Sutton ............... A61B 17/00234 606/108 |
| 2013/0138207 A1 | 5/2013 | Quadri et al. |
| 2013/0158656 A1* | 6/2013 | Sutton .................. A61F 2/2436 623/2.11 |
| 2013/0166017 A1* | 6/2013 | Cartledge ................ A61F 2/93 623/1.15 |
| 2013/0184813 A1 | 7/2013 | Quadri et al. |
| 2013/0190865 A1 | 7/2013 | Anderson |
| 2013/0245752 A1 | 9/2013 | Goetz et al. |
| 2013/0253640 A1* | 9/2013 | Meiri ................ A61B 17/0487 623/2.11 |
| 2013/0289698 A1* | 10/2013 | Wang ................... A61F 2/2436 623/1.12 |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1* | 11/2013 | Kheradvar ............ A61F 2/2439 623/2.11 |
| 2013/0325101 A1 | 12/2013 | Goetz et al. |
| 2013/0338755 A1 | 12/2013 | Goetz et al. |
| 2014/0018911 A1 | 1/2014 | Zhou et al. |
| 2014/0052239 A1 | 2/2014 | Kong et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243962 A1 | 8/2014 | Wilson et al. |
| 2014/0243967 A1 | 8/2014 | Salahieh et al. |
| 2014/0249621 A1 | 9/2014 | Eidenschink |
| 2014/0277414 A1 | 9/2014 | Kheradvar |
| 2014/0296962 A1* | 10/2014 | Cartledge ............... A61F 2/243 623/1.12 |
| 2015/0012085 A1 | 1/2015 | Salahieh et al. |
| 2015/0073541 A1 | 3/2015 | Salahieh et al. |
| 2015/0127094 A1 | 5/2015 | Salahieh et al. |
| 2015/0352252 A1* | 12/2015 | Nakamura ........... A61L 27/222 424/422 |
| 2016/0120645 A1* | 5/2016 | Alon .................... A61F 2/2442 623/2.4 |
| 2017/0000609 A1* | 1/2017 | Gross .................... A61F 2/2445 |
| 2017/0056172 A1 | 3/2017 | Salahieh et al. |
| 2017/0095595 A1* | 4/2017 | Nakamura .............. A61L 27/00 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |

(56) References Cited

FOREIGN PATENT DOCUMENTS

| | | |
|---|---|---|
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A2 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006093795 A1 | 9/2006 |
| WO | 2007009117 A1 | 1/2007 |
| WO | 2007035471 A2 | 3/2007 |
| WO | 2006138391 A2 | 4/2007 |
| WO | 2007044285 A2 | 4/2007 |
| WO | 2007058847 A2 | 5/2007 |
| WO | 2007092354 A2 | 8/2007 |
| WO | 2007097983 A2 | 8/2007 |
| WO | 2007053243 A2 | 9/2007 |
| WO | 2007033093 A2 | 1/2008 |
| WO | 2008028569 A1 | 3/2008 |
| WO | 2008035337 A2 | 3/2008 |
| WO | 2010042950 A2 | 4/2010 |
| WO | 2010098857 A1 | 9/2010 |
| WO | 2012116368 A2 | 8/2012 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Continuous", Collins English Dictionary, pp. 1-3, accessed Mar. 18, 2014.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.

(56) References Cited

OTHER PUBLICATIONS

Cribier et al., "Percutaneous Transcatheter Implementation of an Aortic Valve Prosthesis for Calcitic Aortic Stenosis: First Human Case Description." Circulation, 106: 3006-3008, Dec. 10, 2002.
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Levy, "*Mycobacterium chelonei* Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stassano. "Mid-term Results of the Valve-on-Valve Technique for Bioprosthetic Failure." European Journal of Cardiothoracic Surgery: vol. 18, 453-457, Oct. 2000.
Stuart, "In Heart Valves, A Brave, New Non-Surgical World." Start-Up. Feb. 9-17, 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Topol. "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
Fluency Vascular Stent Graft Instructions for Use (2003).
USPPTO Case IPR2017-01293, U.S. Pat. No. 8,992,608 B, Oct. 13, 2017.
USPTO Case IPR2016-___, U.S. Pat. No. 8,992,608 "Petition for Interpartes Review of U.S. Pat. No. 8,992,608" Oct. 12, 2016.
USPTO Case IPR 2017-0006, U.S. Pat. No. 8,992,608 B2, "Final Written Decision" dated Mar. 23, 2018.
Carpentier-Edwards Perimount Bioprosthesis (2003).

\* cited by examiner

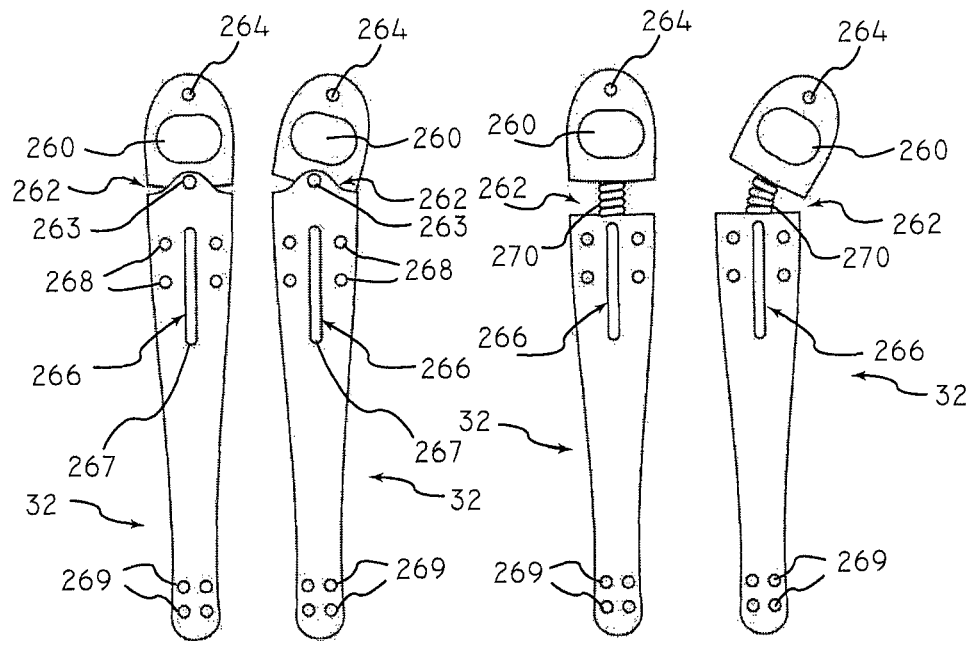
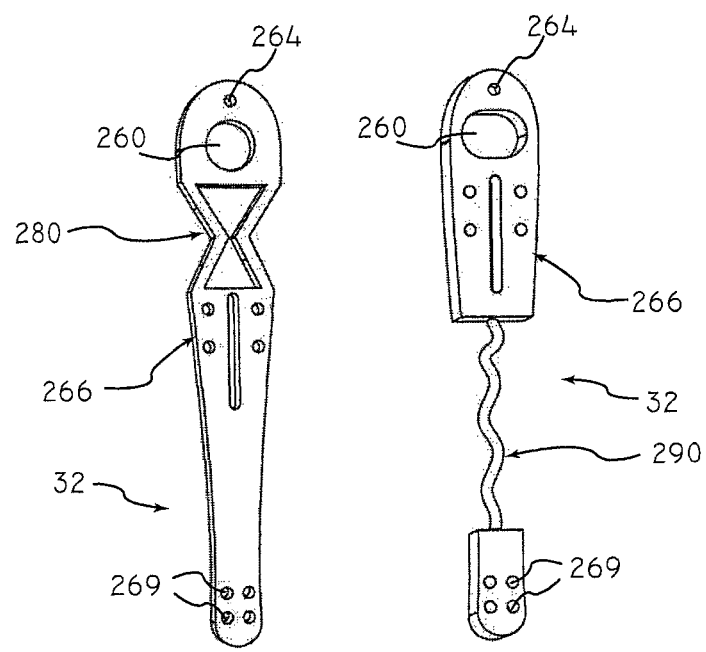
FIG 15A   FIG 15B   FIG 16A   FIG 16B
FIG 17   FIG 18

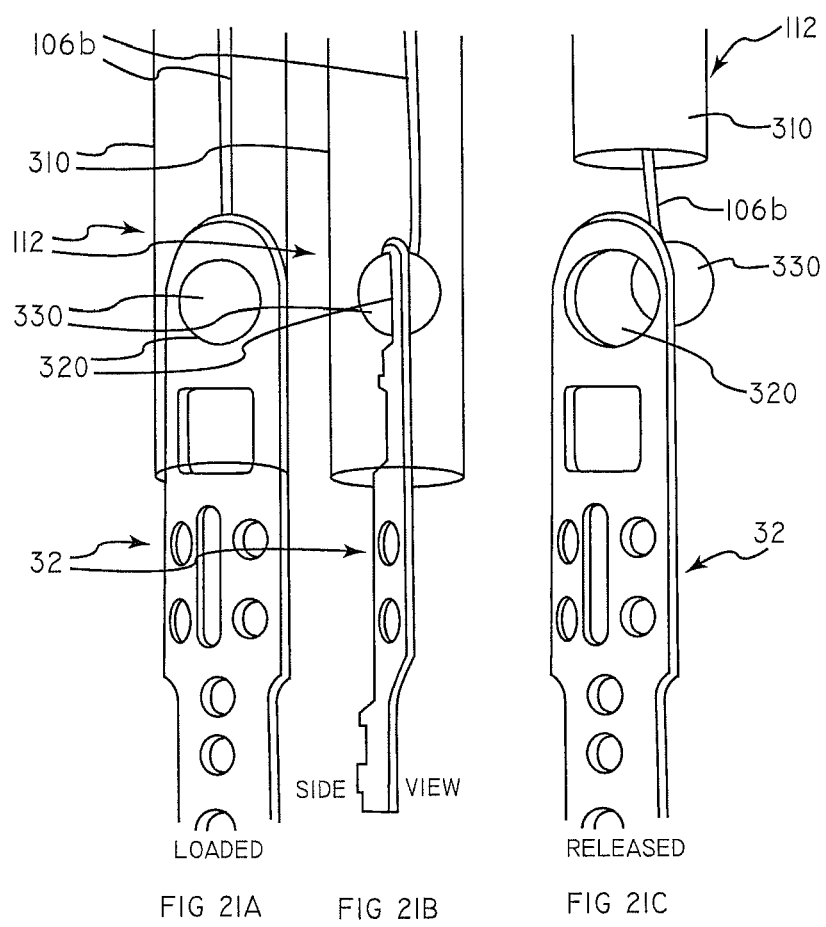

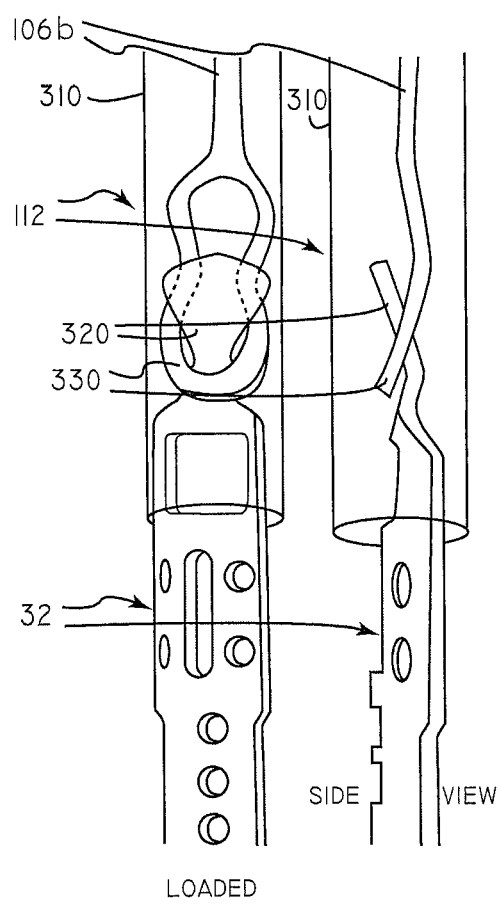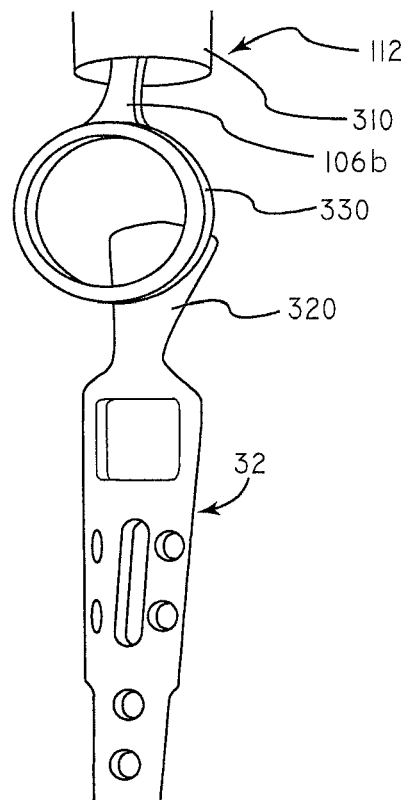
LOADED    RELEASED
FIG 23A  FIG 23B    FIG 23C

LOADED    RELEASED

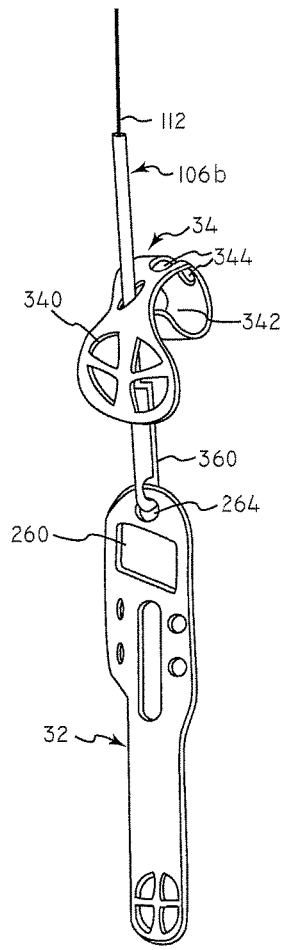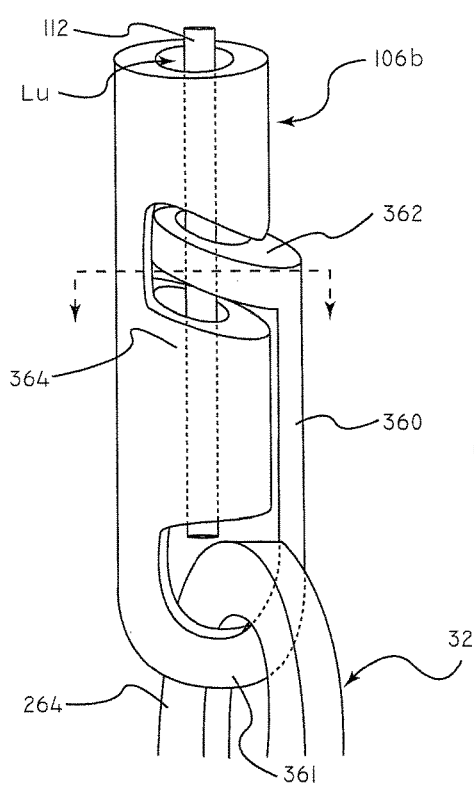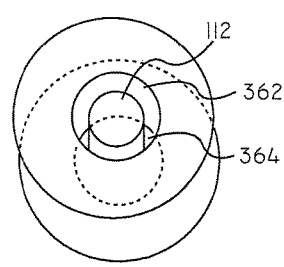
FIG 26A FIG 26B

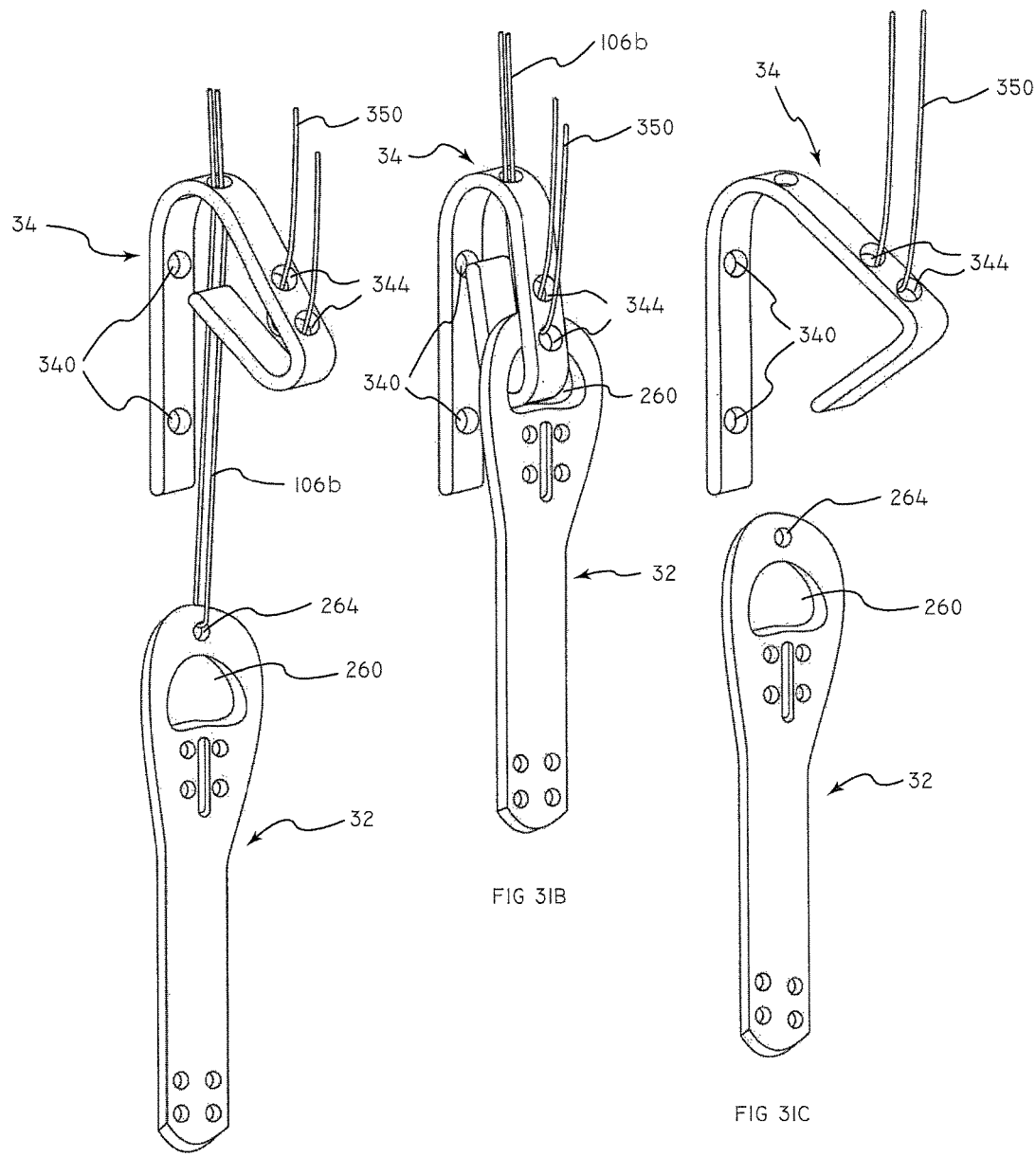

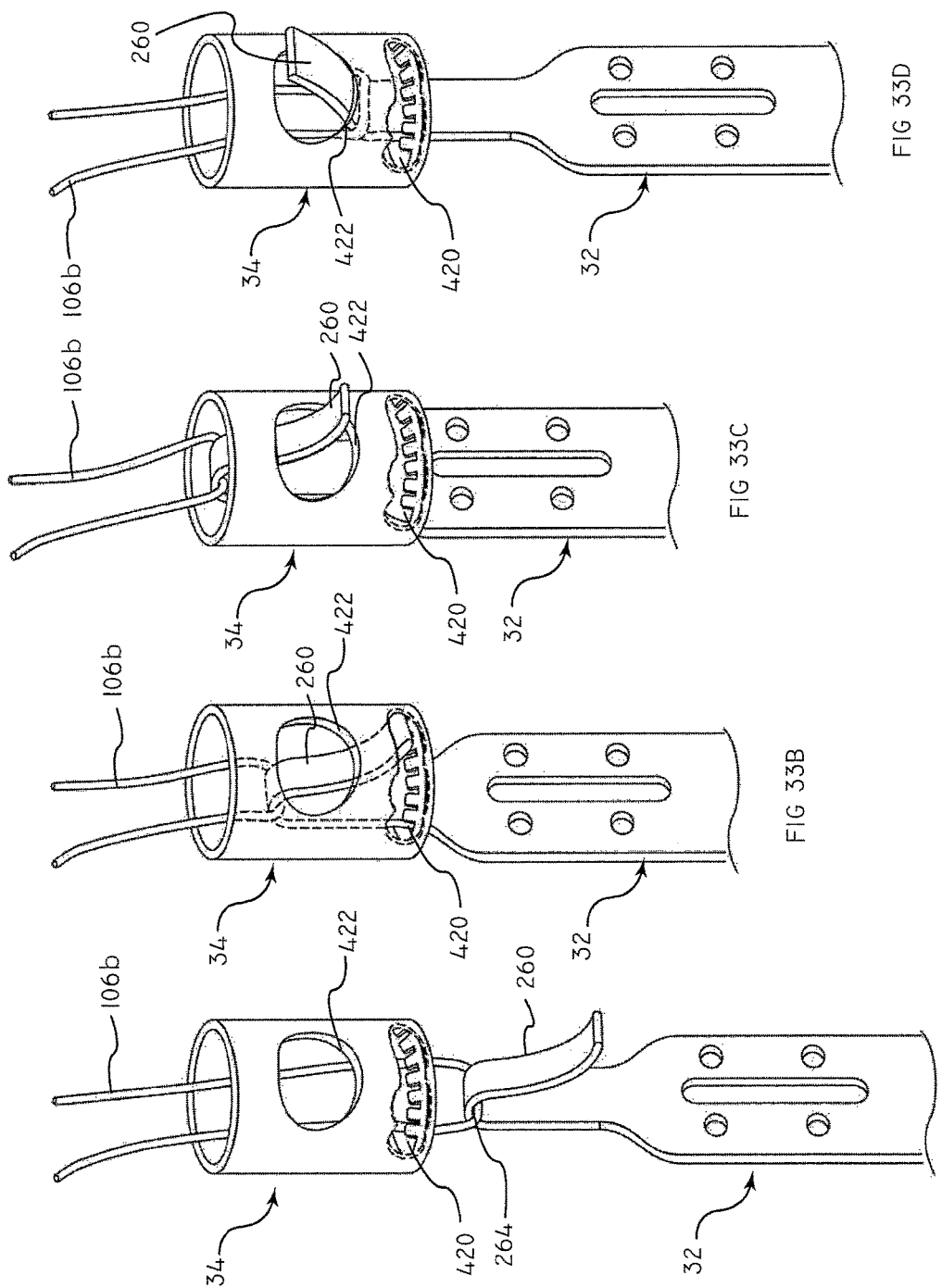

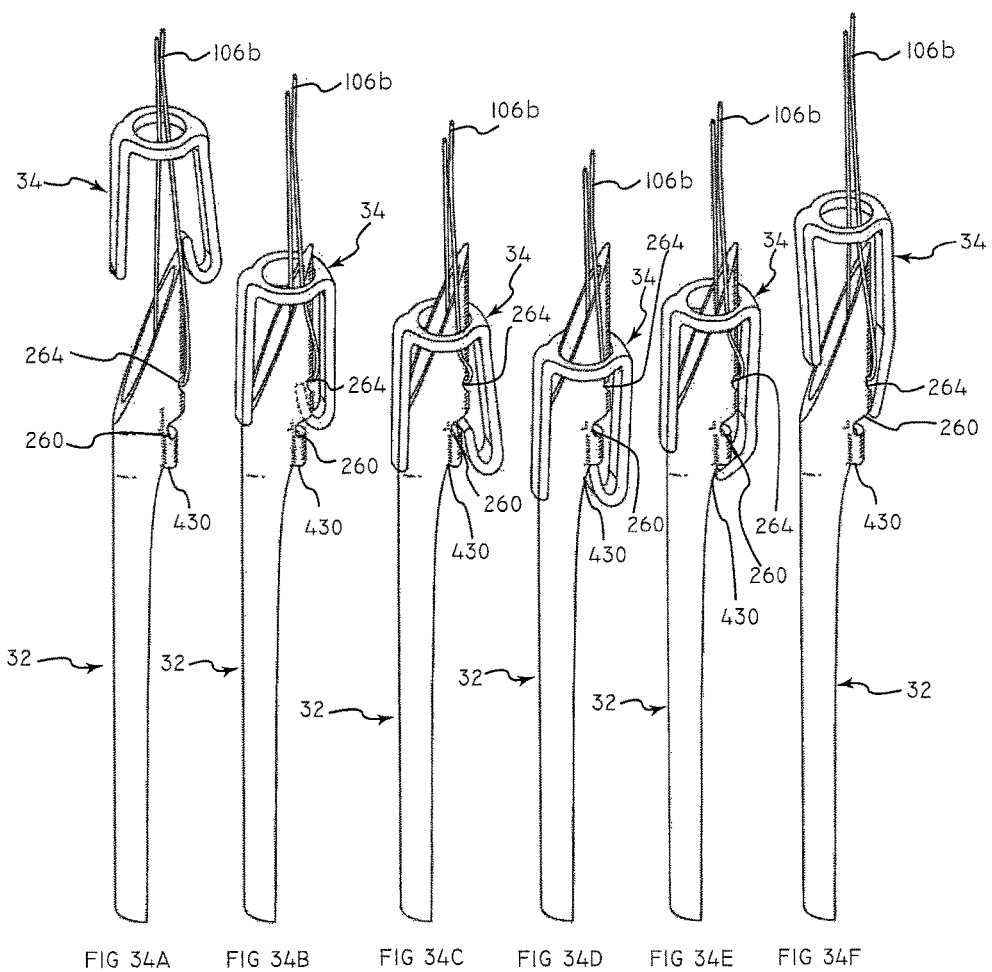

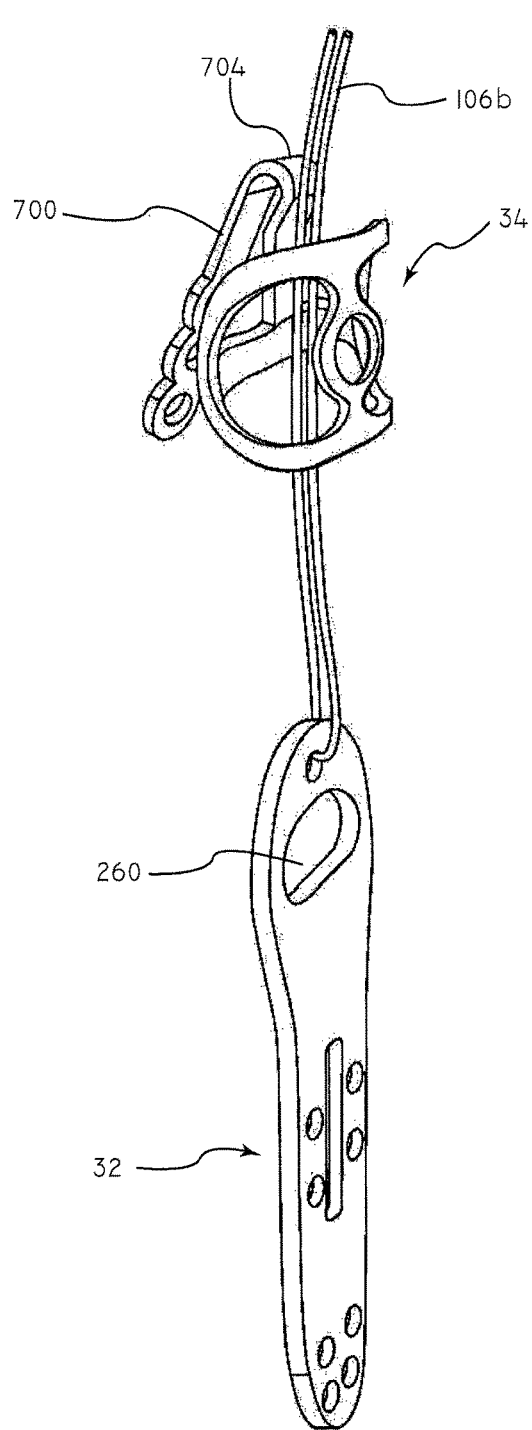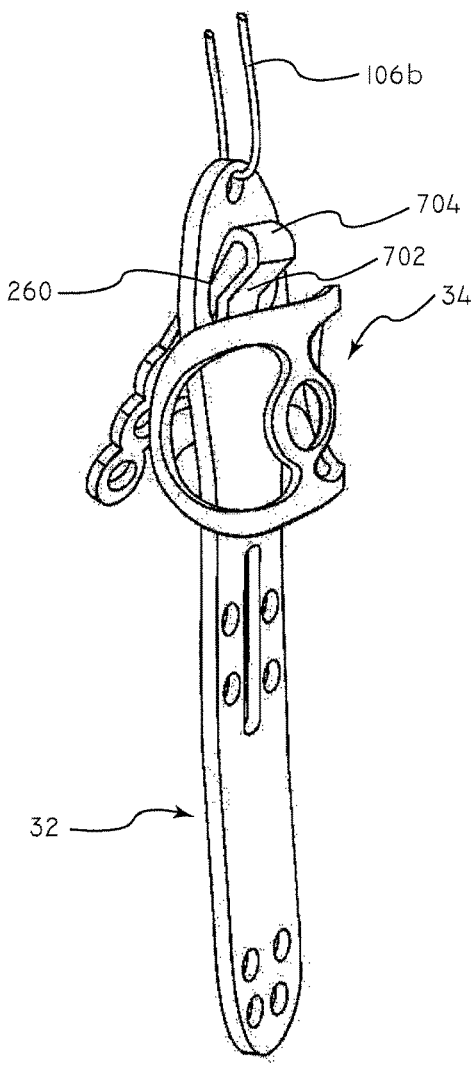
FIG 35A
FIG 35B

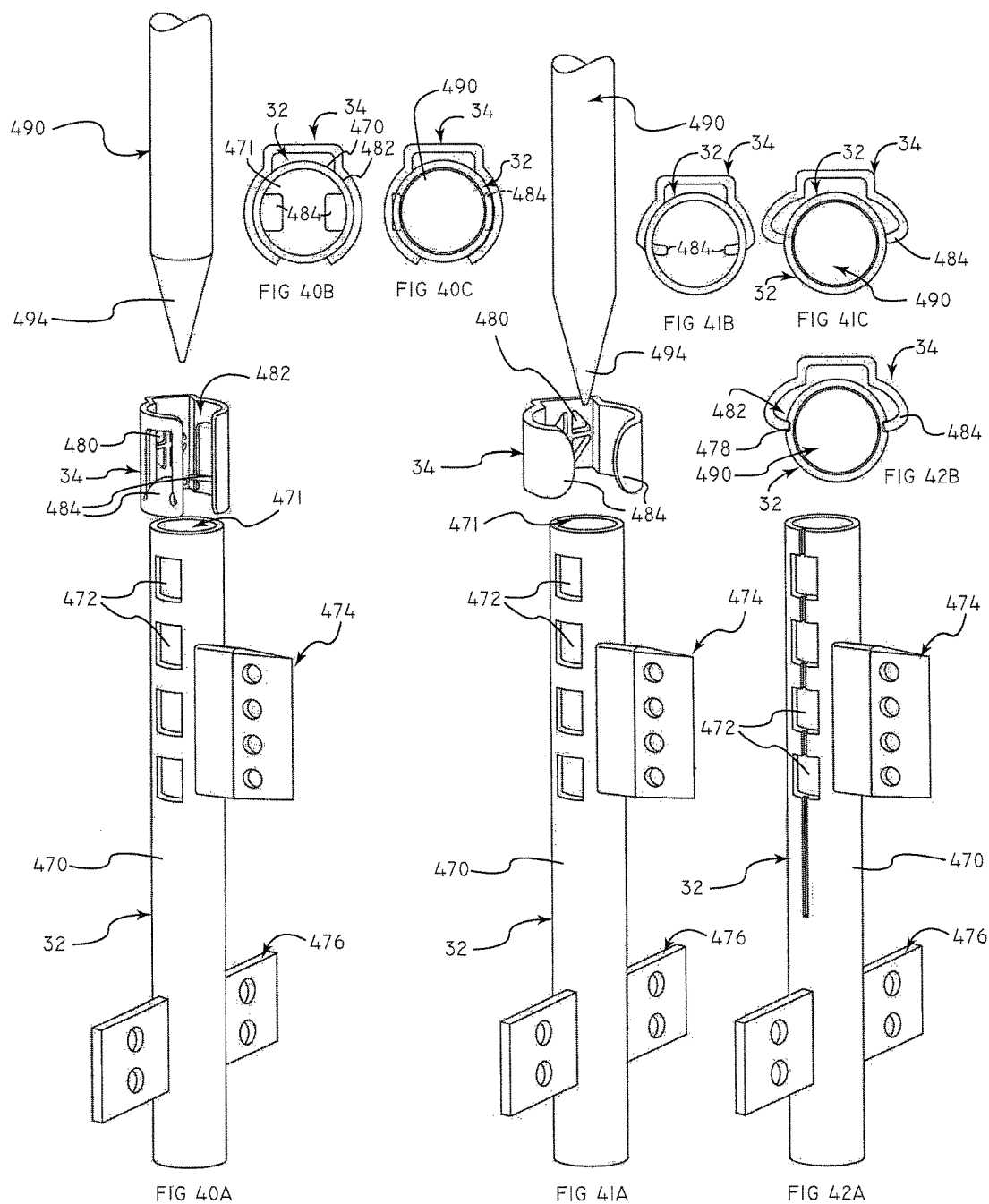

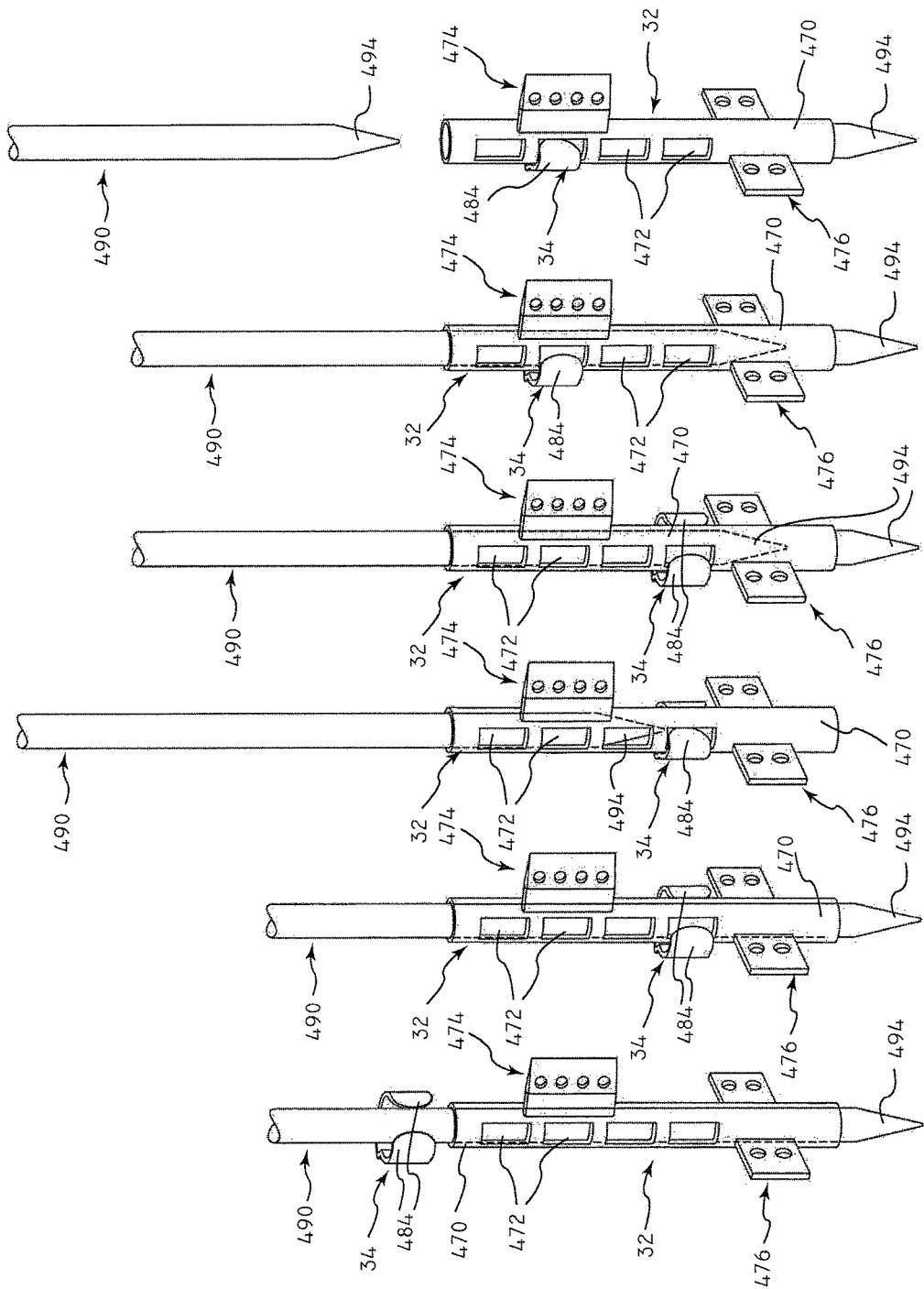

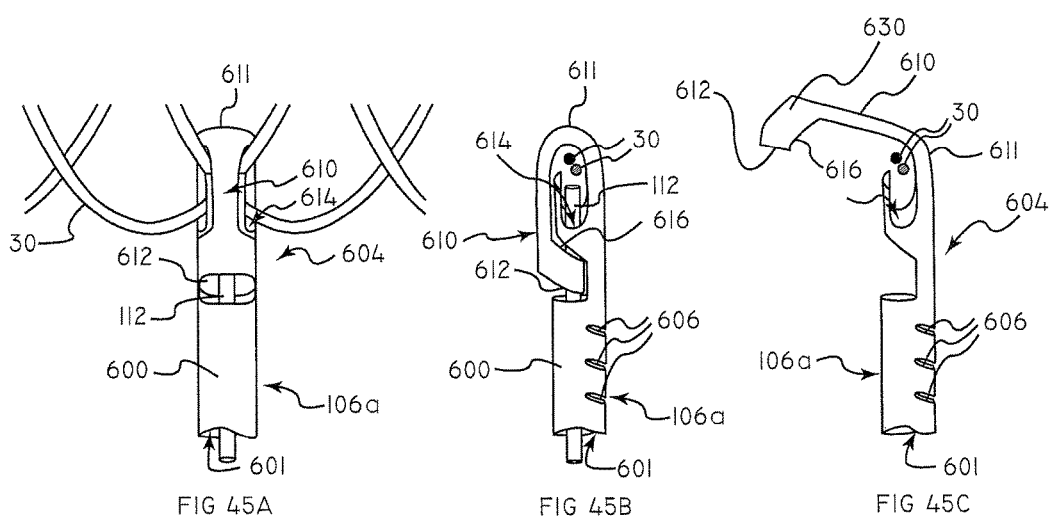

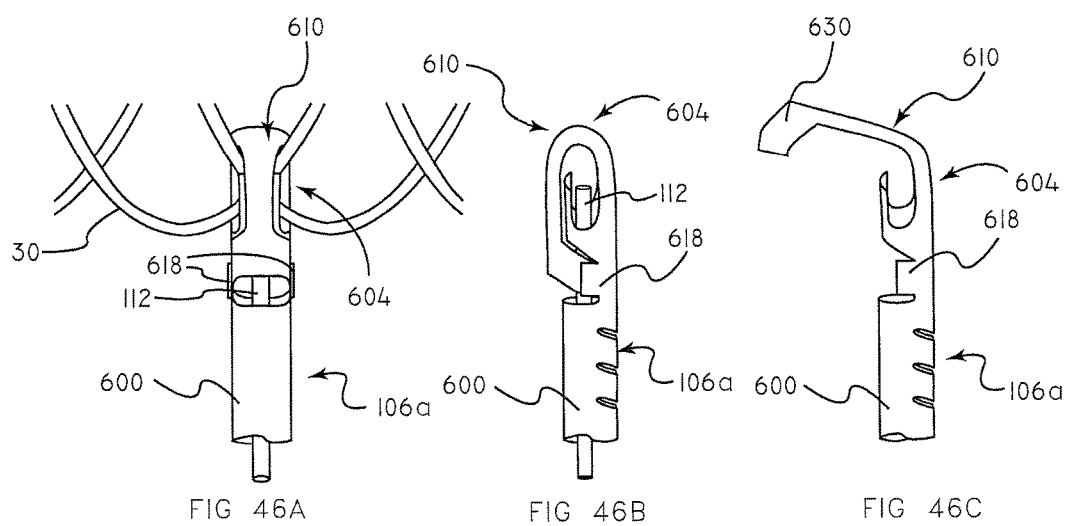

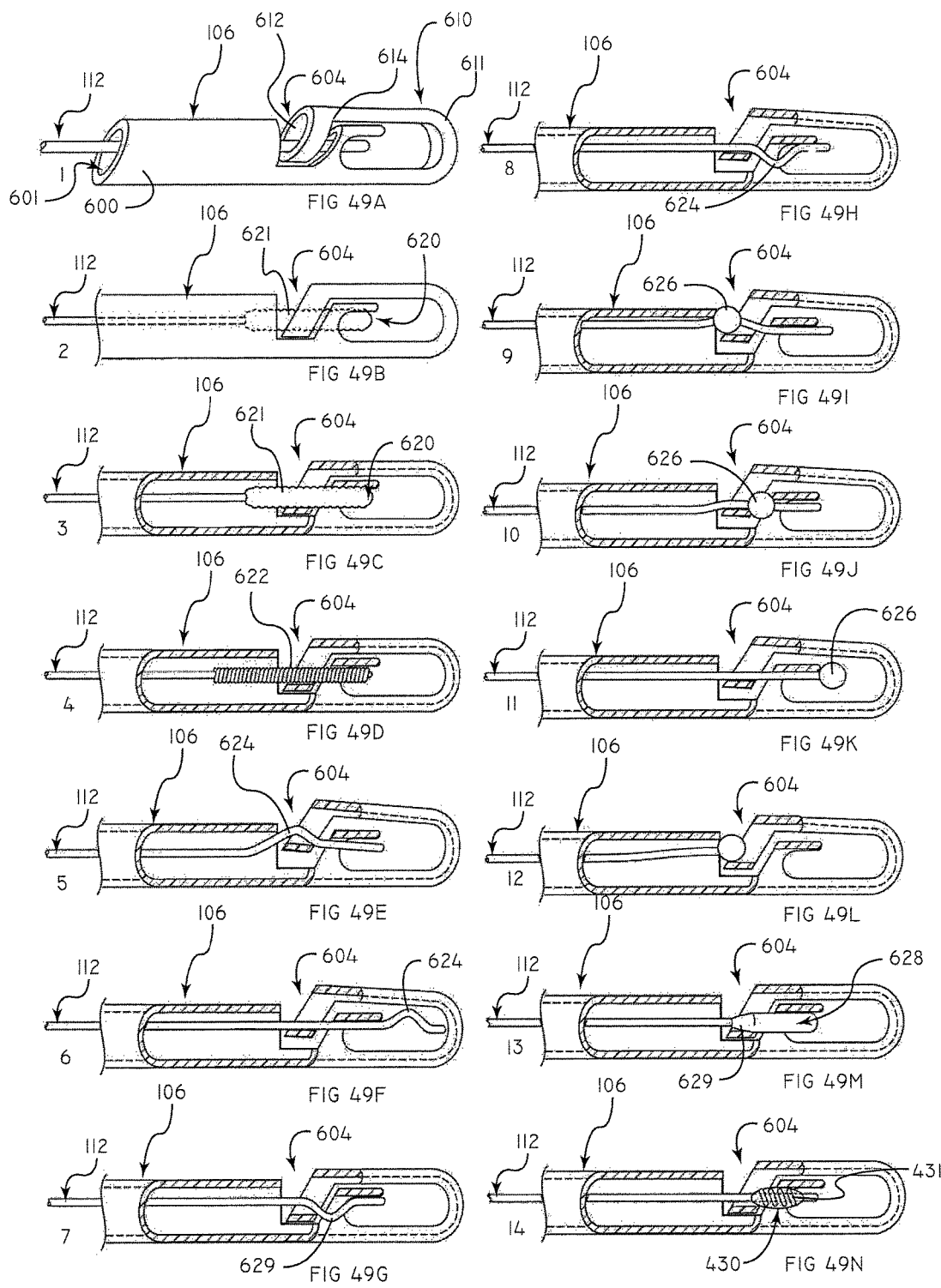

METHODS AND APPARATUS FOR ENDOVASCULARLY REPLACING A HEART VALVE

CROSS REFERENCE TO RELATED APPLICATIONS

This application is a continuation of application Ser. No. 15/138,863, filed Apr. 26, 2016, which is a continuation of application Ser. No. 14/494,922, filed Sep. 24, 2014, now U.S. Pat. No. 9,320,599, which is a continuation of application Ser. No. 13/157,733, filed Jun. 10, 2011, now U.S. Pat. No. 8,858,620 which is a continuation of application Ser. No. 11/532,019, filed Sep. 14, 2006, now abandoned, which is a continuation of application Ser. No. 10/982,388, filed Nov. 5, 2004, now U.S. Pat. No. 7,959,666 which is a continuation-in-part of application Ser. No. 10/746,120, filed Dec. 23, 2003, now abandoned, the entire disclosure of each application being incorporated herein by reference.

BACKGROUND OF THE INVENTION

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. Two to five percent of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. See, e.g., U.S. Pat. No. 6,168,614. In many of these procedures, the replacement valve is deployed across the native diseased valve to permanently hold the valve open, thereby alleviating a need to excise the native valve and to position the replacement valve in place of the native valve.

In the endovascular aortic valve replacement procedure, accurate placement of aortic valves relative to coronary ostia and the mitral valve is critical. Valve anchors comprising standard self-expanding stent systems are expected to have very poor accuracy in deployment, however. In a typical deployment procedure, the proximal end of the stent is not released from the delivery system until accurate placement is verified by fluoroscopy. The stent may jump to another position once released, making it impossible to know where the ends of the stent will be after release with respect to the native valve, the coronary ostia and the mitral valve.

Also, visualization of the way the new valve is functioning prior to final deployment is very desirable. Due to the expected jumping action of some self-expanding anchors, and because the replacement valve may not be fully functional before final deployment, visualization of valve function and position prior to final and irreversible deployment may not be possible with these systems.

Another expected drawback of prior art self-expanding replacement heart valve systems is their relative lack of radial strength. In order for self-expanding systems to be easily delivered through a delivery sheath, the metal needs to flex and bend inside the delivery catheter without being plastically deformed. Expandable stent designs suitable for endovascular delivery for other purposes may not have sufficient radial strength to serve as replacement heart valve anchors. For example, there are many commercial arterial stent systems that apply adequate radial force against the artery wall to treat atherosclerosis and that can collapse to a small enough of a diameter to fit inside a delivery catheter without plastically deforming. However, when the stent has a valve fastened inside it, and that valve must reside within the heart, as is the case in aortic valve replacement, the anchoring of the stent to vessel walls takes significantly more radial force, especially during diastole. The force to hold back arterial pressure and prevent blood from going back inside the ventricle during diastole will be directly transferred to the stent/vessel wall interface. Therefore, the amount of radial force required to keep the self-expanding stent/valve in contact with the vessel wall and not sliding will be much higher than in stents that do not have valves inside of them. Moreover, a self-expanding stent without sufficient radial force will end up dilating and contracting with each heartbeat, thereby distorting the valve, affecting its function and possibly causing it to migrate and dislodge completely. Simply increasing strut thickness of the self-expanding stent is not a good solution as it increases profile and/or a risk of plastic deformation of the self-expanding stent.

In view of drawbacks associated with previously known techniques for endovascularly replacing a heart valve, it would be desirable to provide methods and apparatus that overcome those drawbacks.

SUMMARY OF THE INVENTION

The invention includes methods of and apparatus for endovascularly replacing a heart valve of a patient. One aspect of the invention provides a method including the steps of endovascularly delivering a replacement valve and an expandable anchor to a vicinity of the heart valve in an unexpanded configuration; and applying an external non-hydraulically expanding or non-pneumatically expanding actuation force on the anchor through a plurality of anchor actuation elements to change the shape of the anchor, such as by applying a proximally and/or distally directed force on the anchor through anchor actuation elements to change the shape of the anchor. The anchor may be locked in its expanded configuration.

Another aspect of the invention provides an apparatus for endovascularly replacing a patient's heart valve, including: a replacement valve; an anchor; and a deployment tool comprising a plurality of anchor actuation elements adapted to apply a non-hydraulically expanding or non-pneumatically expanding actuation force on the anchor to reshape the anchor. An anchor lock may be provided to lock the anchor in a deployed configuration, and there may also be a lock prevention element actuatable from outside the patient. Optionally, the anchor lock may be reversible.

Other aspects of the invention include methods and apparatuses for endovascularly, percutaneously and/or endoscopically delivering and deploying expandable devices in a patient and optionally detaching a deployment tool from the device.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the apparatus in a collapsed delivery configuration within a delivery system. FIG. 1B illustrates the apparatus in an expanded configuration partially deployed from the delivery system.

FIGS. 15A and 15B show an alternative variation of the post having a lock alignment feature.

FIGS. 16A and 16B show a variation of the post having an alternative lock alignment feature.

FIG. 17 shows a variation of the post having an expansile element.

FIG. 18 shows a variation of the post with an alternative expansile element.

FIGS. 21A-21C show a variation of the post, actuator and release actuator that form an alternative releasable attachment mechanism.

FIGS. 23A-23C show yet another variation of the releasable attachment mechanism.

FIGS. 26A-26C show a variation of the actuator, lock actuator and release actuator.

FIGS. 31A-31C show actuation and release of a variation of the anchor lock element.

FIGS. 33A-33D show actuation of a variation of the anchor lock element that may be formed from a cut tube.

FIGS. 34A-34F show a variation of the post having an unlock actuator.

FIGS. 35A and 35B show another buckle variation of the anchor lock element.

FIGS. 40A-40C show a tubular variation of the ratcheting lock element.

FIGS. 41A-41C show a variation of the anchor lock element of FIG. 40.

FIGS. 42A and 42B show a variation of the apparatus of FIG. 41 comprising a lock alignment feature.

FIGS. 43A-43F show a method of actuating and adjusting the ratcheting lock of the apparatus of FIG. 41.

FIGS. 45A-45C show detail views of the releasable attachment mechanism of the actuator of FIG. 44.

FIGS. 46A-46C show a variation of the releasable attachment mechanism of FIG. 45.

FIGS. 49A-49N show variations of a release actuator used in conjunction with the releasable attachment mechanism of FIG. 45.

DETAILED DESCRIPTION OF THE INVENTION

The present invention relates to apparatus and methods for endovascularly delivering and deploying a prosthesis, e.g., an aortic prosthesis, within and/or across a patient's native heart valve, referred to hereinafter as replacing the patient's heart valve. A delivery system and/or deployment tool is provided including a sheath assembly and a guidewire for placing the prosthetic apparatus endovascularly within the patient and a user control allowing manipulation of the prosthetic apparatus from external to the patient through the application of a non-hydraulically expanding or non-pneumatically expanding force on the anchor. A hydraulically or pneumatically expanding force would be, for example, a force applied to the anchor by a balloon expanded within the anchor. In certain embodiments, the application of a non-hydraulically expanding or non-pneumatically expanding force could include the use of a hydraulic component transmitting a proximally or distally directed force on an anchor.

The apparatus includes an anchor and a replacement valve. The anchor includes an expandable anchor such as a braid. In preferred embodiments, the expandable braid includes closed edges, but the edges may alternatively be open. The replacement valve is adapted to be secured within the anchor, and as such, be delivered endovascularly to the patient's heart to replace one of the patient's native heart valves. More preferably, the apparatus and methods of the present invention contemplate replacement of the patient's aortic valve.

Figure 1A:
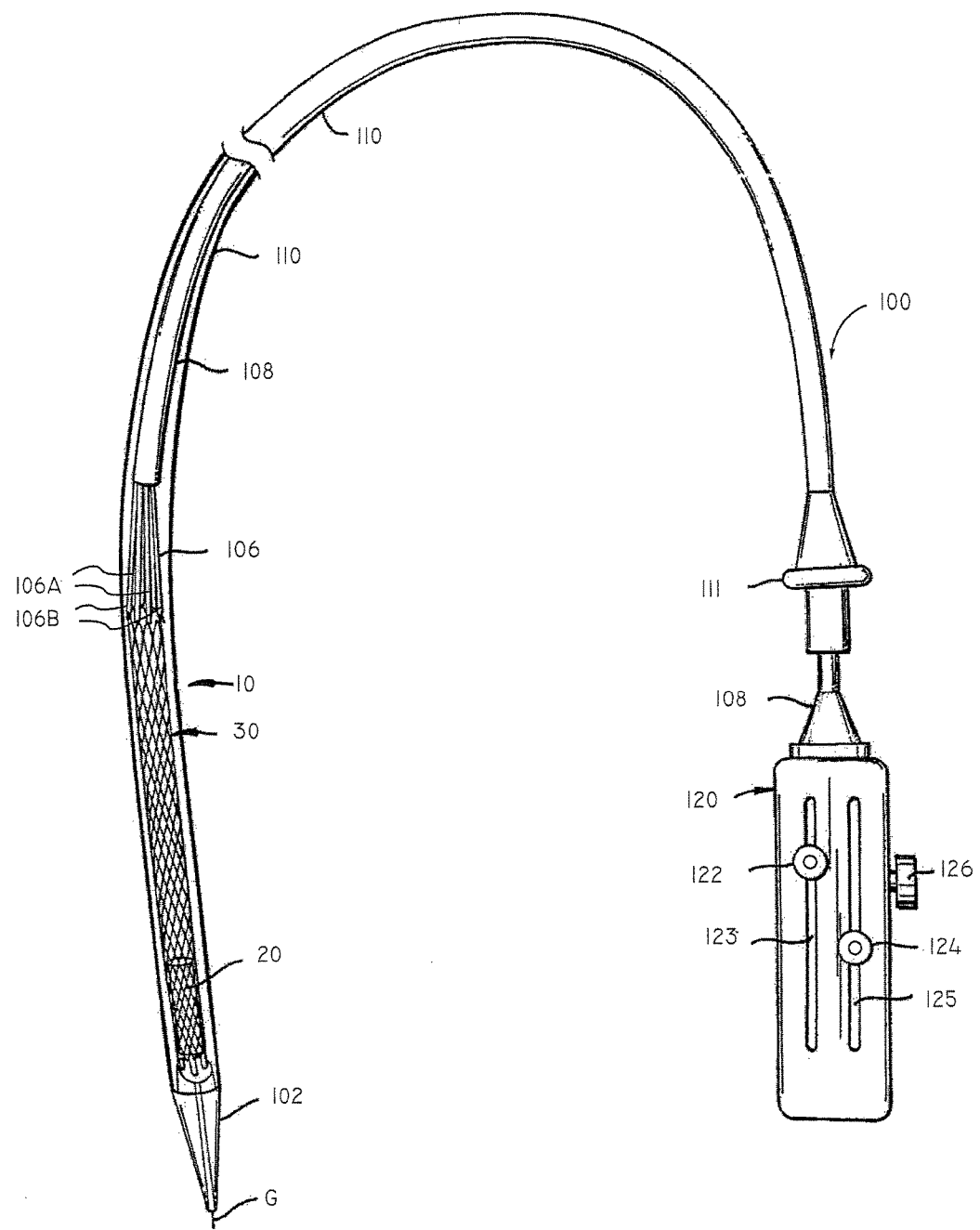
FIGS. 1A and 1B show replacement valve apparatus in accordance with the present invention.
Figures 1B, 2A:
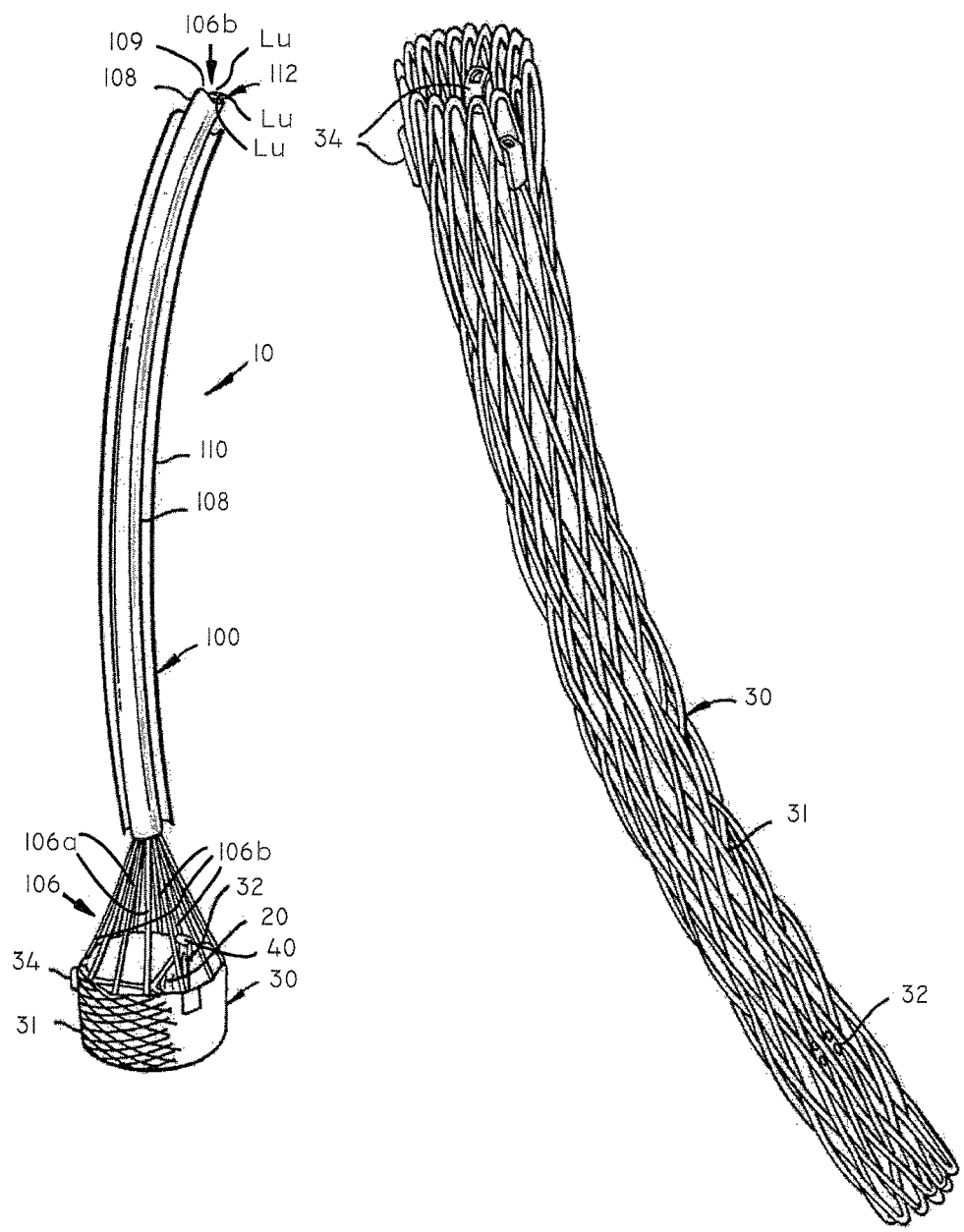
FIGS. 2A-2F show an anchor of the apparatus of FIG. 1 in the collapsed delivery configuration and the expanded deployed configuration, as well as the full apparatus in the deployed configuration, and optional locking mechanisms for use with the apparatus.

FIGS. 1A and 1B illustrate one embodiment of a delivery system/deployment tool and apparatus in accordance with the present invention. As seen in FIG. 1A, apparatus 10 may be collapsed for delivery within delivery system/deployment tool 100. Delivery system 100 includes guidewire G, nosecone 102, anchor actuation elements 106, multi-lumen shaft or catheter 108 having optional central lumen 109 and a plurality of circumferentially disposed lumens Lu, external sheath 110 having optional proximal handle 111, and control handle 120. Nosecone 102 may, for example, be manipulated via a shaft extending through central lumen 109 of multi-lumen catheter 108.

Anchor actuation elements 106 preferably comprise both proximal anchor actuation elements and distal anchor actuation elements. The proximal anchor actuation elements may, for example, comprise actuators 106a that are releasably coupled to a proximal region of anchor 30 of apparatus 10 via releasable attachment mechanisms for manipulating a proximal region of apparatus 10. The distal anchor actuation elements may comprise actuators 106b that are releasably coupled to a distal region of anchor 30 via releasable attachment mechanisms for manipulating the distal region of apparatus 10. In some embodiments, the distal anchor actuation elements may comprise posts or anchor attachment elements 32 of anchor 30 and the releasable attachment mechanisms connecting actuators 106b to posts 32. In an alternative configuration, the proximal anchor actuation elements may be releasably coupled to a proximal region of apparatus 10 through posts and releasable attachment mechanisms for manipulation of a proximal region of the apparatus, while the distal anchor actuation elements may connect to a distal region of anchor 30 via releasable attachment mechanisms to manipulate a distal region of the apparatus. As another alternative, both proximal and distal anchor actuation element may connect to anchor 30 via releasable attachment mechanisms.

In the embodiment shown in FIG. 1, actuators 106a may, for example, include stiff finger elements extending from a distal region of multi-lumen shaft 108, while actuators 106b may include control wires (e.g., stands of suture, or metal or polymer wires) which pass through one or more lumens Lu of shaft 108. Release actuators 112 for the releasable attachment mechanisms for both sets of actuators also may pass through one or more lumens Lu of shaft 108. The release actuators may comprise, for example, control wires (e.g., strands of suture, or metal or polymer wires), covers, mandrels, elongated elements, friction surfaces, wrap portions, interference shapes, etc. The release actuators preferably are movable relative to anchor actuation elements 106, e.g., via control handle 120.

Control handle 120 is coupled to multi-lumen shaft 108. Knob 122 disposed in slot 123 may actuate release actuators 112 that couple actuators 106a of anchor actuation elements 106 to apparatus 10. Likewise, knob 124 disposed in slot 125 may actuate release actuators 112 that couple actuators 106b of anchor actuation elements 106 to posts 32 of anchor 30 of apparatus 10. Handle 120 also comprises knob 126 for, e.g., manipulating the actuators 106b to control movement of the distal region of apparatus 10 relative to its proximal region. Conversely, controlled movement of the proximal region of apparatus 10 relative to its distal region may be achieved by holding knob 126 stationary while advancing or retracting handle 120. Knob 126 optionally may move actuators 106b in unison with their concomitant release actuators 112.

Apparatus 10 comprises anchor 30 and replacement valve 20. Anchor 30 preferably comprises a braid. Such braid can have closed ends at either or both its ends. Replacement valve 20 is preferably coupled to the anchor along posts 32, e.g., along a valve attachment structure, such as a tab and/or a plurality of holes. Posts 32, therefore, may function as valve supports and may be adapted to support the replacement valve within the anchor. In the embodiment shown, there are three posts, corresponding to the valve's three commissural attachment points. The posts can be attached to the braid portion of anchor 30. The posts can be attached to the braid's distal end, as shown in FIG. 2A, central region, or proximal end. Replacement valve 20 can be composed of a synthetic material and/or may be derived from animal tissue. Replacement valve 20 is preferably configured to be secured within anchor 30.

Figure 2B:
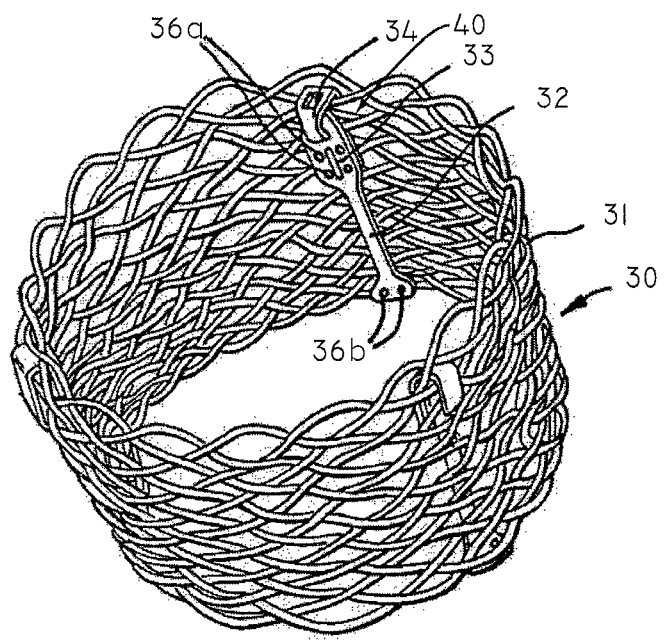
Figure 2C:
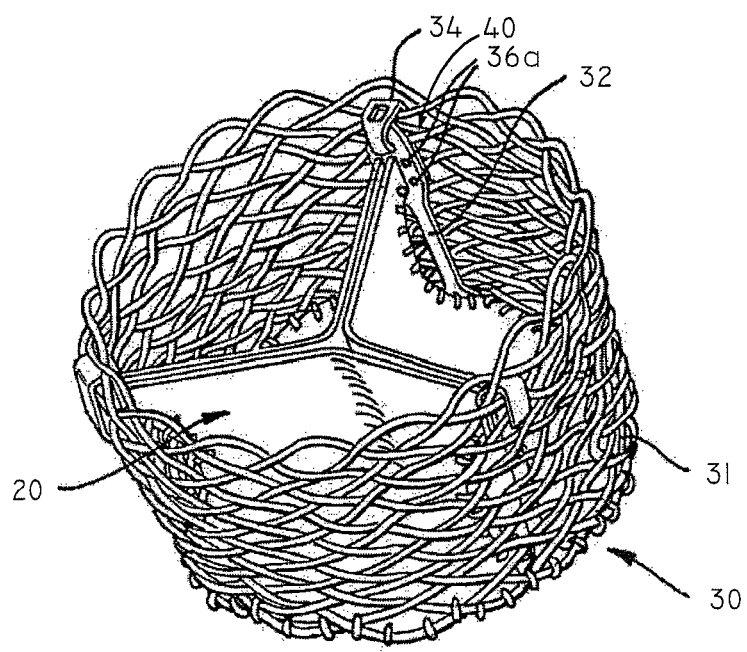

Anchor 30 comprises a plurality of anchor lock elements 34, e.g., buckles 34, attached to its proximal region, one for each post 32. Posts 32 may comprise a lock element that forms a two-part locking mechanism with anchor lock elements 34 for maintaining anchor 30 in a deployed or expanded configuration (e.g., as illustrated in FIGS. 1B, 2B and 2C).

In this embodiment, anchor 30 is formed from a collapsible and expandable wire braid. Anchor braid 30 is preferably self-expanding and is preferably formed from a material such as Nitinol, cobalt-chromium steel or stainless steel wire using one or more strands of wire. Delivery and deployment of braided anchor 30 is similar to the delivery and deployment of the anchors described in U.S. patent application Ser. No. 10/746,120. Specifically, in one embodiment described below, during deployment braided anchor 30 is actively foreshortened by proximally retracting the actuators 106b relative to the actuators 106a to expand and lock the anchor in place. In some embodiments, foreshortening may expand anchor 30 to a radially symmetrical, bilaterally symmetrical, or asymmetrical expanded shape. The foreshortening step can include expanding a first region of the anchor to a first diameter and a second region of the anchor to a second diameter larger than the first diameter. A third region may also be expanded to a diameter larger than the first diameter. The expansion of various regions of the anchor (e.g., the distal region) can be especially useful in locating the aortic valve and centering the anchor within it. Preferably, the secured anchor does not interfere with the mitral valve or the ostia. In some embodiments, the anchor is allowed to self-expand prior to the foreshortening step.

As seen in FIG. 1, after endovascular delivery through sheath 110 to the vicinity of the patient's native valve (such as the aortic valve), apparatus 10 may be expanded from the collapsed delivery configuration of FIG. 1A to the expanded deployed configuration of FIG. 1B using delivery system/deployment tool 100. To deploy apparatus 10, external sheath 110 may be retracted relative to apparatus 10 by proximally retracting sheath handle 111 relative to control handle 120. Sheath 110 is thereby removed from the exterior of apparatus 10, permitting the anchor 30 to self-expand. For example, if anchor braid 30 is composed of a shape memory material, it may self-expand to or toward its "at-rest" configuration. This at-rest configuration of the braid can be, for example its expanded configuration, a collapsed configuration, or a partially expanded configuration between the collapsed configuration and the expanded configuration, or some combination. In preferred embodiments, the anchor's at-rest configuration is between the collapsed configuration and the expanded configuration. Depending on the at-rest diameter of the braid and the diameter of the patient's anatomy at the chosen deployment location, the anchor may or may not self-expand to come into contact with the diameter of the patient's anatomy at that location.

In its collapsed configuration, anchor 30 preferably has a collapsed delivery diameter between about 3 to 30 Fr, or more preferably 6 to 28 Fr, or more preferably 12 to 24 Fr. In some embodiments, anchor 30 in its collapsed configuration will have a length ranging from about 5 to about 170 mm, more preferably from about 10 to about 160 mm, more preferably from about 15 to about 150 mm, more preferably from about 20 to about 140 mm, or more preferably from about 25 mm to about 130 mm.

Similarly, in its expanded configuration, anchor 30 preferable has a diameter ranging between about 10 to about 36 mm, or more preferably from about 24 to about 33 mm, or more preferably from about 24 to about 30 mm. In some embodiments, anchor 30 in its expanded configuration will have a length ranging from about 1 to about 50 mm, more preferably from about 2 to about 40 mm, more preferably from about 5 to about 30 mm, or more preferably from about 7 to about 20 mm.

Overall, the ratio of deployed to collapsed/sheathed lengths is preferably between about 0.05 and 0.5, more preferably about 0.1 to 0.35, or more preferably about 0.15 to 0.25. In any of the embodiments herein, anchor 30 in its expanded configuration preferably has a radial crush strength that maintains the anchor substantially un-deformed in response to a pressure of up to about 0.5 atm directed substantially radially inward toward the central axis, or more preferably up to about 2 atm directed substantially radially inward toward the central axis. In addition, in any of the embodiments herein, the anchor preferably has an axial spring constant of between about 10 to 250 g/cm, more preferably between about 20 to 200 g/cm, or more preferably between about 40 to 160 g/cm. In addition, in any of the embodiments herein, the anchor is preferably adapted to support the replacement valve at the anchor site in response to a differential pressure of up to about 120 mm Hg, more preferably up to about 240 mm Hg, or more preferably up to about 320 mm Hg.

These parameters are not intended to be limiting. Additional parameters within the scope of the present invention will be apparent to those of skill in the art.

As seen in FIG. 1B, anchor 30 may be expanded to a fully deployed configuration from a partial deployed configuration (e.g., self-expanded configuration) by actively foreshortening anchor 30 during endovascular deployment. In some embodiments, foreshortening of the apparatus involves applying a distally directed force on the proximal end of the anchor by one or more anchor actuation elements to move the proximal end of the anchor distally while maintaining the position of the distal end of the anchor. For example, the proximal region of anchor 30 may be pushed distally by certain anchor actuation elements 106, e.g., actuators 106a. Alternatively, foreshortening of the apparatus involves applying a proximally directed force on the distal end of the anchor by one or more anchor actuation elements to move the distal end of the anchor proximally while maintaining the position of the proximal end of the anchor. For example, the distal region of anchor 30 may be pulled proximally via a proximally directed force applied by post actuation elements 106b, this force opposed by anchor actuators 106a.

Anchor actuation elements 106 preferably are adapted to expand radially as the anchor expands radially and to contract radially as the anchor contracts radially. Furthermore, proximally or distally directed forces by the anchor actuation elements on one end of the anchor do not diametrically constrain the opposite end of the anchor. In addition, when a proximally or distally directed force is applied on the anchor by the anchor actuation elements, it is preferably applied without passing any portion of a deployment system through a center opening of the replacement valve. This arrangement enables the replacement valve to operate during deployment and before removal of the deployment system.

The distal anchor actuation elements may include, for example, actuators 106b and/or release actuators 112 that are controlled, e.g., by control knobs 124 and 126 of control handle 120. Similarly, the proximal regions of anchor 30 may be pushed distally via proximal anchor actuation elements, e.g., actuators 106a, at the proximal region of the anchor. The proximal anchor actuation elements facilitate application of a distally directed force to the proximal end of anchor 30 to move or constrain the proximal end of the anchor distally and are controlled through motion of shaft 108 relative to the distal anchor actuation elements. Control knob 122 of control handle 120 may control release actuators 112 for releasing the proximal anchor actuation elements from the braid. The proximal anchor actuation elements may be further adapted to expand as the proximal end of the anchor expands radially during application of a distally directed force on the proximal end of the anchor. Preferably, the proximal anchor actuation elements apply a distally directed force on the proximal end of the anchor system through a plurality of actuators 106a in order to expand the braid of anchor 30. Such braid expansion optionally may be assisted via inflation of a balloon catheter (see FIGS. 12 and 13) reversibly disposed within apparatus 10, as described in U.S. patent application Ser. No. 10/746,120.

In the fully deployed configuration, lock elements of posts 32 and anchor lock elements or buckles 34 of anchor 30 may be used to lock and maintain the anchor in the deployed configuration. Apparatus 10 may be repositioned or retrieved from the patient until the lock elements of posts 32 have been interlocked with anchor lock elements 34 of anchor 30 to form lock 40. In one embodiment, actuators 106b and attendant release actuators 112 comprise control wires attached to posts 32 that are threaded through buckles 34 so that the proximally directed force exerted on posts 32 by the control wires during deployment pulls a lock element of posts 32 toward and through buckles 34 to form lock 40. In this manner, the control wires may act as both anchor actuators and lock actuators.

Such lock optionally may be selectively reversible to allow for repositioning and/or retrieval of apparatus 10 during or post-deployment. When the lock is selectively reversible, the apparatus may be repositioned and/or retrieved as desired, i.e., even after actuation of lock 40.

Locks used herein may also include a plurality of levels of locking wherein each level of locking results in a different amount of expansion. For example, the anchor lock elements at the proximal end of the post can have multiple configurations for locking within the buckle wherein each configuration results in a different amount of anchor expansion (see, e.g., FIG. 2F). Such locking mechanisms may, for example, comprise ratchets having multiple lock locations. Furthermore, lock alignment features may be provided to facilitate alignment of the post and anchor lock elements, such as a hinge or an oversized width of the post or anchor lock elements. Furtherstill, lock prevention mechanisms may be provided to preclude locking until desired by a medical practitioner.

When apparatus 10 is placed across a patient's diseased heart valve, anchor 30 may be used to displace the patient's native valve leaflets, and replacement valve 20 will thereafter serve in place of the native valve. After final positioning and expansion, apparatus 10 may be decoupled from delivery system 100 by decoupling the proximal and distal anchor actuation elements 106 from the apparatus via releasable attachment mechanisms, e.g., by decoupling proximal actuators 106a from braided anchor 30 and distal actuators 106b from posts 32 of the anchor via the releasable attachment mechanisms. Moving release actuators 112, e.g., using knobs 122 and 124 of handle 120, may, for example, actuate the releasable attachment mechanisms. Preferably, the releasable attachment mechanisms may be actuated by moving the release actuator(s) less than about 1 inch. After decoupling, delivery system/deployment tool 100 may be removed from the patient, thereby completing endovascular replacement of a patient's heart valve.

Prior to implantation of replacement valve apparatus described herein, it may be desirable to perform a valvuloplasty on the patient's diseased valve by inserting a balloon into the valve and expanding it using, e.g., saline mixed with a contrast agent. In addition to preparing the valve site for implant, fluoroscopic viewing of the valvuloplasty will help determine the appropriate size of replacement valve implant to use.

FIGS. 2A-2C show further details of anchor 30 of apparatus 10. FIG. 2A shows the apparatus in a collapsed configuration, such as for delivery within a sheath or other lumen or for retrieval and recapture into a sheath or other lumen. FIGS. 2B and 2C show the anchor and valve in an expanded and locked configuration.

As shown in FIG. 2B, anchor 30 illustratively has three posts and three buckles. As seen in FIG. 2C, the three leaflets of replacement valve 20 may be coupled to the three posts 32 along valve support structures. Thus, posts 32 act as valve supports. The posts, unlike the braid, do not collapse or expand. In some embodiments, a post 32 has one or more proximal slots 33, at least one proximal hole 36a and at least one distal hole 36b. Leaflet tissue may, for example, be passed through slot 33 and sutured in place via suture routed through one or more proximal holes 36a. In this manner, slot(s) 33 and hole(s) 36a may form a valve support structure. Alternative valve support structures known in the art for fixing valve leaflets to posts may also be employed.

Posts 32 may be coupled to anchor braid 30 via one or more distal holes 36b. For example, anchor braid 30 may be woven through holes 36b, or a suture or wire may be routed through holes 36b and tied to the braid. Yet another proximal hole (not shown) in post 32 serves as an anchor lock element that interfaces with the anchor lock element provided by buckle 34 to form lock 40. Buckles 34 may likewise be attached to anchor braid 30 via weaving or suturing.

Figure 2D:
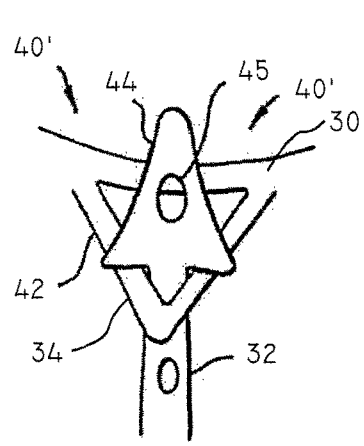
Figure 2E:
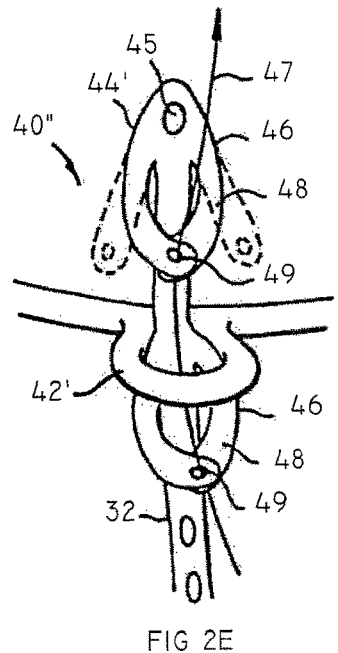
Figure 2F:
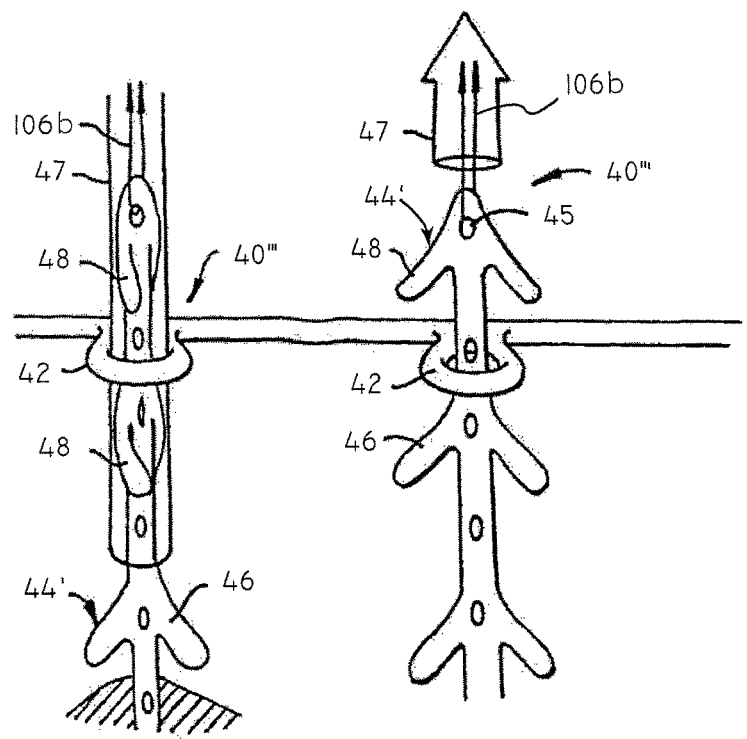

Alternative locks may be used to lock the anchor of the present invention in the foreshortened configuration, as shown, e.g., in FIGS. 2D-2F. Preferably, a lock of the present invention can have multiple locking options such that locking can confer a plurality of amounts of expansion. Furthermore, the locking option can be employed asymmetrically to confer non-cylindrical shapes to the anchor. In FIG. 2D, lock 40' comprises male lock element 44 disposed on post 32 and anchor lock element 34 disposed on braided anchor 30. Anchor lock element 34 illustratively comprises triangular protrusion or eyelet 42 of anchor 30. The triangular shape of female lock element 42 may facilitate mating of male lock element 44 with the female lock element without necessitating deformation of the male lock element. One or more holes 45 may be provided through post 32, e.g., for releasably attaching an actuator 106b to the post.

In FIG. 2E, lock 40" comprises alternative male lock element 44' having multiple in-line arrowheads 46 along posts 32. Each arrowhead comprises resiliently deformable appendages 48 to facilitate passage through female lock element 42', which illustratively comprises a rounded eyelet. Appendages 48 optionally comprise holes 49, such that releasable lock prevention mechanism 47, illustratively a control wire, may pass through the holes to constrain the appendages in the deformed configuration. To actuate lock 40", one or more arrowheads 46 of male lock element 44' are drawn through female lock element 42', e.g., via a post/lock actuator, and the lock prevention mechanism is removed from holes 49, thereby causing appendages 48 to resiliently expand and actuate lock 40".

Advantageously, providing multiple arrowheads 46 along posts 32 yields a ratchet that facilitates in-vivo determination of a degree of foreshortening and expansion imposed upon anchor 30. Furthermore, optionally constraining appendages 48 of arrowheads 46 via mechanism 47 prevents actuation of lock 40" (and thereby deployment of apparatus 10) even after male element 44' has been advanced through female element 42'. Only after a medical practitioner has removed lock prevention mechanism 47, which constrains appendages 48, is lock 40" fully engaged and is deployment no longer reversible.

Lock 40''' of FIG. 2F is similar to lock 40" of FIG. 2E, except that holes 49 on appendages 48 have been eliminated, and the lock prevention mechanism comprises overtube or cover 47. Overtube 47 constrains appendages 48 to prevent locking until a medical practitioner has determined that apparatus of the present invention has been foreshortened and positioned adequately at a treatment site. Lock 40''' may, for example, be actuated by applying a proximally-directed force to actuator 106b. Actuator 106b illustratively comprises a control wire releasably disposed through hole 45 in post 32. Lock prevention mechanism 47 then is withdrawn proximally relative to anchor 30, which causes the appendages to resiliently expand, thereby fully actuating lock 40'''.

Referring now to FIG. 3 in conjunction with FIGS. 1 and 2, a method of endovascularly replacing a patient's diseased aortic valve with apparatus 10 and delivery system/deployment tool 100 is described. As seen in FIG. 3A, sheath 110 of delivery system 100, having apparatus 10 disposed therein, is endovascularly advanced over guidewire G, preferably in a retrograde fashion (although an antegrade or hybrid approach alternatively may be used), through a patient's aorta A to the patient's diseased aortic valve AV. Nosecone 102 precedes sheath 110 in a known manner. In FIG. 3B, sheath 110 is positioned such that its distal region is disposed within left ventricle LV of the patient's heart H.

Figure 3A:
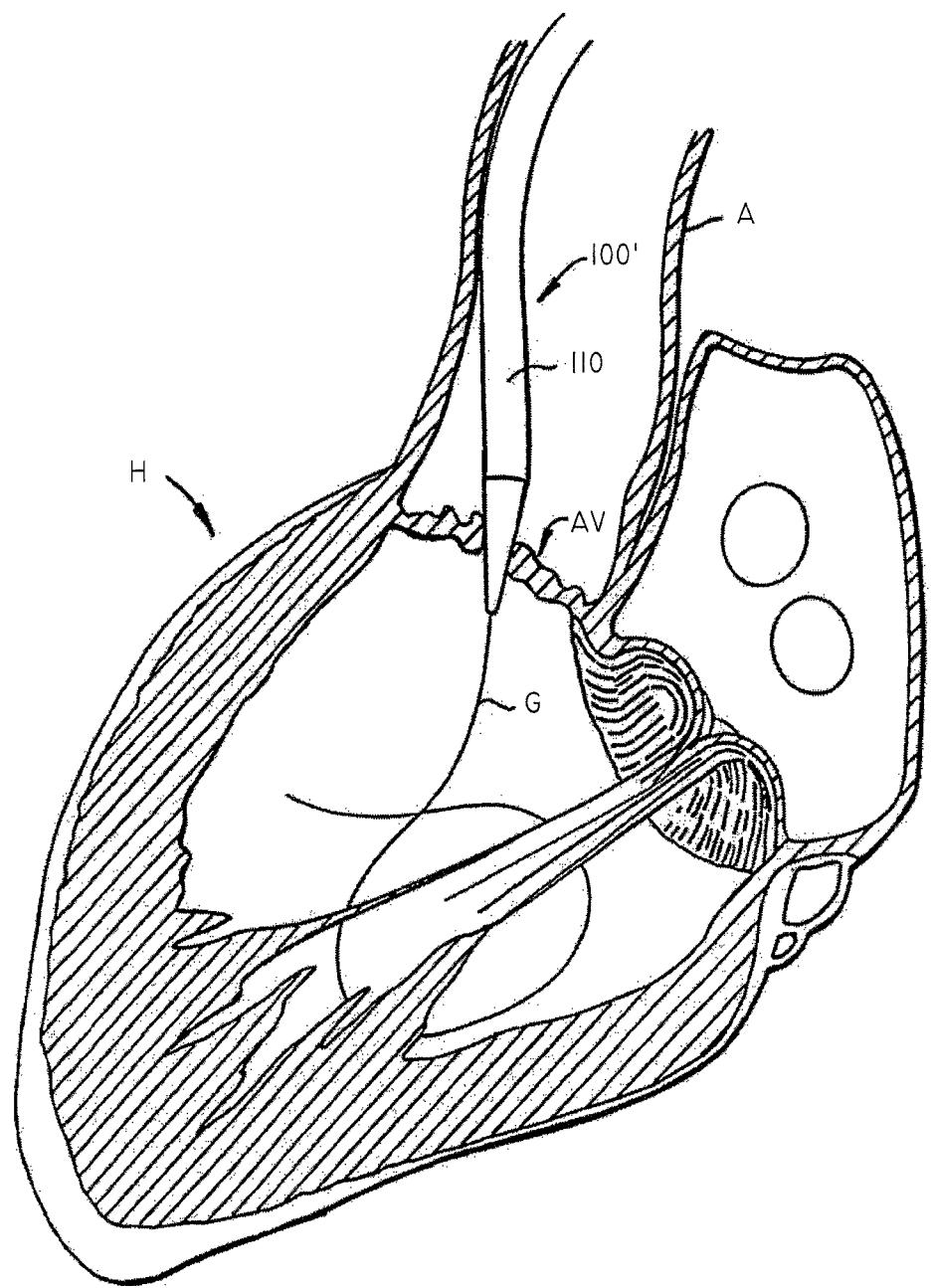
FIGS. 3A-3E show the use of a replacement heart valve and anchor to replace an aortic valve.
Figure 3B:
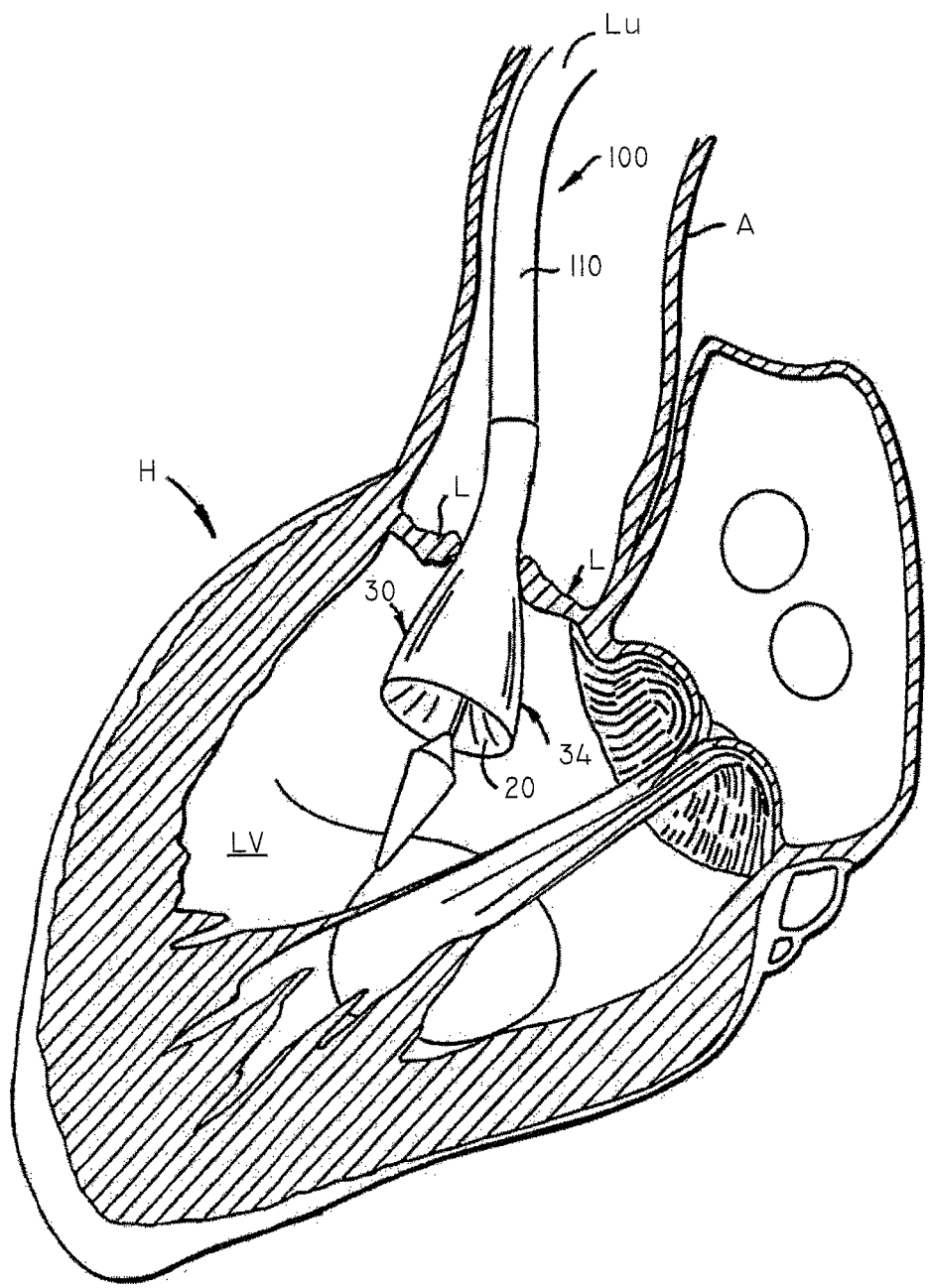
Figure 3C:
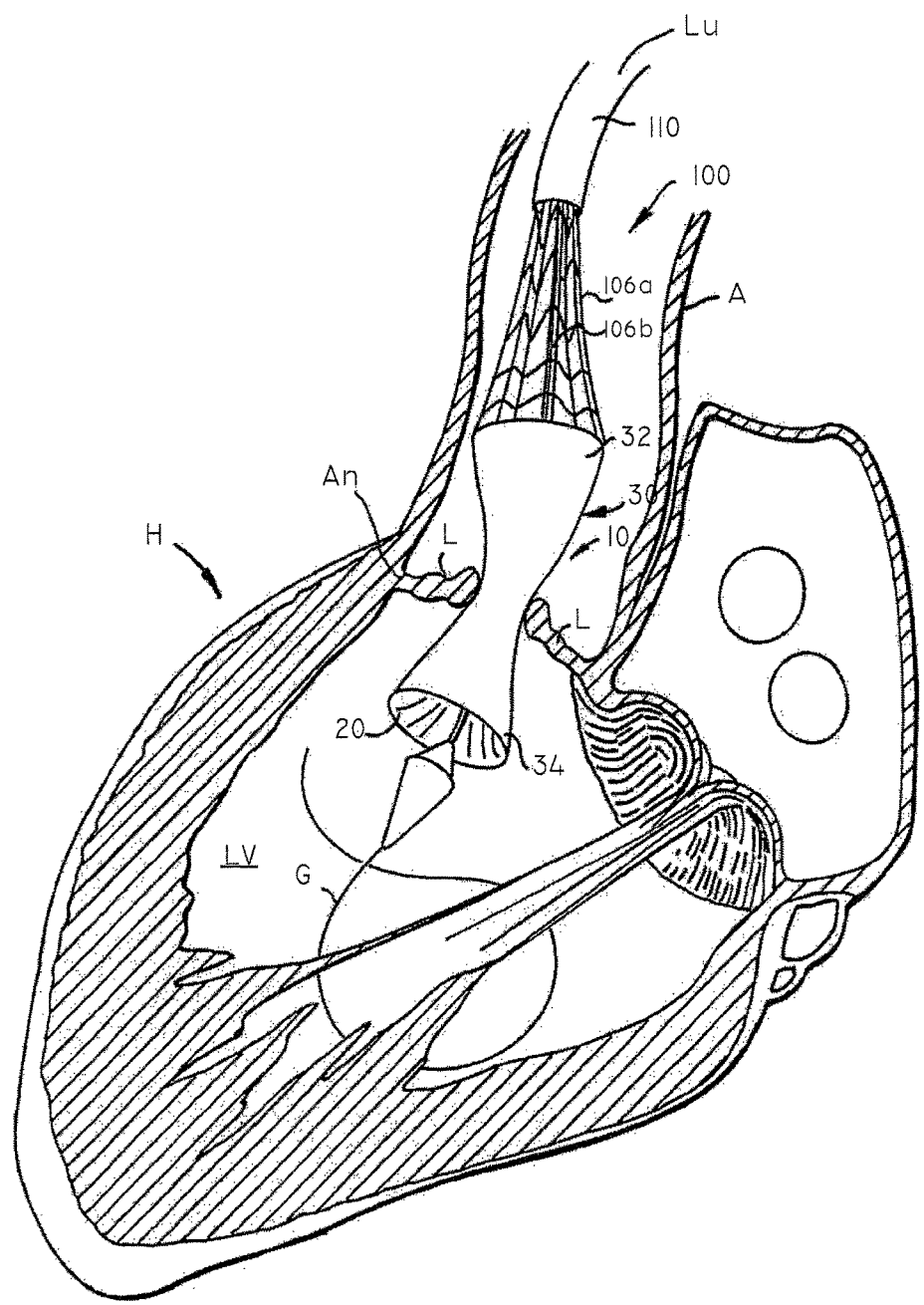

Apparatus 10 is deployed from lumen Lu of sheath 110, for example, under fluoroscopic guidance by proximally retracting proximal handle 111 of sheath 110 relative to shaft 108, such that anchor 30 of apparatus 10 dynamically self-expands to the partially deployed configuration of FIG. 3C. Advantageously, apparatus 10 may be retracted within lumen Lu of sheath 110 by retracting shaft 108 relative to the sheath, and thereby retracting actuators 106a coupled to anchor 30 relative to sheath 110. In this manner, anchor 30 may be retrieved even after the anchor has dynamically expanded to the partially deployed configuration, for example, to abort the procedure or to reposition apparatus 10 or delivery system 100. As yet another advantage, apparatus 10 may be dynamically repositioned, in order to properly align the apparatus relative to anatomical landmarks, such as the patient's coronary ostia or the patient's native valve leaflets L. When properly aligned, a distal region of anchor 30 preferably is disposed distal of the leaflets, while a central region of the anchor is disposed across the leaflets and a proximal region is disposed proximal of the leaflets.

Figure 3D:
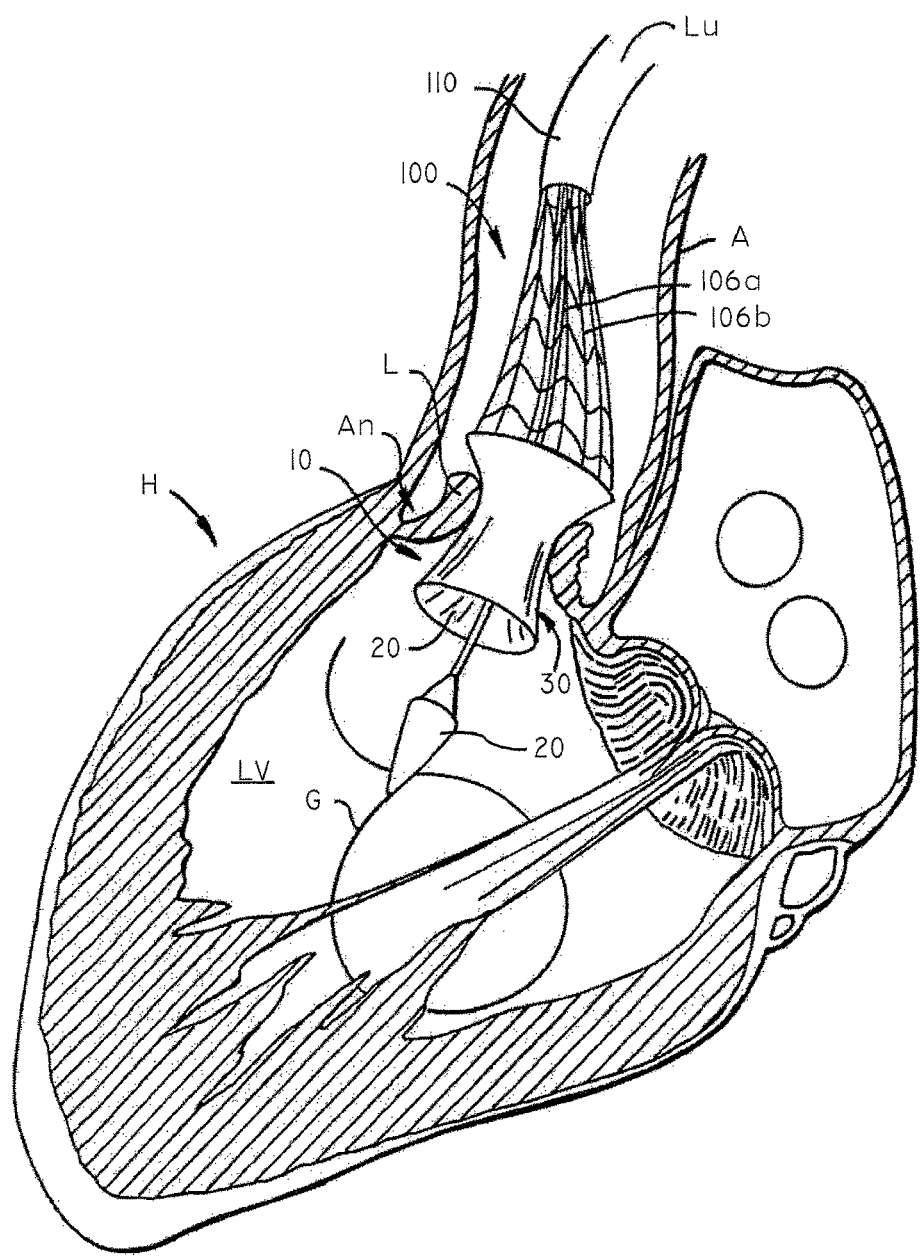

Once properly aligned, actuators 106b are proximally retracted relative to actuators 106a, e.g., via knob 126 of handle 120, to impose foreshortening upon anchor 30 and further expand apparatus 10 to the fully deployed configuration, as in FIG. 3D. Foreshortening increases the radial strength of anchor 30 to ensure prolonged patency of valve annulus An, as well as to provide a better seal for apparatus 10 that reduces paravalvular regurgitation. Lock 40 formed by engaging post lock elements 44 of posts 32 with anchor lock elements 34 of anchor 30 maintains imposed foreshortening. Replacement valve 20 is properly seated within anchor 30, and normal blood flow between left ventricle LV and aorta A is thereafter completely regulated by apparatus 10, although valve 20 is functional during deployment as well. Deployment of apparatus 10 advantageously is fully reversible until the locks have been actuated. Releasable lock prevention mechanisms may be provided to ensure that the locks are not actuated prematurely. Furthermore, the locks may be reversible, such that apparatus 10 may be retrieved or repositioned even after actuation of the locks.

Figure 3E:
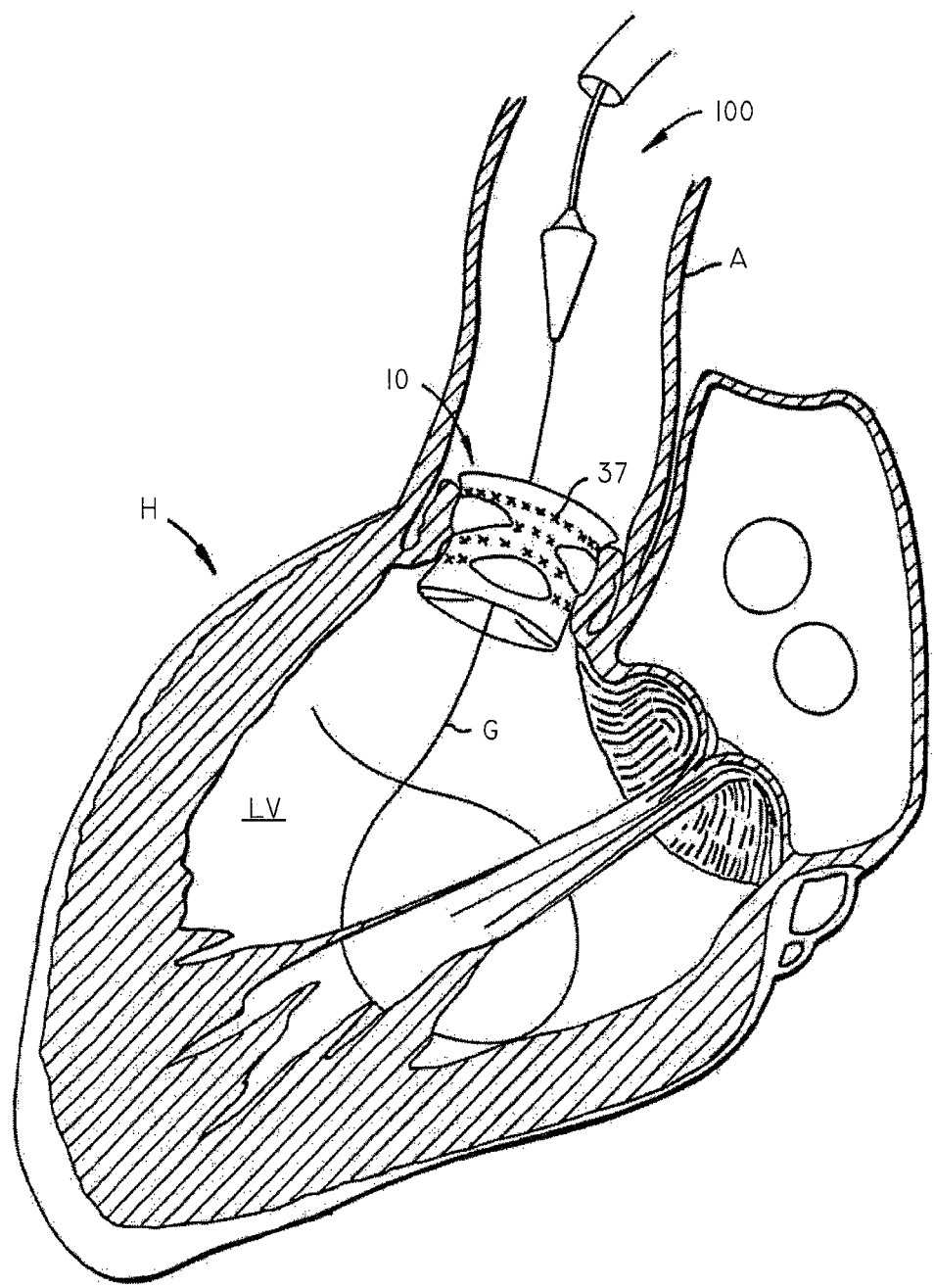

Once apparatus 10 is fully expanded and locked in the expanded configuration, actuators 106a are decoupled from anchor 30 by actuating releasable attachment mechanisms, e.g., by retracting release actuators 112 relative to the actuators 106a via knob 122 of handle 120. Likewise, actuators 106b are decoupled from posts 32 by actuating releasable attachment mechanisms, e.g., by retracting release actuators 112 relative to the actuators 106b via knob 124 of handle 120. As seen in FIG. 3E, delivery system 100 then may be removed from the patient, thereby completing deployment of apparatus 10. Optional barb elements 37 engage the patient's native valve leaflets, e.g. to preclude migration of the apparatus and/or to reduce paravalvular regurgitation.

Figure 4A:
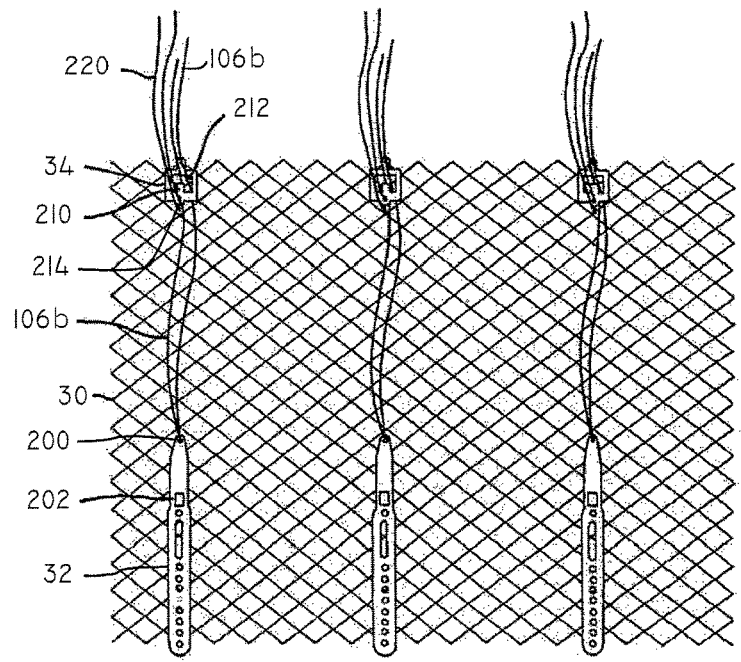
FIGS. 4A and 4B show an alternative anchor lock embodiment in an unlocked configuration.
Figure 4B:
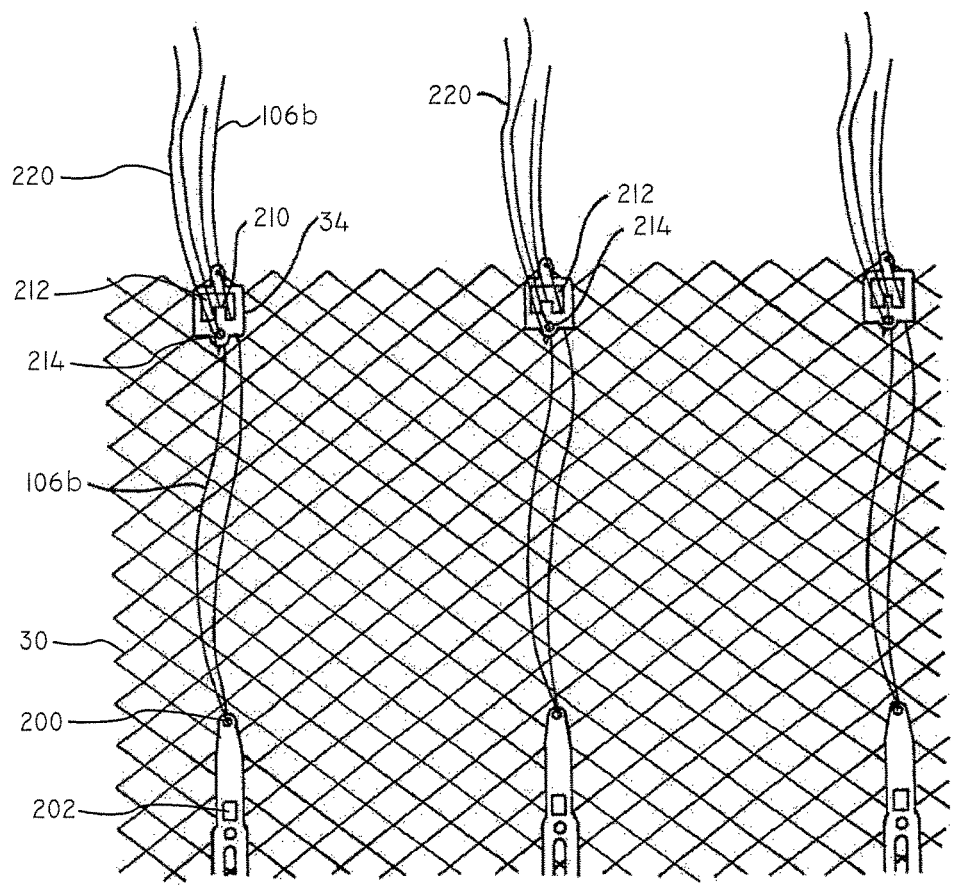
Figure 5A:
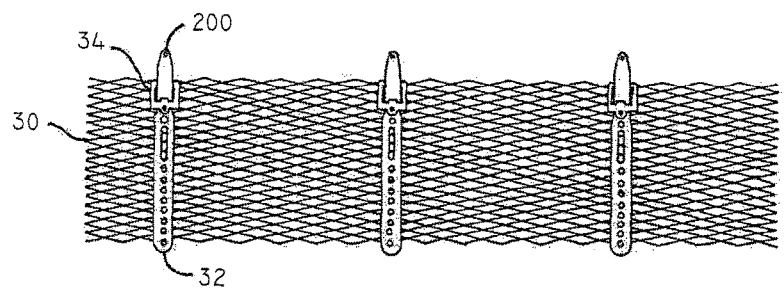
FIGS. 5A and 5B show the anchor lock of FIG. 4 in a locked configuration.
Figure 5B:
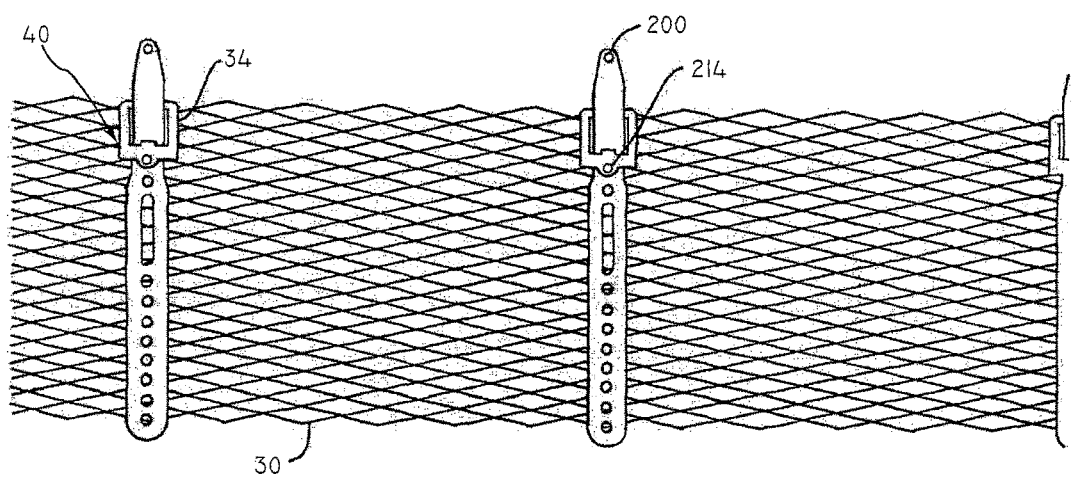

FIGS. 4 and 5 illustrate anchor lock mechanisms depicted in FIG. 4 in the locked configuration. FIGS. 4 and 5 should be viewed as if cylindrical anchor 30 has been cut open and laid flat. Posts 32 coupled to anchor 30 illustratively comprise actuator attachment elements 200 and lock elements 202, e.g., eyelets or holes formed through the posts. Anchor 30 comprises anchor lock elements 34, illustratively buckles, which are configured to mate with lock elements 202 of the posts. Posts 32 and buckles 34 may, for example, be connected to braided anchor 30 by inter-weaving the posts and the buckles into the braid of the anchor. Alternatively, the posts and/or buckles may be sutured, soldered, welded, connected with adhesive, etc., to the anchor. The commissures of previously described replacement valve 20 may be connected to posts 32 along all or a portion of their lengths.

Lock elements 202 of posts 32 mate with tabs 210 extending into holes 212 in anchor lock elements 34. To lock, actuators 106b, which releasably pass through actuator attachment elements 200 of posts 32 and holes 212 of anchor lock elements 34, are pulled proximally by anchor actuators 106b (illustratively control wires) with respect to the proximal end of braided anchor 30 to draw posts 32 through holes 212 so that tabs 210 engage lock elements 202 of posts 32. Also shown are unlocking actuators 220, illustratively control wires, which pass through anchor lock eyelets 214 in anchor lock elements 34. If needed, during the procedure, the user may pull on unlocking actuators 220, thereby reversing orientation of tabs 210, releasing the anchor and allowing for repositioning of the device or its removal from the patient. Only when final positioning as desired by the operating physician is achieved, would unlocking actuators 220, as well as actuators 106b, be removed from apparatus 10 and the patient.

Figure 6:
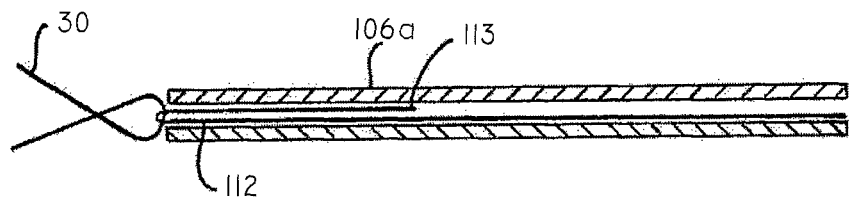
FIG. 6 shows an alternative anchor deployment tool attachment and release mechanism for use with the invention.
Figure 7:
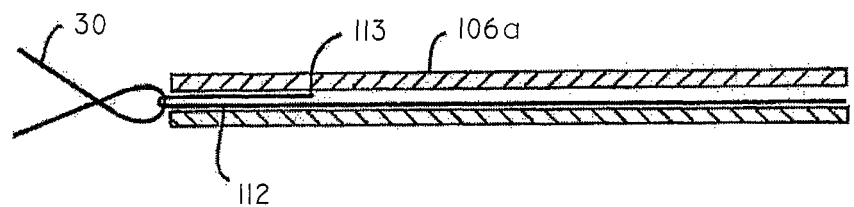
FIG. 7 shows the attachment and release mechanism of FIG. 6 in the process of being released.
Figure 8:
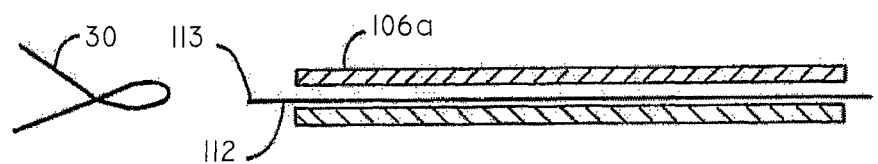
FIG. 8 shows the attachment and release mechanism of FIGS. 6 and 7 in a released condition.

Referring now to FIGS. 6-8, an alternative way of releasing the connection between the anchor (or post, etc.) and the anchor actuation elements is described. In FIG. 6, release actuator 112, illustratively a control wire, extends through actuator 106a from outside the patient, loops through the proximal region of braided anchor 30 and extends partially back into actuator 106a. The doubled up portion of release actuator 112 creates a force fit within actuator 106a that maintains the release actuator's position with respect to the actuator 106a when all release actuators 112 within actuators 106a are pulled proximally, e.g., when applying a proximally directed force on anchor 30. When a single release actuator 112 is pulled proximally, however, the frictional fit between that release actuator and the actuator 106a in which it is disposed is overcome, enabling the end 113 of release actuator 112 to pull free of actuator 106a, as shown in FIGS. 7 and 8, thereby releasing anchor 30. In an alternative embodiment, the doubled up portion of release actuator 112 may extend proximally to, e.g., control handle 120. In such an embodiment, expansion of anchor 30 may be achieved by proximally retracting both ends of the doubled up release actuator 112 via the control handle, while release of actuator 106a may be achieved by pulling on one end of release actuator 112.

Figure 9:
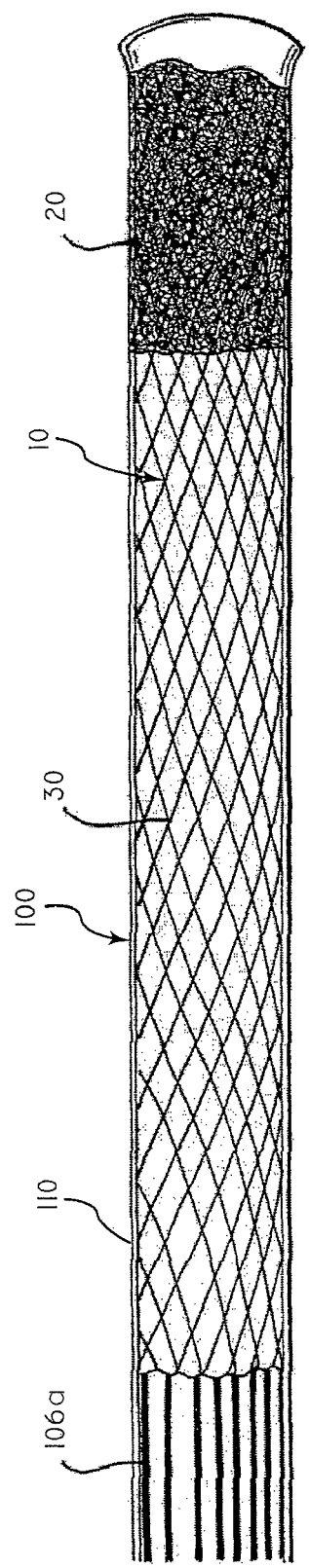
FIG. 9 shows an alternative embodiment of a replacement heart valve and anchor and a deployment tool according to the invention in an un-deployed configuration.
Figure 10:
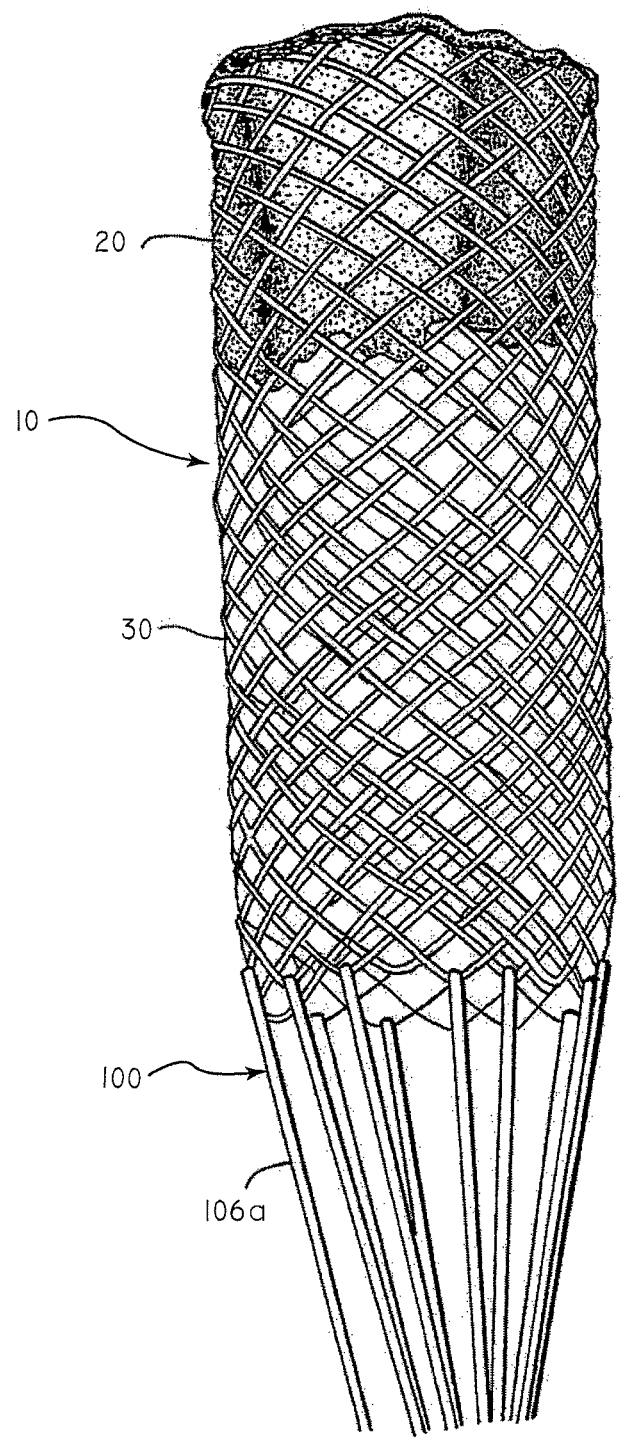
FIG. 10 shows the replacement heart valve and anchor of FIG. 9 in a partially deployed configuration.
Figure 11:
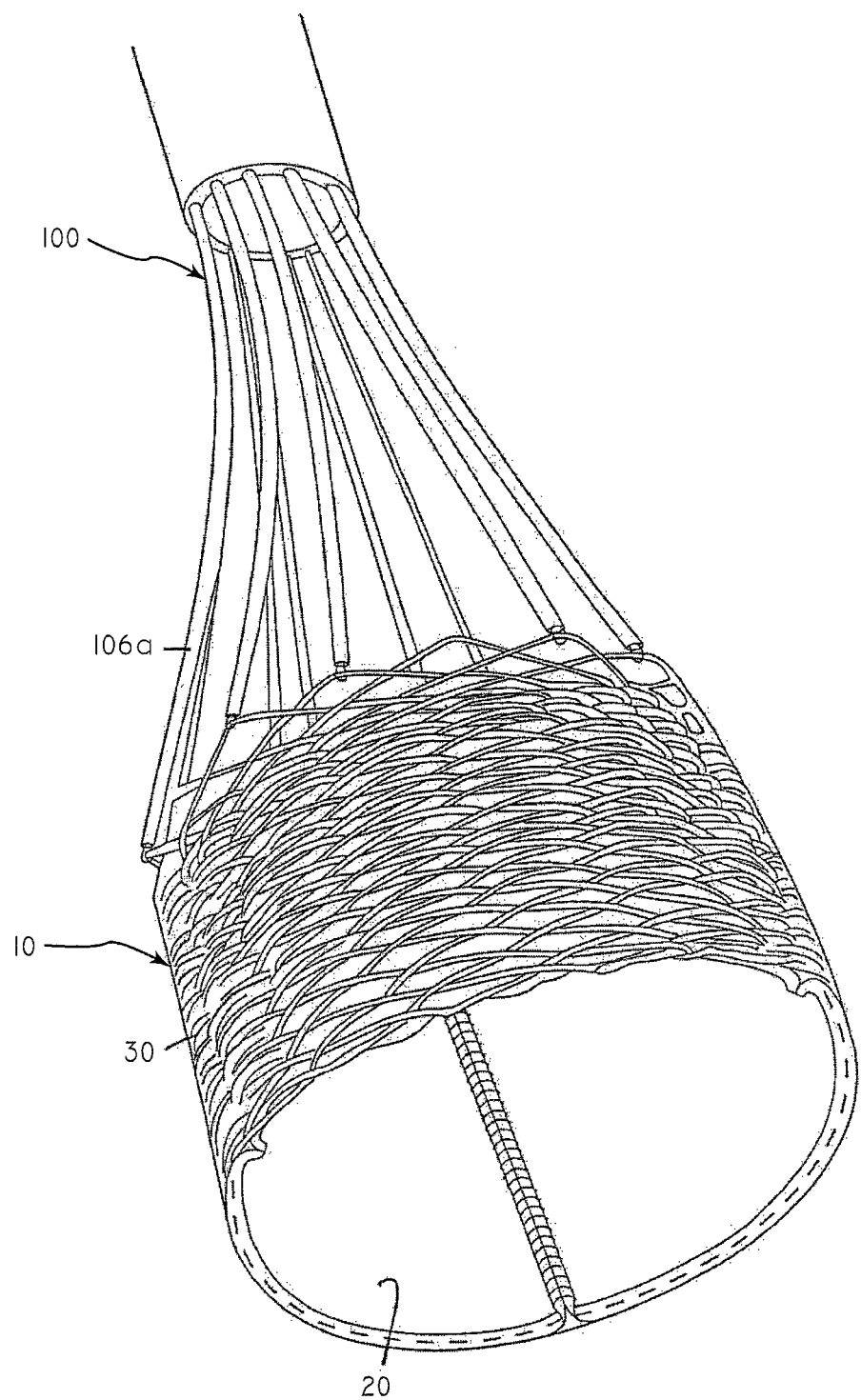
FIG. 11 shows the replacement heart valve and anchor of FIGS. 9 and 10 in a more fully deployed configuration but with the deployment tool still attached.

FIGS. 9-11 show additional views of apparatus 10. Anchor 30 is made of a metal braid, such as Nitinol or stainless steel. Replacement valve 20 is disposed within anchor 30. Anchor 30 is actuated in substantially the same way as described previously through the application of proximally and distally directed forces from distal anchor actuators (not shown) and actuators 106a.

Figure 12:
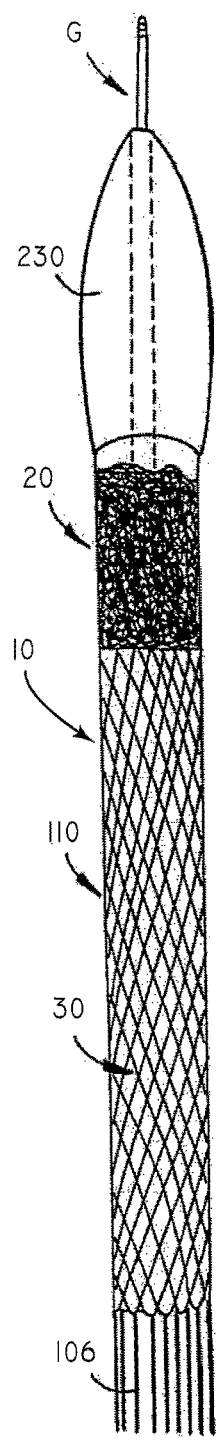
FIG. 12 shows yet another embodiment of the delivery and deployment apparatus of the invention in use with a replacement heart valve and anchor.
Figure 13:
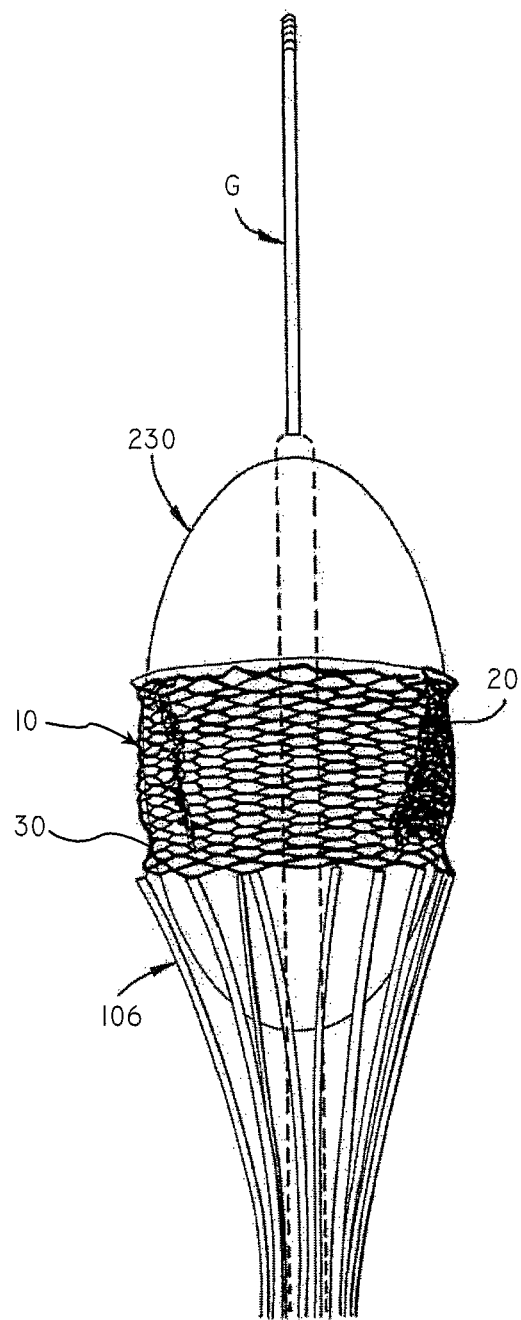
FIG. 13 shows the delivery and deployment apparatus of FIG. 12 in the process of deploying a replacement heart valve and anchor.

FIGS. 12 and 13 show another embodiment of the delivery and deployment apparatus of the invention. In this embodiment, the nosecone (e.g., element 102 of FIGS. 1A and 3) is replaced by angioplasty balloon catheter 230. Thus, angioplasty balloon catheter 230 precedes sheath 110 on guidewire G. When anchor 30 and valve 20 are expanded through the operation of anchor actuation elements 106 as described above, balloon catheter 230 is retracted proximally within the expanded anchor and valve and may be inflated to further expand the apparatus 10, as desired. Optionally, a separate balloon catheter or valvuloplasty catheter may be advanced within apparatus 10 after expansion thereof to achieve additional expansion of the apparatus.

Figure 14:
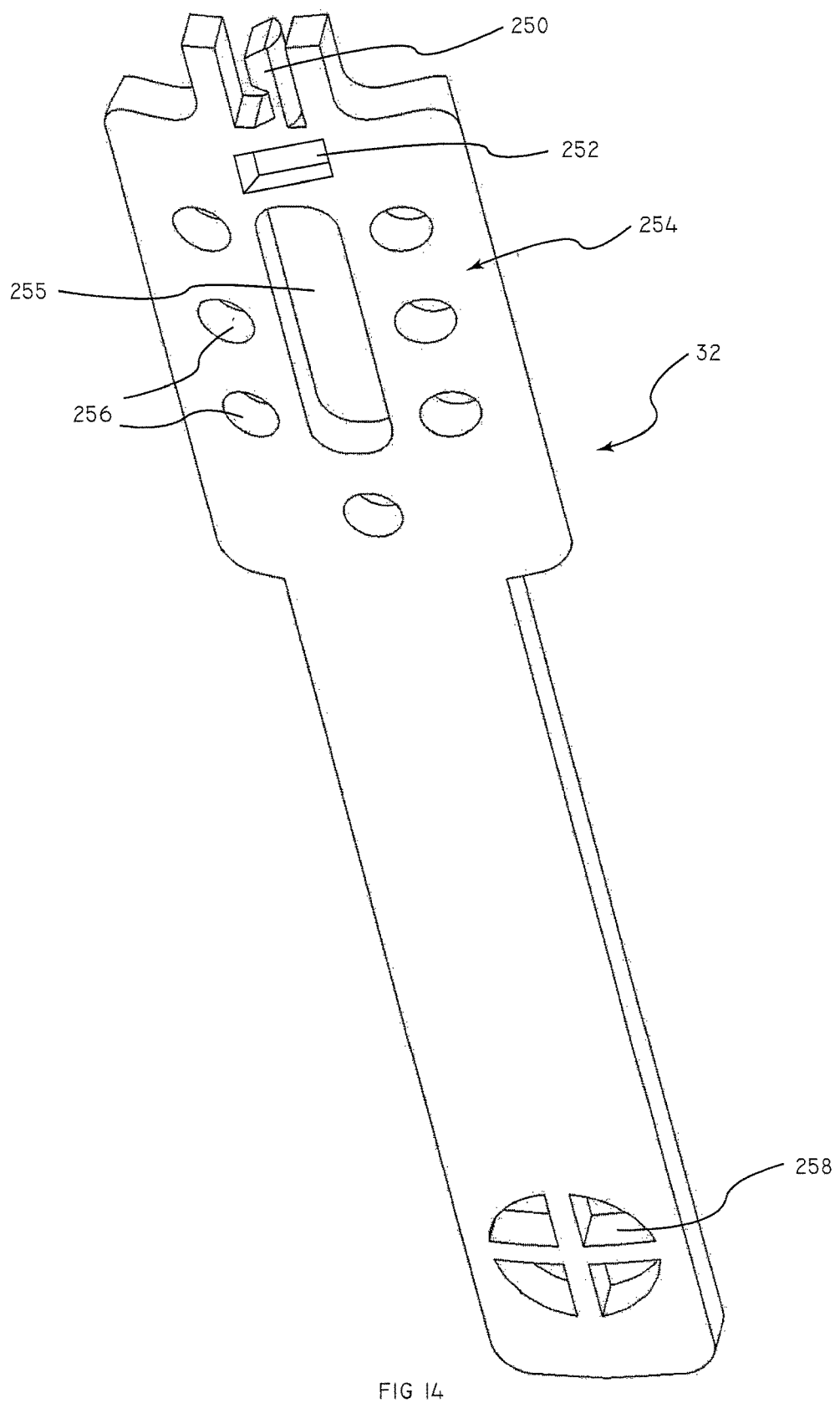
FIG. 14 shows a detail view of a variation of an anchor post.

Referring now to FIG. 14, a detail view of a variation of post 32 is described. In FIG. 14, post 32 illustratively comprises actuator attachment element 250 for attaching the post to an actuator 106b; post lock element 252, illustratively a slot, for interlocking post 32 with an anchor lock element 34; valve attachment structure 254, comprising slot 255 and a plurality of holes 256, for attaching replacement valve 20 to the post (a tab of the valve may be passed through slot 255, then sewn to the back of the post through holes 256); and braid attachment element 258 for attaching the post to a distal region of anchor 30. The braid of anchor 30 may, for example, be interwoven through braid attachment element 258. Post 32 may be fabricated from a variety of materials, e.g., metallic materials such as stainless steel, and may be laser cut, die cast, etc. In this variation of post 32, valve 20 is disposed distal of lock element 252. In alternative variations, the valve may be attached to the post proximal of the lock element or in-line with the lock element (i.e., neither proximal nor distal to the lock).

FIG. 15 provide an alternative variation of post 32. In FIG. 15, post 32 comprises lock element 260 having lock alignment feature 262, illustratively hinge 263. Hinge 263 allows lock element 260 to rotate from a position in line with post 32, as in FIG. 15A, to a position out of alignment with the post, as in FIG. 15B, thereby facilitating alignment with an anchor lock element 34. As shown, post 32 further comprises actuator attachment element 264, illustratively an eyelet, valve support structure 266 having slot 267 and a plurality of holes 268, and braid attachment element 269.

FIG. 16 illustrate an alternative variation of lock alignment feature 262 comprising spring 270. As with hinge 263, spring 270 facilitates alignment of post lock element 260 with an anchor lock element 34 by allowing the post lock element to rotate from a position in line with post 32, as in FIG. 16A, to a position out of alignment with the post, as in FIG. 16B. Spring 270 also applies a restoring force that urges post lock element 260 back into alignment with post 32. Furthermore, spring 270 may facilitate dynamic elongation of post 32 in response to axial tension. This elongation may facilitate axial lengthening of anchor 30 in response to radially inward compression applied to the anchor.

With reference to FIG. 17, another variation of post 32 is provided comprising expansion zone 280, which may, for example, comprise a laser cut feature along post 32. Expansion zone 280 facilitates dynamic elongation of post 32 in response to axial tension applied to the post, which facilitates axial lengthening of anchor 30 in response to radially inward compression applied to the anchor. FIG. 18 illustrates an alternative expansile element 290 comprising a curved wire or rod that may be elongated and straightened through application of axial tension to facilitate axial lengthening of the anchor in response to radially inward compression applied to the anchor (and thereby axial tension applied to post 32 via interaction between post lock element 260 and an anchor lock element 34).

Element 290 additionally or alternatively may serve as a lock alignment feature. In such a configuration, element 290 optionally may not be expansile. More generally, post 32 may comprise proximal and distal ends connected by a tensile member.

Figure 19:
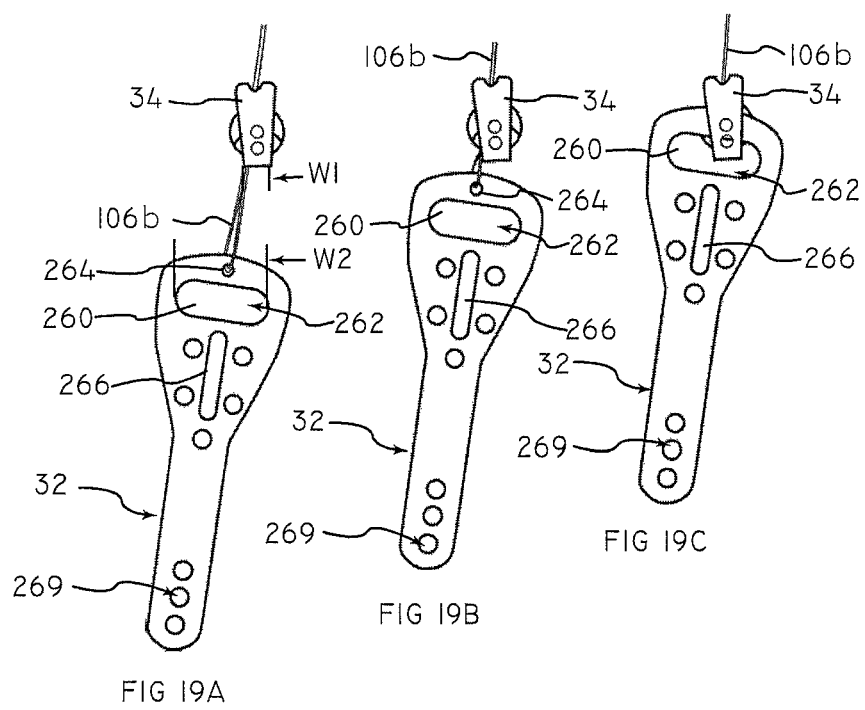
FIGS. 19A-19C show a variation of the post having an alternative lock alignment feature.

FIG. 19 illustrate another variation of post 32 having another alternative lock alignment feature 262. In FIG. 19, actuator 106b applies a proximally-directed force which brings post lock element 260 and anchor lock element 34 proximate to one another allowing the system to lock. Anchor lock element 34 defines a lock width $W_1$. In this embodiment, lock alignment feature 262 comprises post lock element lock area or width W2 that is substantially wider than the lock width $W_1$, for example, at least about twice as wide. This increased width enhances the probability of interlocking the post and anchor lock elements, even at sharply misaligned angles. In FIG. 19, post 32 and anchor lock element 34 are disposed at an illustrative misalignment angle of about 10°.

Figure 20:
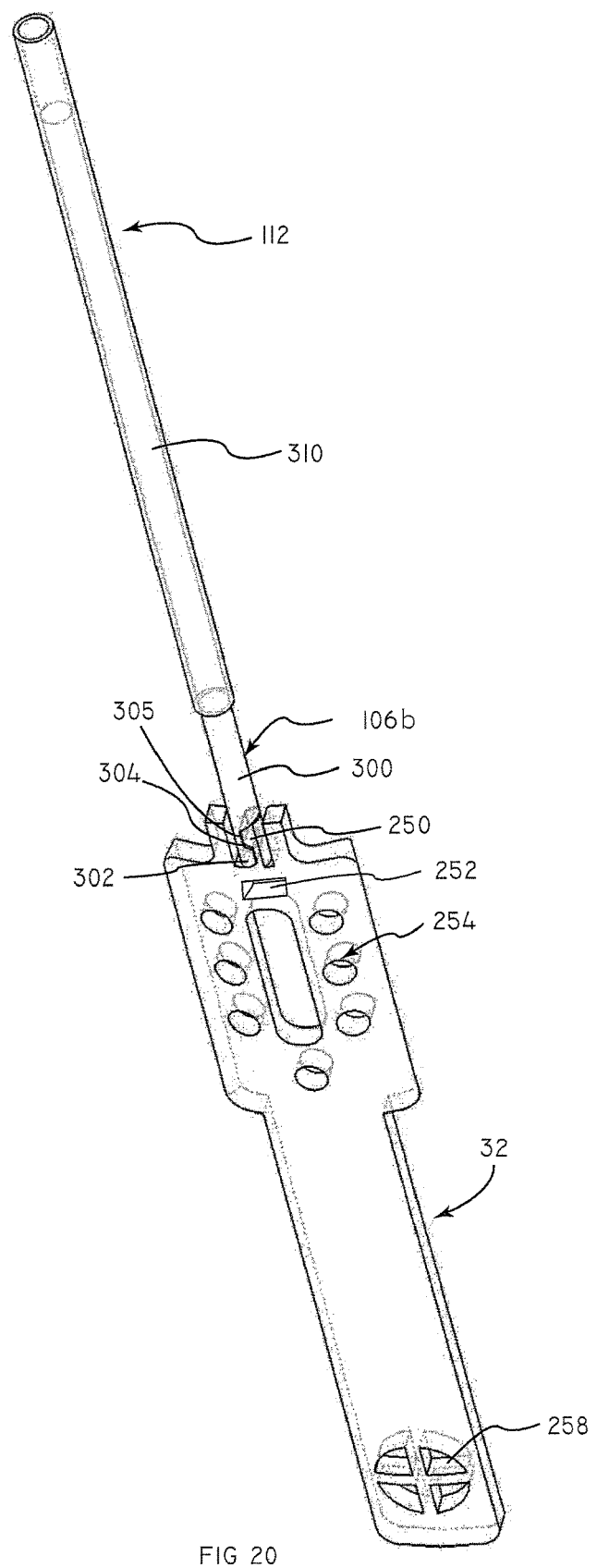
FIG. 20 shows the post variation of FIG. 14 in combination with an illustrative actuator and release actuator.

Referring now to FIG. 20, the variation of post 32 of FIG. 14 is shown in combination with an illustrative actuator 106b and release actuator 112. In FIG. 20, actuator 106b illustratively comprises rod 300 having post attachment element 302 that mates with actuator attachment element 250 of post 32. Angled camming surfaces 304 and 305 of post attachment element 302 and actuator attachment element 250, respectively, form an interface between post attachment element 302 and actuator attachment element 250. Proximal movement of actuator 106b with respect to post 32 is translated by the camming surfaces into a lateral force between the two elements that acts to separate and release post 32 from actuator 106b. Release actuator 112, illustratively tube 310, may be advanced over actuator 300 to cover the camming surface interface of the post and the actuator 106b, thereby forming a releasable attachment mechanism for securing the post to the actuator even during application of axial tension to the actuator. To separate post 32 from actuator 106b, e.g., after expansion and locking of anchor 30, release actuator 112 may be retracted relative to actuator 106b to the position shown in FIG. 20, thereby removing a constraint from camming surfaces 304 and 305 and allowing the post and actuator to be pulled apart. Release actuator 112 preferably is retracted less than about 1 inch relative to the actuator 106*b* in order to actuate the releasable attachment mechanism, e.g., to remove constraint from camming surfaces 304 and 305.

Referring now to FIG. 21, an alternative releasable attachment mechanism for attaching a variation of post 32 to a variation of actuator 106*b* is described. In FIGS. 21A and 21B, post 32 having actuator attachment element 320, illustratively an enlarged proximal opening within the post, is interference fit with post attachment element 330 of actuator 106*b*, illustratively an enlarged bulb, knob or other distal protrusion of the actuator. The slope of element 330 provides a camming surface that interfaces with an inside surface of opening 320. The angle of the camming interface between element 330 and opening 320 translates proximal movement of actuator 106*b* with respect to post 32 into a lateral movement between actuator 106*b* and post 32, thereby separating these elements. Release actuator 112, illustratively tube 310, covers the interference fit releasable attachment mechanism to preclude lateral movement of the post attachment element relative to the actuator attachment element, thereby releasably attaching the post to the actuator 106*b*. In FIG. 21C, tube 310 is retracted relative to the post and actuator, which permits lateral movement between the post and actuator attachment elements, thereby separating actuator 106*b* from post 32. If tube 310 has not been retracted, of course, proximal movement of actuator 106*b* moves post 32 and the distal portion of the anchor proximally.

Figures 22A, 22B, 22C:
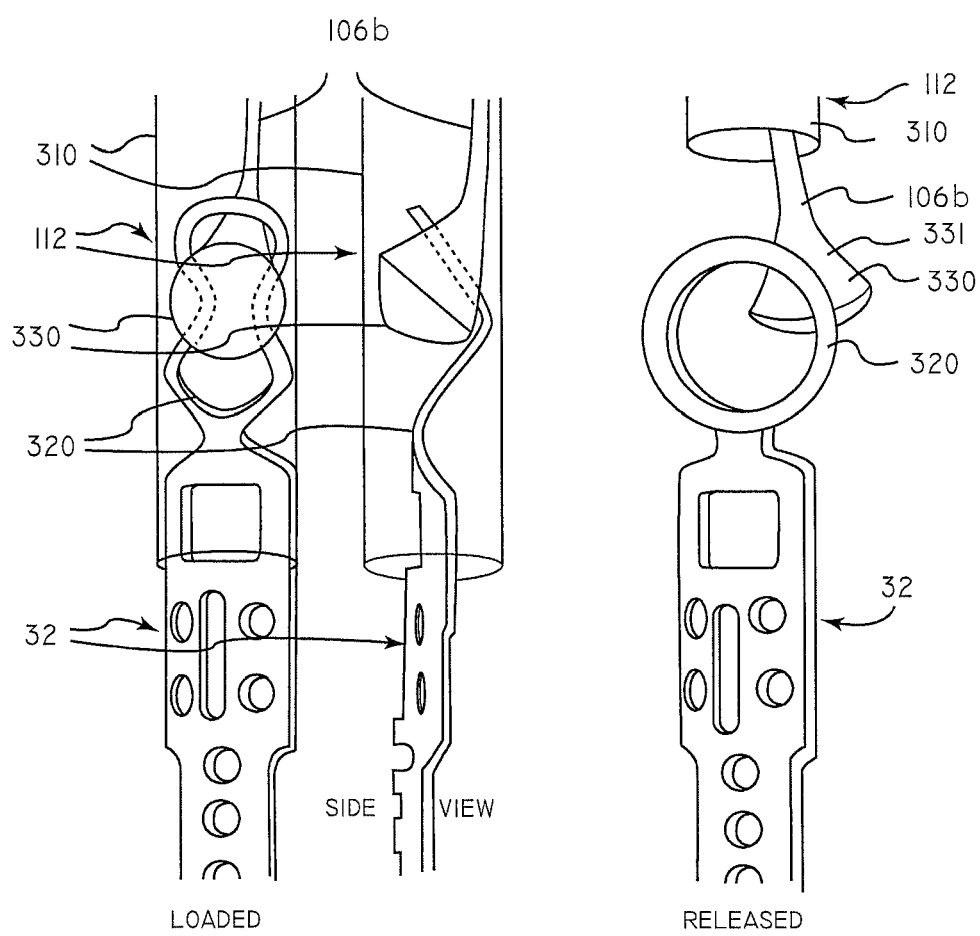
FIGS. 22A-22C show another variation of the releasable attachment mechanism.

FIG. 22 illustrate a variation of the releasable attachment mechanism of FIG. 21. In the variation of FIG. 22, actuator attachment element 320 of post 32 is deformable from a substantially round profile to an oval or "figure eight" profile by advancement of release actuator 112 over the attachment element. This forms a releasable attachment mechanism. In the deformed profile of FIGS. 22A and 22B, post attachment element 330 of actuator 106*b* is interference fit with the deformed actuator attachment element of post 32. In FIG. 22C, retraction of release actuator 112 relative to the post and actuator allows actuator attachment element 320 to resiliently resume its un-deformed or at-rest configuration, thereby permitting separation of post 32 from actuator 106*b*. Actuator attachment element 320 may, for example, be fabricated from a shape memory material, such as Nitinol. A camming surface 331 on post attachment element 330 and a corresponding surface on the inner portion of element 320 translate proximal movement of actuator 106*b* with respect to post 32 into lateral movement of element 330 with respect to element 320 when release actuator 112 has been retracted.

In the variation of FIG. 23, post attachment element 330 is deformable (as in FIGS. 23A and 23B), and anchor attachment element 320 may be interference fit with the post attachment element. FIG. 23C shows the post attachment element 330 in its at-rest configuration after tube 310 has been retracted, thereby releasing anchor attachment element 320. As will be apparent, for many or all of the two-part locking or attachment element elements described herein, the position of the elements may be reversed.

Figures 24A, 24B:
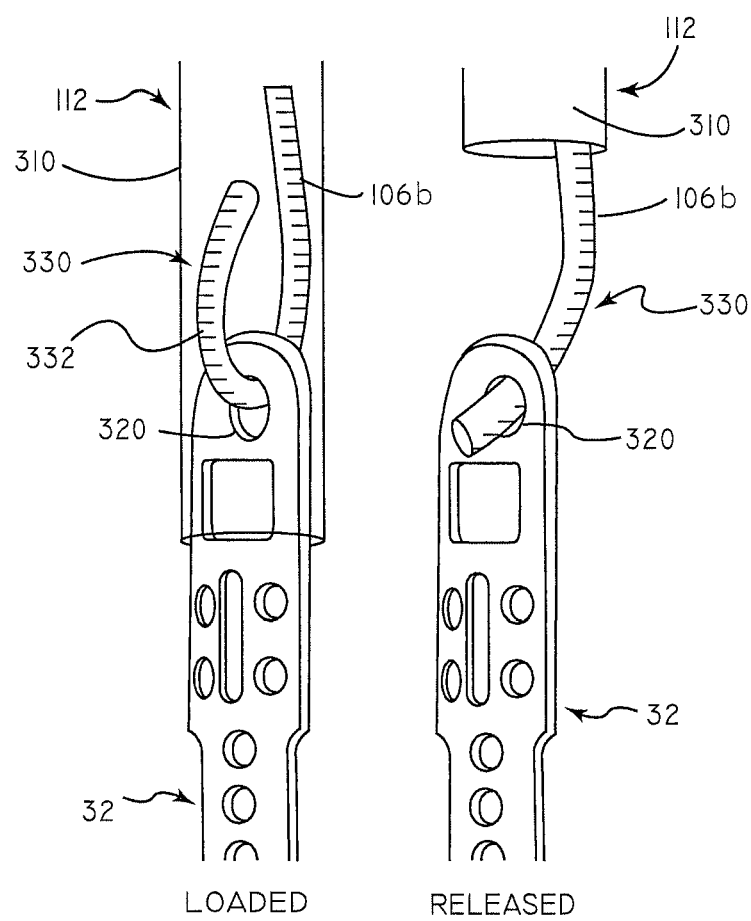
FIGS. 24A and 24B show still another variation of the releasable attachment element.

In FIG. 24, post attachment element 330 comprises wrap portion 332 that may be inserted through anchor attachment element 320, illustratively an eyelet, wrapped backwards, then covered with release actuator tube 310 to constrain the wrap portion 332 in the wrapped configuration, as in FIG. 24A. Release actuator tube 310 may be retracted relative to the wrap portion to resiliently or dynamically (e.g., by retracting actuator 106*b* relative to post 32) reshape the wrap portion to a substantially straight configuration for releasing the attachment between the post and the actuator, as in FIG. 24B. Wrap portion 332 preferably is fabricated from a shape memory material, such as Nitinol, or a resilient material, such as spring steel.

Figure 25:
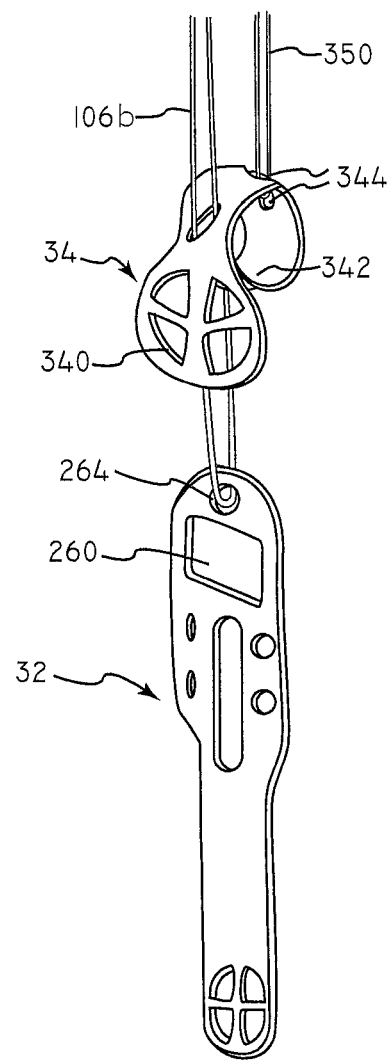
FIG. 25 shows a variation of the post, actuator and anchor lock element having a reversible lock.

FIG. 25 shows another variation of the post, actuator and anchor lock element. In FIG. 25, post 32 comprises post lock element 260 and actuator attachment element 264, illustratively an eyelet, through which actuator 106*b* is reversibly disposed. Anchor lock element 34 illustratively comprises a buckle, which may, for example, be formed from a cut tube or a bent resilient material. Anchor lock element 34 comprises anchor or braid attachment element 340 for attaching the buckle to anchor 30, and tab 342 for interlocking the buckle with post lock element 260, which illustratively is a slot formed through post 32. Actuator 106*b* therefore actuates the post (and therefore the distal end of the anchor to which the post is attached) as well as the anchor lock. Actuator 106*b* may be released from the post (and therefore from the anchor) by pulling one end of the control wire proximally to draw the control wire through and out of opening 264.

Anchor lock element 34 also comprises optional unlock actuator attachment 344, illustratively a pair of eyelets, through which unlock actuator 350 is releasably coupled to anchor lock element 34. Unlock actuator 350 illustratively comprises a control wire. Upon locking of tab 342 of buckle 34 within slot 260 of post 32, a proximally-directed force applied to unlock actuator 350 may remove the tab from the slot, thereby unlocking buckle 34 and post 32 and permitting the anchor to contract and elongate. Unlocking may be utilized, for example, to reposition or retrieve the anchor and valve apparatus even after the apparatus has been locked in the fully deployed configuration, as described previously with respect to FIG. 3.

FIG. 26 show another variation of the actuator, the lock actuator and the release actuator. As with other anchor lock elements, anchor lock element 34 in this embodiment is attached to a proximal end of the anchor, and the distal end of post 32 is attached to a distal end of the anchor. The anchor is not shown in FIG. 26 for ease of illustration. For the purposes of illustration, the unlock actuator also is not shown in FIG. 26.

As shown, actuator 106*b* actuates both post 32 (and therefore the distal end of the anchor to which the post is attached) and the lock formed between post lock element 260 and anchor lock element 34. In FIG. 26A, release actuator 112 passes through actuator 106*b* to actuate the releasable attachment mechanism between post 32 and actuator 106*b*. FIG. 26B provides a detail view of the releasable attachment mechanism. Actuator 106*b* comprises wrap portion 360 that passes through actuator attachment element 264 and wraps around the end of post 32. Wrap portion 360 may comprise a shape memory material, such as Nitinol, or a deformable material, e.g., a resiliently deformable material.

Wrap portion 360 further comprises first opening 362 for engaging release actuator 112, illustratively a wire or rod that passes through lumen Lu of actuator 106*b*. The walls of the lumen act a linear bearing and/or motion guide during advancement and retraction of the release actuator relative to the actuator. Actuator 106*b* also comprises second opening 364, which may be aligned with first opening 362 to engage release actuator 112, as shown. As seen in the cross-sectional view of FIG. 26C, wrap portion 360, and especially the curved portion 361 of the wrap portion, acts as a spring element that urges the first opening out of alignment with the second opening. In this manner, release actuator 112 may be interference or friction fit through first opening 362 and second opening 364. Retraction of the release actuator proximal of the first and second openings may actuate the releasable attachment mechanism to resiliently or dynamically unwrap portion 360 and release actuator 106b from post 32. Wrap and/or curved portion 360/361 of actuator 106b illustratively is disposed at a distal end of the actuator.

As will be apparent to those of skill in the art, the releasable attachment mechanism of FIG. 26 may also be utilized to attach a actuator 106a to a braided anchor 30. More generally, wrap portion 360 provides an illustrative first shape on an anchor actuation element 106 that is adapted to mate with a second shape on a post or anchor actuator attachment element (such as element 264 in FIG. 26, or a wire of the braid of anchor 30) to substantially prevent relative distal or proximal movement between the anchor actuation element and the anchor. The apparatus further comprises a release actuator adapted to actuate the releasable attachment mechanism. The release actuator is adapted to be moved to permit relative movement between the first shape and the second shape. This relative movement may change the first shape and/or the second shape to a third shape that permits relative distal or proximal movement between the anchor actuation element and the anchor or post. Furthermore, this relative movement may separate the anchor actuation element from the anchor or actuator attachment element.

Figure 27:
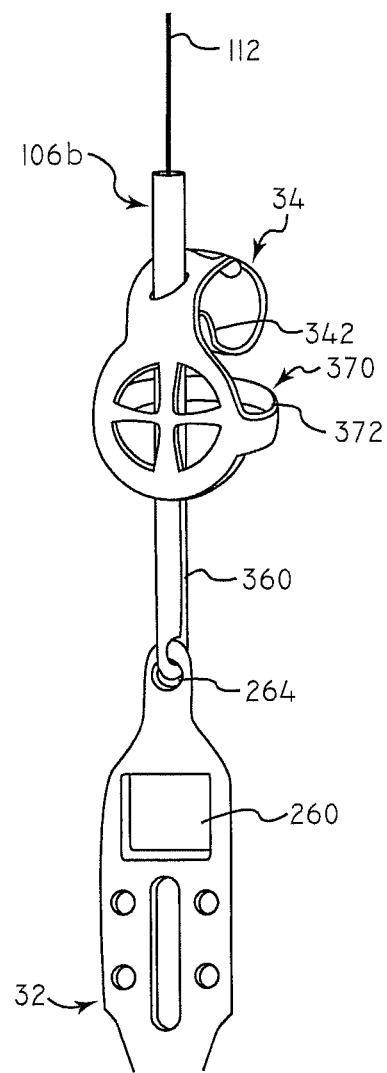
FIG. 27 shows a variation of the anchor lock element having a lock alignment feature.

FIG. 27 illustrates a variation of the anchor lock element of FIG. 26. In FIG. 27, anchor lock element 34 comprises lock alignment feature 370. Feature 370 comprises engagement portion 372, illustratively a loop, that is adapted to engage post 32 before engagement of anchor lock element 34 (i.e., before engagement of tab 342 of the anchor lock element) with post lock element 260. Feature 370 ensures alignment of the post and buckle prior to locking. Furthermore, feature 370 adds additional strength to anchor lock element 34 and opposes inwardly-directed forces applied to element 34 when valve 20 of apparatus 10 closes during diastole.

Figures 28A, 28B, 29:
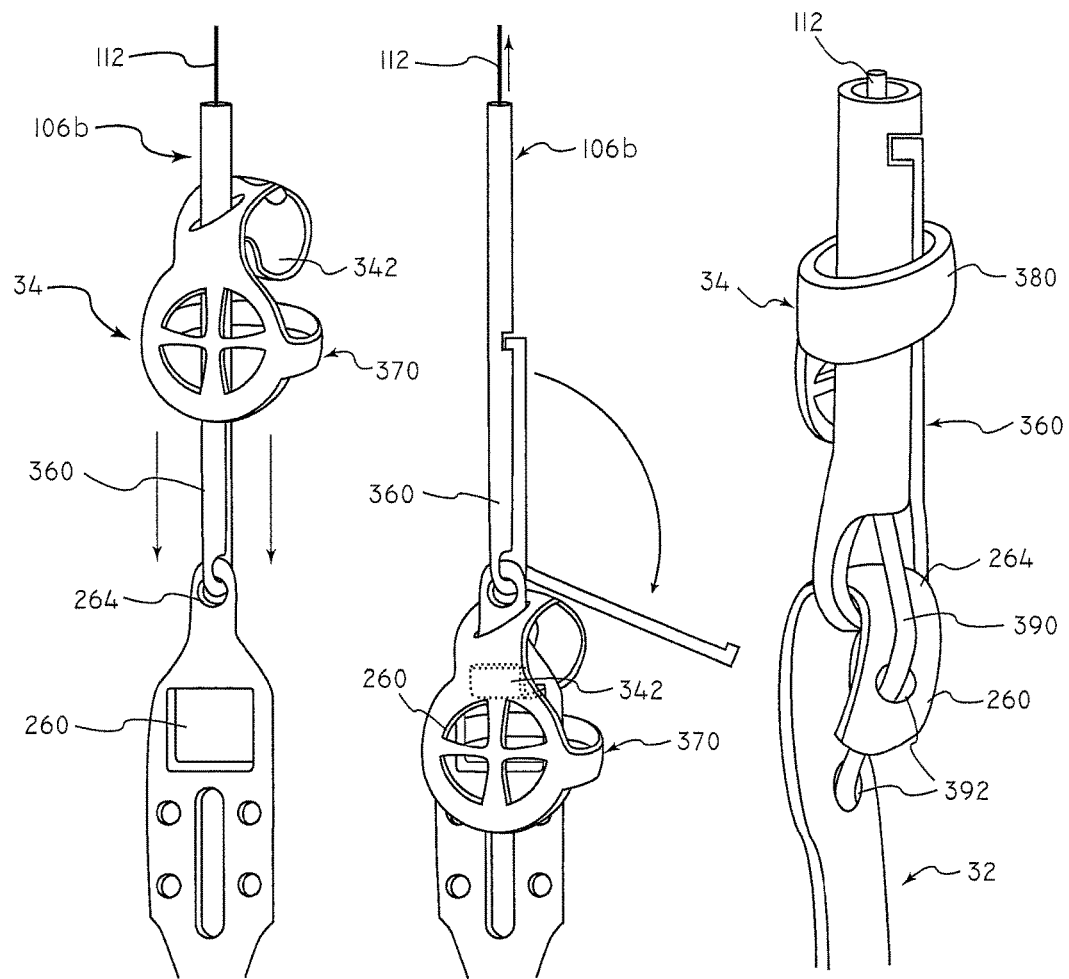
FIGS. 28A and 28B show expansion, locking and actuation of the releasable attachment mechanism of the apparatus of FIG. 27.
FIG. 29 shows another variation of the apparatus having an actuable lock prevention mechanism.

Referring now to FIG. 28, actuation of the apparatus of FIG. 27 is described. As seen in FIG. 28A, anchor lock element 34 is advanced distally relative to post 32, for example, by applying a distally-directed force to the anchor via anchor actuator 106a to move the proximal portion of the anchor distally while maintaining the position of post 32 via actuator 106b. Alternatively or additionally, a proximally-directed force may be applied to post 32 via actuator 106b while maintaining the position of the proximal end of the anchor to move the distal portion of the anchor proximally. Lock alignment feature 370 engages the proximal end of the post prior to interlocking of tab 342 of anchor lock element 34 with post lock element 260, thereby ensuring proper alignment. Continued retraction of post 32 relative to buckle 34 locks the post into the buckle, as shown in FIG. 28B. This also expands apparatus 10 to the fully deployed configuration of, e.g., FIGS. 1B and 2C. Next, release actuator 112 is retracted proximally relative to actuator 106b, which causes wrap portion 360 of the actuator to resiliently or dynamically swing outwards, thereby bringing first opening 362 and second opening 364 out of alignment. Proximal retraction of actuator 106b relative to post 32 removes wrap portion 360 from actuator attachment element 264 of post 32.

FIG. 29 shows a variation of the apparatus of FIGS. 27 and 28. In FIG. 29, anchor lock element 34 comprises locking hoop 380, while post lock element 260 comprises a wrapped or curved proximal end of post 32. The curved proximal end also forms actuator attachment element 264. Wrap portion 360 of actuator 106b is wrapped about the curved end of post 32. Release actuator 112, passing through first opening 362 and second opening 364 of actuator 106b, releasably secures this attachment. The release actuator further comprises kink 390 that facilitates passage of the actuator through release actuator attachment elements 392 of post 32, illustratively eyelets. When disposed through elements 392, release actuator 112 further acts as a lock prevention mechanism that precludes locking of the curved proximal end of post 32 with hoop 380 of anchor lock element 34.

In use, the proximal end of post 32 may be retracted through hoop 380 of anchor lock element 34. Release actuator 112 then may be retracted relative to anchor actuator 106b and post 32, such that the release actuator is disposed proximal of attachment elements 392 of the post. Next, post 32 may be allowed to distally advance until its curved proximal end catches and locks against hoop 380 of element 34. Continued retraction of release actuator 112 relative to actuator 106b facilitates separation of the actuator from the post, as described previously.

Figure 30A:
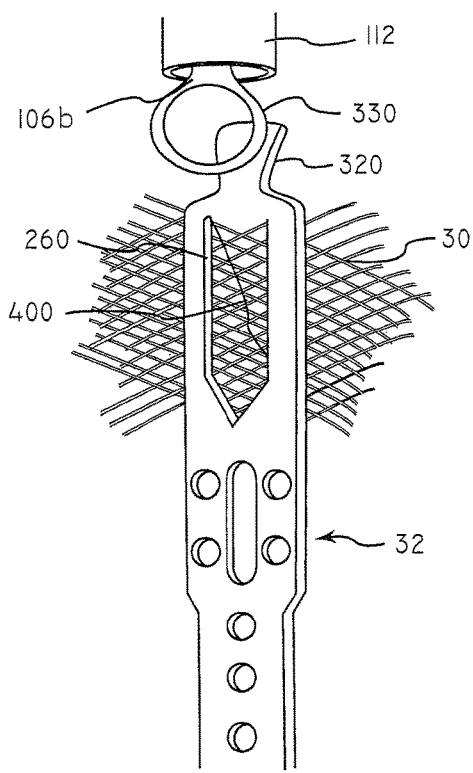
FIGS. 30A and 30B show a variation of the post that is configured to lock against the braid of the anchor.
Figure 30B:
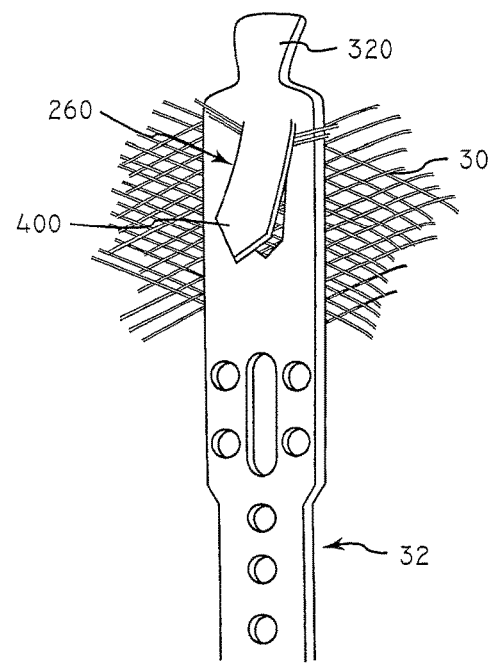

Referring now to FIG. 30, an embodiment of post 32 is described that is configured to lock against the braid of anchor 30, as opposed to a separate anchor lock element 34. Post lock element 260 illustratively comprises bent tab 400 that catches against the anchor braid to lock the anchor in a deployed configuration.

FIG. 31 illustrate locking and unlocking of a variation of anchor lock element 34. Anchor lock element 34 of FIG. 31 is similar to the buckle variation of element 34 described previously with respect to FIGS. 25 and 26. However, the variation of FIG. 31 is fabricated from a strip of material that is bent to form a wrapped or curved portion. FIG. 31A illustrates the apparatus prior to locking, FIG. 31B illustrates the locked configuration, and FIG. 31C illustrates unlocking through application of a proximally-directed unlocking force to unlock actuator 350.

Figures 32A, 32B:
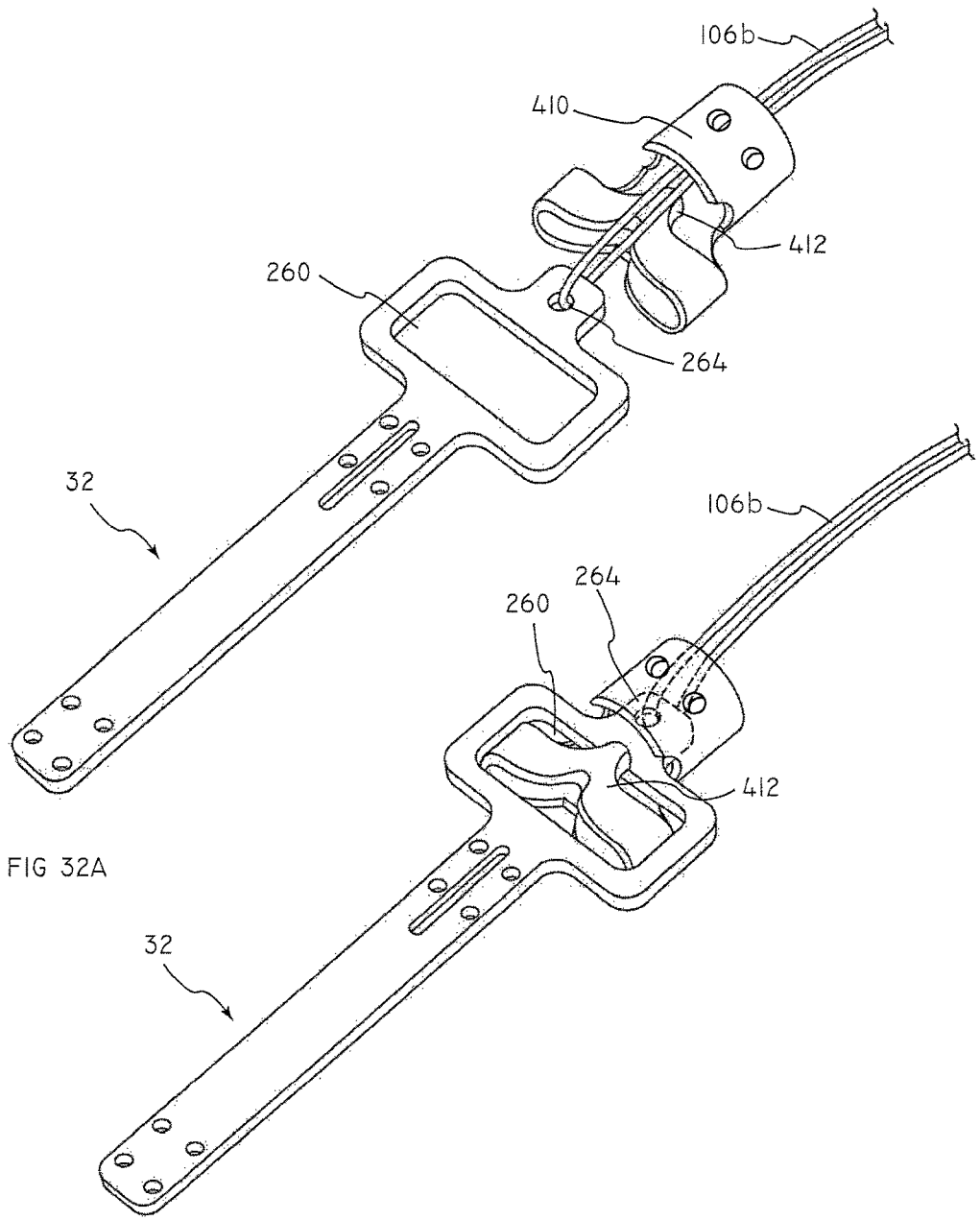
FIGS. 32A and 32B show another variation of a releasable actuation mechanism having a lock alignment mechanism which can be cut from a tube.

FIG. 32 show yet another embodiment of a releasable actuation mechanism. Anchor lock element 34 comprises lock alignment mechanism 410 disposed proximal of locking tab 412. As shown, lock alignment mechanism 410 engages the distal end of post 32 to align the post and the anchor lock element prior to locking of post lock element 260 with tab 412 of anchor lock element 34. Lock alignment mechanism 410 adds additional strength to anchor lock element 34 and opposes inwardly-directed forces applied to element 34 when valve 20 of apparatus 10 closes during diastole. Advantageously, the inwardly-directed forces act to maintain apparatus 10 in the locked configuration. Mechanism 410 optionally may be formed from a cut tube.

FIG. 33 illustrate a variation of anchor lock element 34 that may be formed from a cut tube. As seen in FIGS. 33A and 33B, element 34 comprises tabs 420 for engaging the curved proximal end of post 32 that forms post locking element 260. In order to lock the post to element 34, the curved distal end of the post is retracted proximally of tabs 420 by the action of proximal tension on post 32 by actuator 106b while element 34 is held stationary, as described above. As it enters anchor lock element 34, the curved end of the post is cammed inward by the engagement of the distal edge of element 34 with the outer surface of the curved end. Once proximal of tabs 420, the curved end of the post moves outward, thereby locking the apparatus and preventing subsequent distal movement of post 32 with respect to element 34. To unlock the apparatus, the curved portion of the post is drawn further proximally by actuator 106b until the tip of the curved portion moves into an opening 422 formed in element 34. As seen in FIGS. 33C and 33D, resilient distal advancement of the post relative to element 34, e.g., via resilient expansion of the braid of anchor 30, deforms and straightens the curved proximal end of post 32 through a camming engagement of the underside of the curved portion of the post with the inner surface of opening 422, thereby allowing actuator 106b to slide off of post 32, unlocking apparatus 10. The curved portion of post 32 optionally may be formed from a shape memory material, such that the post resumes its curved profile for subsequent relocking after unlocking.

FIG. 34 illustrate a variation of post 32 and anchor lock element 32. Anchor lock element 34 illustratively comprises a curved portion 35 that engages and enters the slot of post lock element 260 to lock the anchor as post 32 is drawn proximally into element 34 by actuator 106b. After locking, continued proximal retraction of post 32 by actuator 106b engages the distal end of the curved portion of element 34 with a camming surface 430 of post 32. Resilient distal advancement of post 32 (such as by the resilient contraction and elongation of the anchor to its at-rest configuration) then deforms and straightens the wrapped end of element 34, thereby permitting anchor lock element 34 to separate from post 32, unlocking the apparatus.

Figure 36:
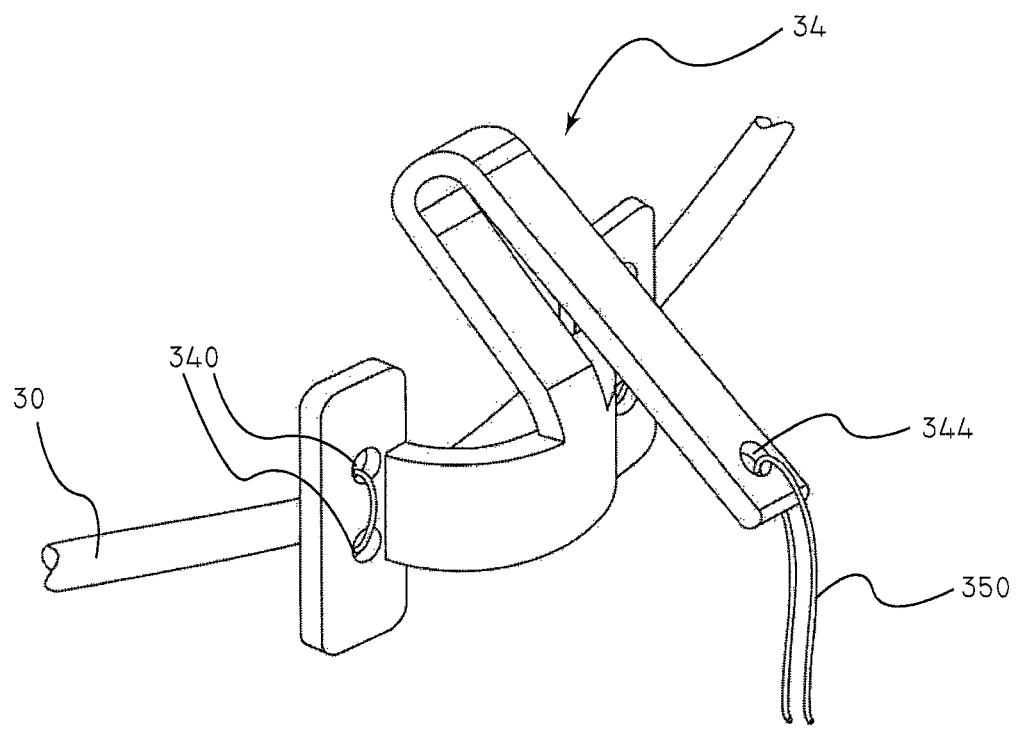
FIG. 36 shows attachment of a variation of the anchor lock element to the anchor.

FIGS. 35 and 36 illustrate additional buckle variations of anchor lock element 34. Proximal movement of post 32 into anchor lock element 34 (by, e.g., actuator 106b) engages a bottom surface 702 of a curved portion 700 of element 34 with the proximal end of post 32. Further proximal movement of post 32 with respect to element 34 cams curved portion 700 forward until the curved end 704 of curved portion 700 meets and resiliently moves into opening 260 in post 32, locking the apparatus. The variation of FIG. 36 illustrates attachment to the braid of anchor 30 via sutures or the like passed through openings 340 in element 34. The lock is unlockable via unlock actuator 350.

Figures 37, 38A, 38B:
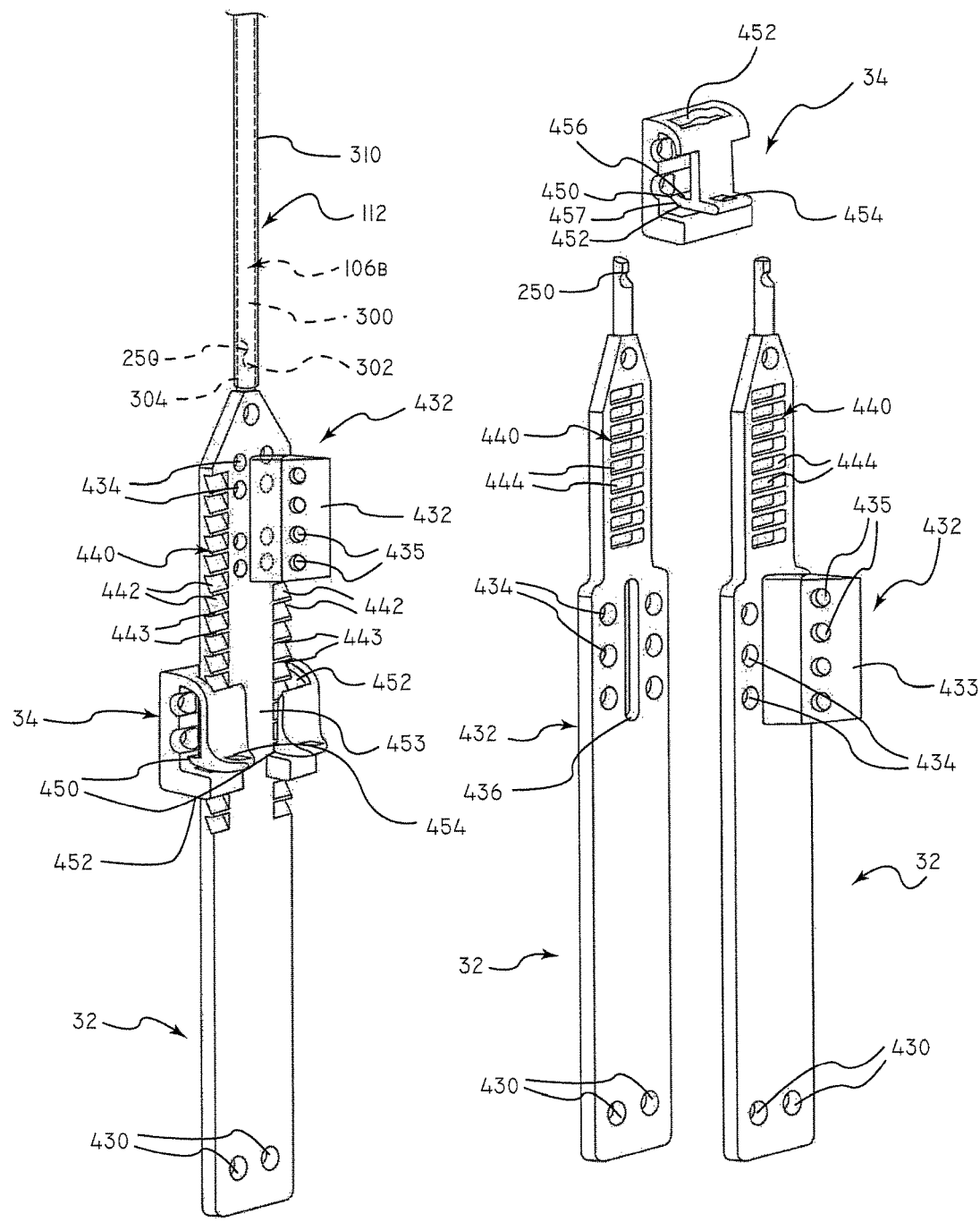
FIG. 37 shows a variation of the post and anchor lock element having a ratcheting lock.
FIGS. 38A and 38B show variations of the ratcheting lock.

Referring now to FIG. 37, an embodiment of a post 32 and anchor lock element 34 with a ratcheting lock is described. Post 32 comprises previously described actuator attachment element 250 that is releasably secured to post attachment element 302 of actuator 106b. (Other releasable attachment mechanisms may alternatively be used.) Post 32 also comprises braid attachment element 430 and valve attachment structure 432. In the variation of FIG. 37, valve attachment structure 432 comprises tab 433 that extends from post 32, as well as a plurality of holes 434 through post 32 and a plurality of holes 435 through tab 433. Replacement valve 20 may be attached to post 32 by sewing the valve to the valve attachment structure through holes 434 and/or 435.

Post 32 further comprises ratcheting locking element 440 having a plurality of inclined planes with cammming surfaces 442 and friction surfaces 443. The inclined planes are disposed along either side of tab 433 for ratcheting and locking against ratcheting anchor lock element 34. Anchor lock element 34 comprises ratchet teeth 450 on either side of the valve attachment elements that cam against surface 442 and lock against friction surfaces 443 of element 440 of post 32, as post 32 is proximally retracted through element 34. Advantageously, providing multiple rows of inclined plane ratchets along post 32 facilitates interlocking of the post and the element at multiple discrete locations.

Element 34 comprises proximal and distal slots 452 that receive post 32, as well as central longitudinal slot 453 that facilitate passage of tab 433 (and thereby valve 20) therethrough. Actuator 106b may be disposed through slots 452 prior to approximation and locking of the post to anchor lock element 34 in order to facilitate alignment of the post and the anchor lock element. Element 34 may be ratcheted to any position along ratchet lock element 440 to achieve any desired locking configuration and degree of expansion of apparatus 10. Valve attachment structure 432, and thereby replacement valve 20, may be positioned proximal of the ratchet lock post-deployment or in line with the ratchet lock (i.e., neither proximal nor distal to the ratchet lock). Element 34 further comprises unlock actuator attachment(s) 454 for coupling the element to an unlock actuator, e.g., previously described unlock actuator 350, to unlock element 34 by applying a proximally-directed unlocking force that displaces ratchet teeth 450 from friction surfaces 443.

FIG. 38 illustrate variations of the apparatus of FIG. 37. Ratchet lock elements 440 of posts 32 in FIG. 38 comprise a plurality of ratchet slots 444 in which ratchet tooth 450 of anchor lock element 34 may be locked. Ratchet tooth 450 comprises proximal friction surface 456 and distal camming surface 457 to facilitate proximal retraction of a post 32 through slot 452 for ratcheting of camming surface 457 through ratchet slots 444, but to preclude distal advancement of the post once ratchet tooth 450 is engaged within ratchet slots 444 by locking a ratchet slot against friction surface 456. As with the variation of FIG. 37, anchor lock element 34 is unlockable and comprises unlock actuator attachment 454. In contrast to the variation of FIG. 37, the ratchet lock is disposed proximally of valve attachment structure 432, and thereby proximally of replacement valve 20. In FIG. 38A, valve attachment structure 432 comprises slot 436 instead of tab 433.

FIG. 39 illustrate another variation of the ratchet lock of FIG. 37. In FIG. 39, ratchet lock elements 440 of post 32 extend along only one edge of the post. Thus, anchor lock element 34 comprises unitary ratchet tooth 450 for camming against surfaces 442 and locking against friction surfaces 443 of elements 440 of post 32, as post 32 is proximally retracted through element 34.

The apparatus of FIG. 39 also comprises unlock or adjustment actuator 500 that is releasably attached to anchor lock element 34 along unlock actuator attachment 454. Actuator 500 comprises two independently or concurrently actuable elements: adjustment element 510 and release element 520. Adjustment element 510 comprises elongated member 512 having protrusion 514 with lumen 515, as well as distal extension 516 with notch 518 having optional cammming surface 519. Release element 520 comprises elongated member 521, which may, for example, comprise a mandrel, that is configured for passage through lumen 515 of protrusion 514 of adjustment element 510. Elongated members 512 and 521 of actuator 500 preferably extend through delivery system 100 to the exterior of the patient for independent or concurrent advancement and/or retraction by a medical practitioner.

Figures 39A, 39B, 39C:
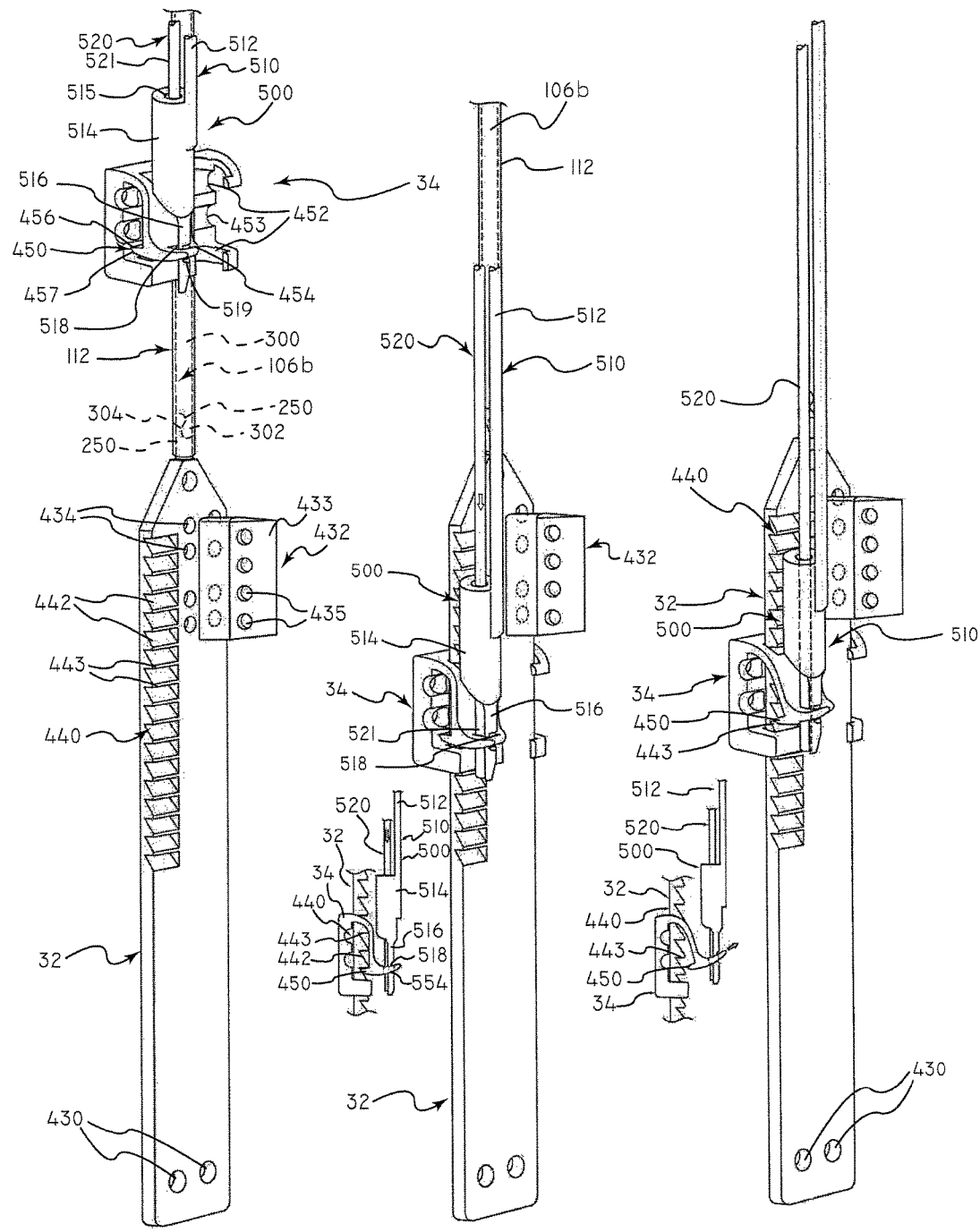
FIGS. 39A-39H show actuation of another variation of the ratcheting lock.

As seen in FIG. 39A, notch 518 of adjustment element 510 of actuator 500 may be positioned within unlock actuator attachment 454 of anchor lock element 34 during deployment of apparatus 10. As seen in FIG. 39B, anchor lock element 34 is locked within ratcheting lock elements 440 of post 32 by proximally retracting actuator 106b relative to anchor lock element 34. Release element 520 then may be advanced relative to adjustment element 510 to position elongated member 521 within unlock actuator attachment 454 adjacent distal extension 516 of adjustment element 510. This serves to friction lock or interference fit actuator 500 within attachment 454 along notch 518 of adjustment element 510. Thus, concurrent advancement and/or retraction of the adjustment and release elements of actuator 500 by a medical practitioner causes anchor lock element 34 to move in unison with actuator 500. As will be apparent, actuator 500 alternatively may be friction locked with anchor lock element 34 prior to full deployment of apparatus 10. Furthermore, actuator(s) 500 may assist, or be used in place of, actuators 106*a* to deploy apparatus 10.

Figures 39D, 39E, 39F:
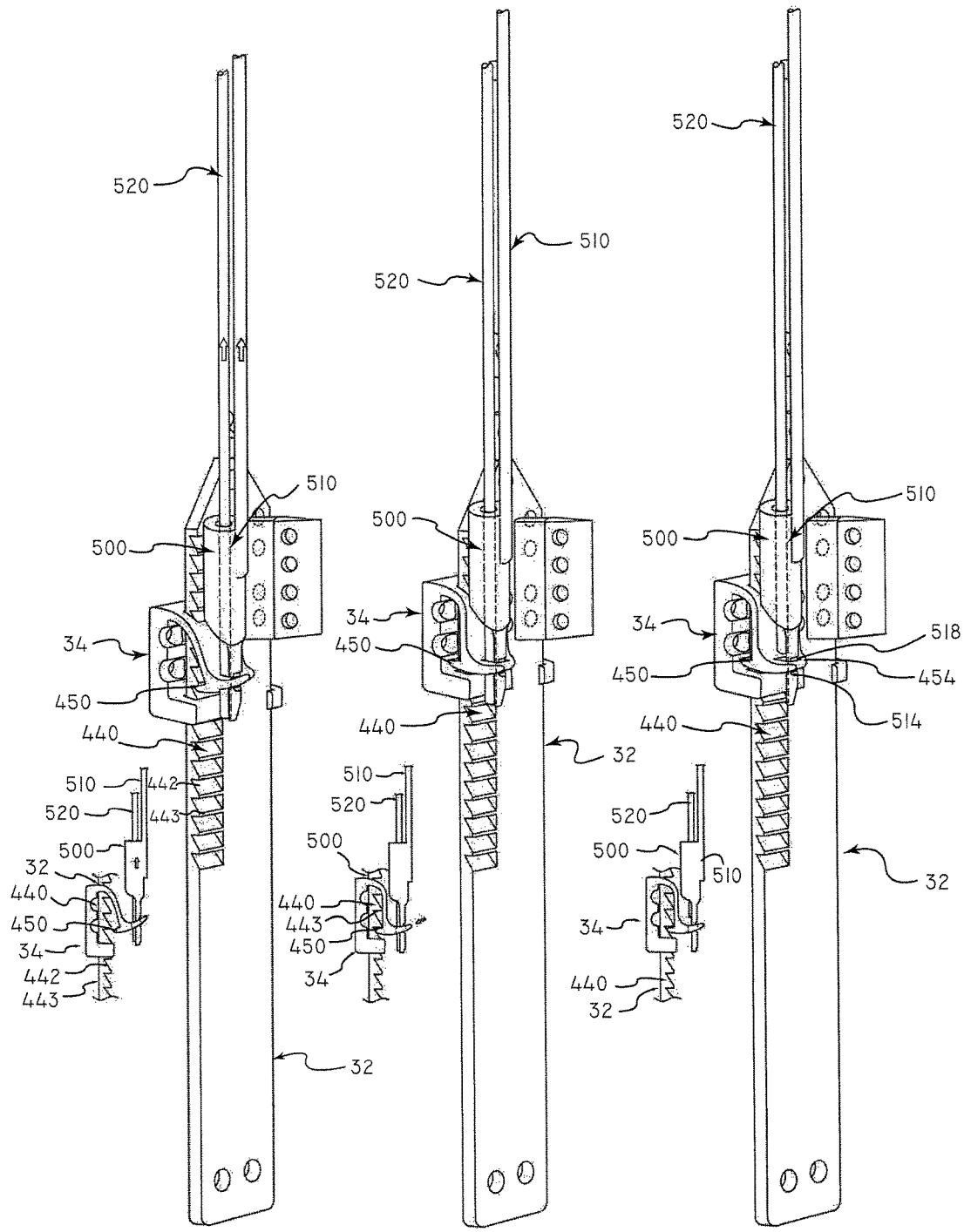

As seen in FIG. 39C, the lock formed between anchor lock element 34 and post 32 may be unlocked or adjusted, as desired, by applying a lateral unlocking force to ratchet tooth 450 via actuator 500 that pulls the ratchet tooth away from a friction surface 443 of ratcheting lock elements 440. Actuator 500 then may be distally advanced or, as seen in FIG. 39D, proximally retracted relative to ratcheting lock elements 440 and post 32 to further expand or partially collapse anchor 30, respectively (further expansion alternatively may be achieved by further ratcheting ratchet tooth 450 along camming surface 442 of ratcheting lock elements 440, e.g., by further proximally retracting actuator 106*b*, which is not shown in FIGS. 39C-39F for the sake of clarity). Anchor actuation elements 106 may assist such controlled expansion or collapse anchor 30.

Figures 39G, 39H:
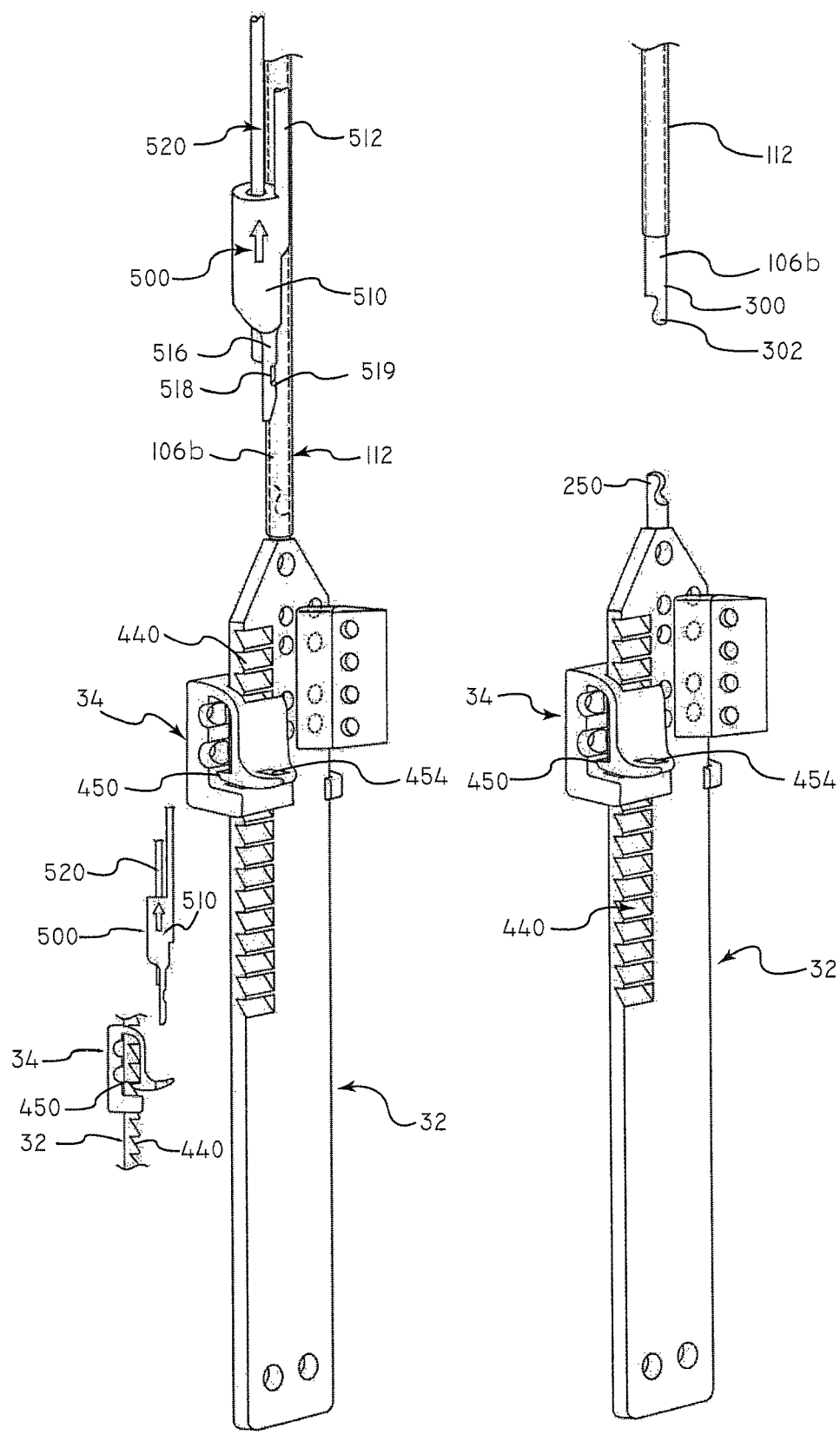

When (re-)positioned at a desired location and/or when a desired degree of locking has been achieved, the lateral unlocking force may be removed from ratchet tooth 450 to again lock anchor lock element 34 to post 32 along ratcheting lock elements 440, as in FIG. 39E. To complete deployment of apparatus 10, adjustment actuator 500 and actuator 106*b*, as well as actuator 106*a* (not shown), may be separated from the apparatus. In FIG. 39F, release element 520 of actuator 500 is proximally retracted relative to adjustment element 510, thereby removing elongated member 521 of release element 520 from unlock actuator attachment 454 of anchor lock element 34. This removes the interference fit between notch 518 and attachment 454. Proximal retraction of actuator 500 relative to anchor lock element 34 detaches adjustment element 510 of actuator 500 from attachment 454 of anchor lock element 34, as in FIG. 39G. Optional camming surface 519 along notch 518 may facilitate such detachment. In FIG. 39H, actuator 106*b* is detached from post 32 by retracting release actuator 112 relative to the actuator, as described previously.

Referring now to FIG. 40, another variation of an adjustable ratcheting lock element is described. As seen in FIG. 40A, post 32 comprises tube 470 having lumen 471 and ratcheting lock element 472, illustratively a plurality of slots that communicate with lumen 471. Post 32 also comprises valve support structure or attachment element 474 and braid attachment element 476.

Anchor lock element 34, which may be fabricated from a cut tube, comprises a substantially cylindrical structure having braid attachment element 480, lumen 482 and tabs 484. As seen in the top view of FIG. 40B, tabs 484 of anchor lock element 34 are configured for locking within the slots of ratcheting lock element 472 of post 32. As seen in the top view of FIG. 40C, adjustment actuator 490, illustratively mandrel M having tapered distal end 494 that acts as a camming surface, may be advanced through lumen 481 of anchor lock element 34 and lumen 471 of tube 470 of post 32, to displace tabs 484 from the locking slots of post 32, thereby unlocking the post from the anchor lock element. This facilitates, for example, readjustment of a degree of locking/expansion of apparatus 10, repositioning of apparatus 10, retrieval of apparatus 10, etc.

FIG. 41 illustrate a variation of anchor lock element 34 wherein tabs 484 are positioned along a different axis. This may provide a more secure lock between post 32 and anchor lock element 34. FIG. 42 illustrate a variation of post 32 configured for use with the variation of anchor lock element 34. In FIG. 32, post 32 comprises groove 478 that connects the slots of ratcheting lock element 472. Groove 478 does not communicate with lumen 471 of tube 470 of post 32. Rather, the groove may act as a lock alignment mechanism that guides tabs 484 of anchor lock element 34 along post 32 and ratcheting lock element 472, as seen in the top view of FIG. 42B.

Referring now to FIG. 43, a method of actuating the variation of FIG. 41 is described. As seen in FIG. 43A, adjustment actuator 490 is initially disposed through lumen 482 of anchor lock element 34 and within lumen 471 of post 32. Post 32 then may be proximally retracted relative to anchor lock element 34, e.g., via actuator 106*b* (not shown). In FIG. 43B, actuator 490 serves as a lock prevention mechanism that precludes locking of tabs 484 within ratcheting lock element 472. In FIG. 43C, actuator 490 is retracted relative to post 32 and anchor lock element 34, which opens up lumen 471 of tube 470 and allows tabs 484 to pass through the slots of ratcheting lock element 472, thereby locking the post to the anchor lock element. In FIG. 43D, actuator 490 is re-advanced within lumen 471, such that tapered distal end 494 of mandrel M serves as a camming surface that urges tabs 484 out of lumen 471 as the actuator is advanced. This unlocks the post from the anchor lock element to facilitate adjustment, repositioning or retrieval of apparatus 10. In FIG. 43E, a degree of locking/expansion of the apparatus is adjusted by repositioning anchor lock element 34 relative to post 32, and thereby tabs 484 relative to ratcheting lock element 472. When properly adjusted, actuator 490 may be removed from lumen 471 of tube 470 of post 32, as in FIG. 43F. Tabs 484 resiliently return to the locked configuration within the slots of ratcheting lock element 472.

Figures 44A, 44B:
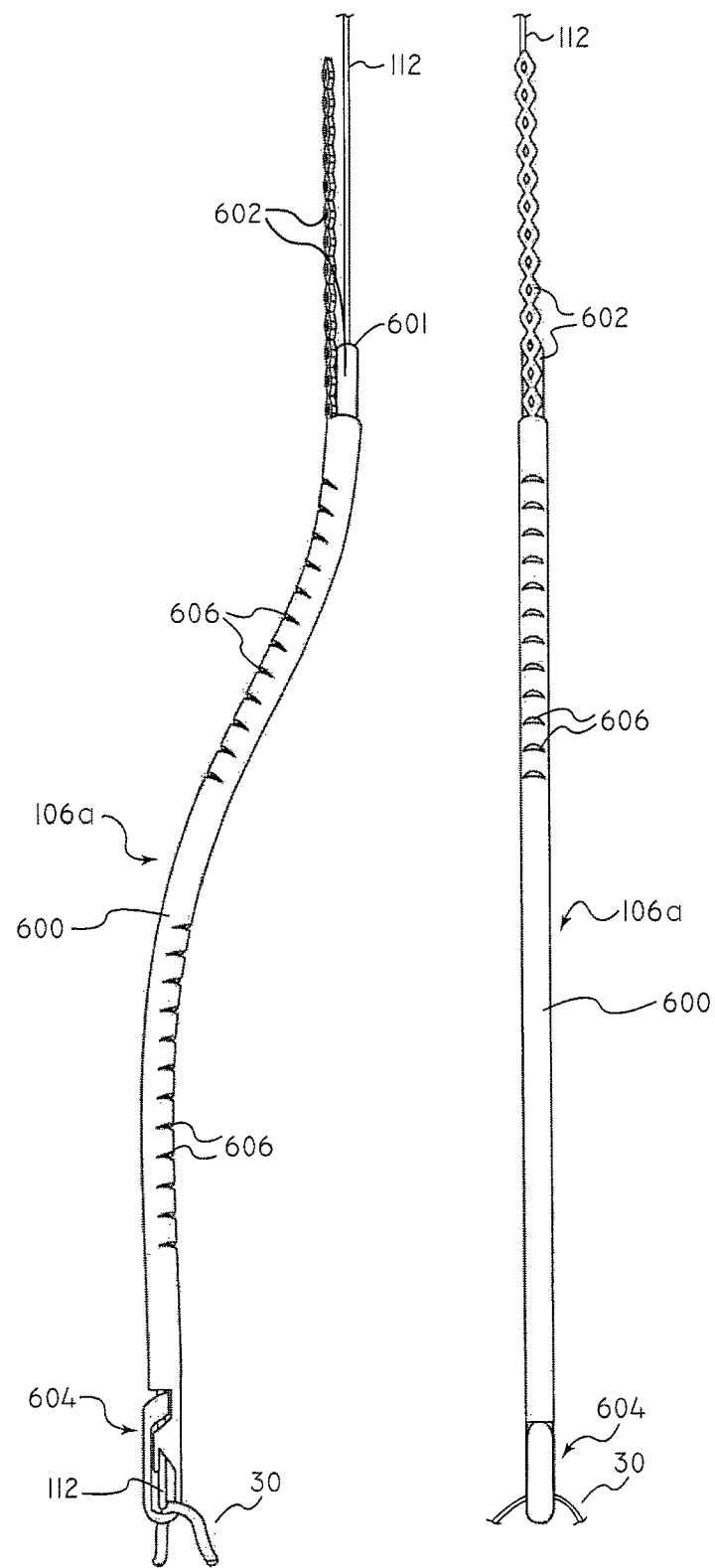
FIGS. 44A and 44B show a variation of an anchor/actuator.

Referring now to FIG. 44, an embodiment of anchor/actuator 106*a* is described. Actuator 106*a* comprises elongated member 600 having proximal extension 602 that may be attached, for example, to previously described multi-lumen shaft or catheter 108 of delivery system/deployment tool 100 (see FIG. 1), e.g., via epoxy, UV curing, etc. Lumen 601 extends through elongated member 600 from proximal extension 602 to releasable attachment mechanism 604. Releasable attachment mechanism 604 releasably attached actuator 106*a* to the braid of anchor 30. The mechanism comprises release actuator 112 and illustratively is similar to the previously described releasable attachment mechanism of FIGS. 26-28. Release actuator 112, illustratively a mandrel, passes through a lumen Lu of multi-lumen shaft 108 and then through lumen 601 of actuator 106*a* to mechanism 604.

Actuator 106*a* further comprises shaping features 606 that affect a shape of the anchor actuator when an anchor actuation force is applied to anchor 30. These features may comprise, for example, reduced diameter portions of the actuator, reduced wall thickness portions of the actuator and/or slits formed in the anchor actuator. Application of an anchor actuation force may, for example, provide actuator 106*a* with the profile seen in FIG. 44A. This profile may facilitate expansion of anchor 30/apparatus 10. As will be apparent, shaping features may be provided with any anchor actuation elements 106, including any of the previously described variations of actuators 106*b*.

As seen in FIG. 45, releasable attachment mechanism 604 comprises wrap portion 610 that may, for example, pass through the braid of anchor 30 and wrap around the proximal end of the anchor. Wrap portion 610 may comprise a shape memory material, such as Nitinol, or a deformable material, e.g., a resiliently deformable material. The wrap portion comprises first opening 612 for engaging release actuator 112. The walls of lumen 601 of elongated member 600 may act as a linear bearing and/or motion guide during advancement and retraction of the release actuator relative to the actuator. Actuator 106a also comprises second opening 614, which may be aligned with first opening 612 to engage release actuator 112, as shown. Wrap portion 610, and especially curved portion 611 of the wrap portion, acts as a spring element that urges the first opening out of alignment with the second opening to engage and hold release actuator 112 in place.

As seen in FIG. 45C, when the release actuator is retracted proximally relative to the actuator, wrap portion 610 resiliently or dynamically swings outwards. Thereafter, proximal retraction of anchor actuator 106a relative to anchor 30 detaches wrap portion 610, and thereby actuator 106a, from the anchor. Surface 616 of wrap portion 610 may act as a camming surface as the inner surface of wrap portion 610 slides along the anchor braid 30 to facilitate such detachment.

In this manner, release actuator 112 may be interference or friction fit through first opening 612 and second opening 614. Retraction of the release actuator proximal of the first and second openings actuates releasable attachment mechanism 604 to resiliently or dynamically unwrap portion 610 and release actuator 106a from anchor 30. Wrap portion 610 of actuator 106a illustratively is disposed at a distal end of the actuator.

Figures 47A, 47B, 47C:
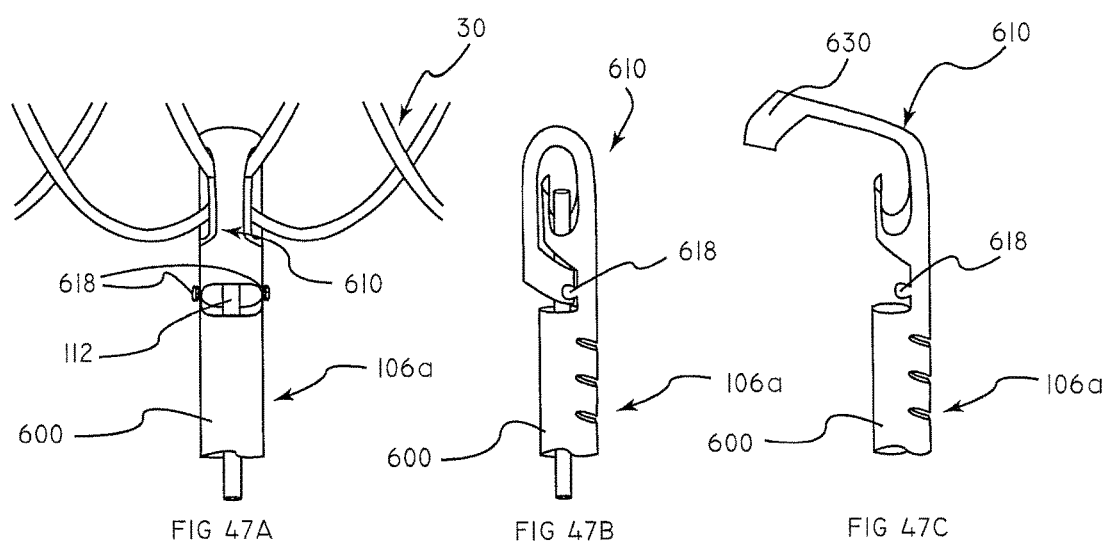
FIGS. 47A-47C show another variation of the releasable attachment mechanism.

With reference to FIG. 46, a variation of releasable attachment mechanism 604 is described. In FIG. 46, wrap portion 610 illustratively comprises tabs 618 that act as an alignment mechanism for aligning the wrap portion of mechanism 604 with elongated member 600. This may facilitate advancement of release actuator 112 through mechanism 604. FIG. 47 illustrate a variation of tabs 618 wherein the tabs are rounded. This may reduce friction, provide an atraumatic surface, etc. Additional shapes for tabs 618 will be apparent. Alternatively, tabs 618 may act as spring elements which are loaded when element 630 is seated, as shown in FIG. 47B. In this configuration tabs 618 apply a force directed towards element 630 such that 630 will be ejected when element 112 is retracted. In this way tabs 618 apply a restraining force on element 112 which reduces the risk of an early release.

Figures 48A, 48B, 48C:
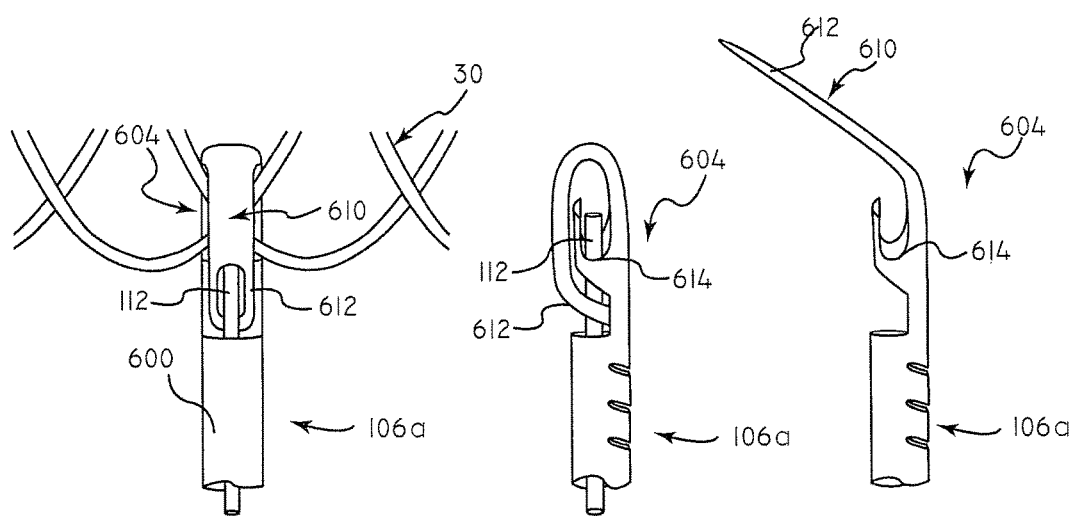
FIGS. 48A-48C show yet another variation of the releasable attachment mechanism.

FIG. 48 illustrate a variation of wrap portion 610 that comprises a substantially straight distal region in an at-rest configuration, as seen in FIG. 48C. It is expected that providing a substantially straight distal region along wrap portion 610 may facilitate detachment of actuator 106a from anchor 30, i.e., may reduce a risk of snagging the wrap portion along the braid of the anchor. The wrap portion may be resiliently deformed for passage, of release actuator 112 through first opening 612, as in FIGS. 48A and 48B.

Referring now to FIG. 49, variations of release actuator 112 for use with releasable attachment mechanism 604 are described. In FIG. 49A, the release actuator comprises a simple mandrel. In FIGS. 49B and 49C, the release actuator comprises protrusion 620 having friction surface 621. In FIG. 49D, actuator 112 comprises coil 622. In FIGS. 49E-49H, the actuator comprises kink 624, which may act as a cammming surface, as shown. The kink may also provide tactile feedback to a medical practitioner. In FIGS. 49I and 49J, the release actuator comprises ball or knob 626 disposed proximal of the actuator's distal end. In FIGS. 49K and 49L, ball 626 is disposed at the distal end of actuator 112. The ball may act as a camming surface. In FIG. 49M, actuator 112 comprises protrusion 628 having proximal camming surface 629. In FIG. 49N, the actuator comprises oblong protrusion 430 having friction surface 431. Additional variations of actuator 112 will be apparent.

Figures 50A, 50B:
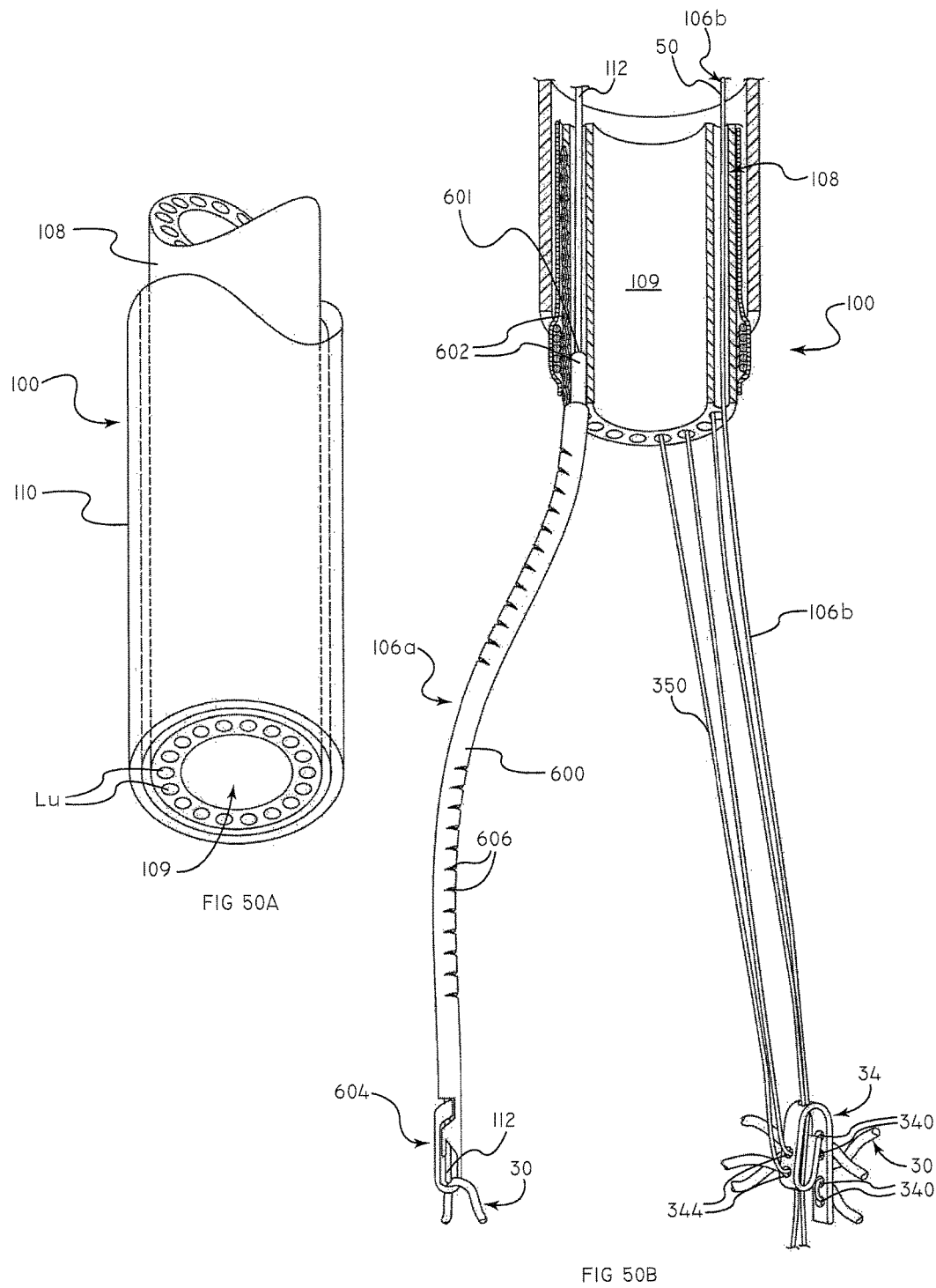
FIGS. 50A and 50B show detail views of an embodiment of the delivery system/deployment tool.

Referring now to FIG. 50, an embodiment of delivery system/deployment tool 100 is described. FIG. 50A provides a detail view of multi-lumen catheter 108 and sheath 110. As discussed previously catheter 108 comprises central lumen 109 and a plurality of circumferentially-disposed lumens Lu.

As seen in FIG. 50B, actuator 106a is coupled to catheter 108 via proximal extension 602, such that lumen 601 is coaxially disposed within a lumen Lu of the catheter. Release actuator 112 extends through lumens Lu and 601. Actuator 106a is distally attached to the braid of anchor 30 along releasable attachment mechanism 604. For the sake of clarity, a single actuator 106a is shown in FIG. 50B, but multiple such actuators preferably are provided, as in FIG. 51 described hereinafter.

FIG. 50B also illustrates actuator 106b. The actuator extends through a lumen Lu of catheter 108 and through anchor lock element 34 to post 32 (not shown). Unlock actuator 350 is also provided and extends through a lumen Lu to unlock actuator attachment 344 of anchor lock element 34. Anchor lock element 34 illustratively comprises the variation described previously with respect to FIG. 31. The element is attached to the braid of anchor 30 along anchor attachment elements 340. As with actuator 106a, a single anchor lock element 34 and actuator 106b are shown in FIG. 50B. This is only for the sake of clarity, and multiple such actuators may be provided, e.g., three actuators.

Figure 51A:
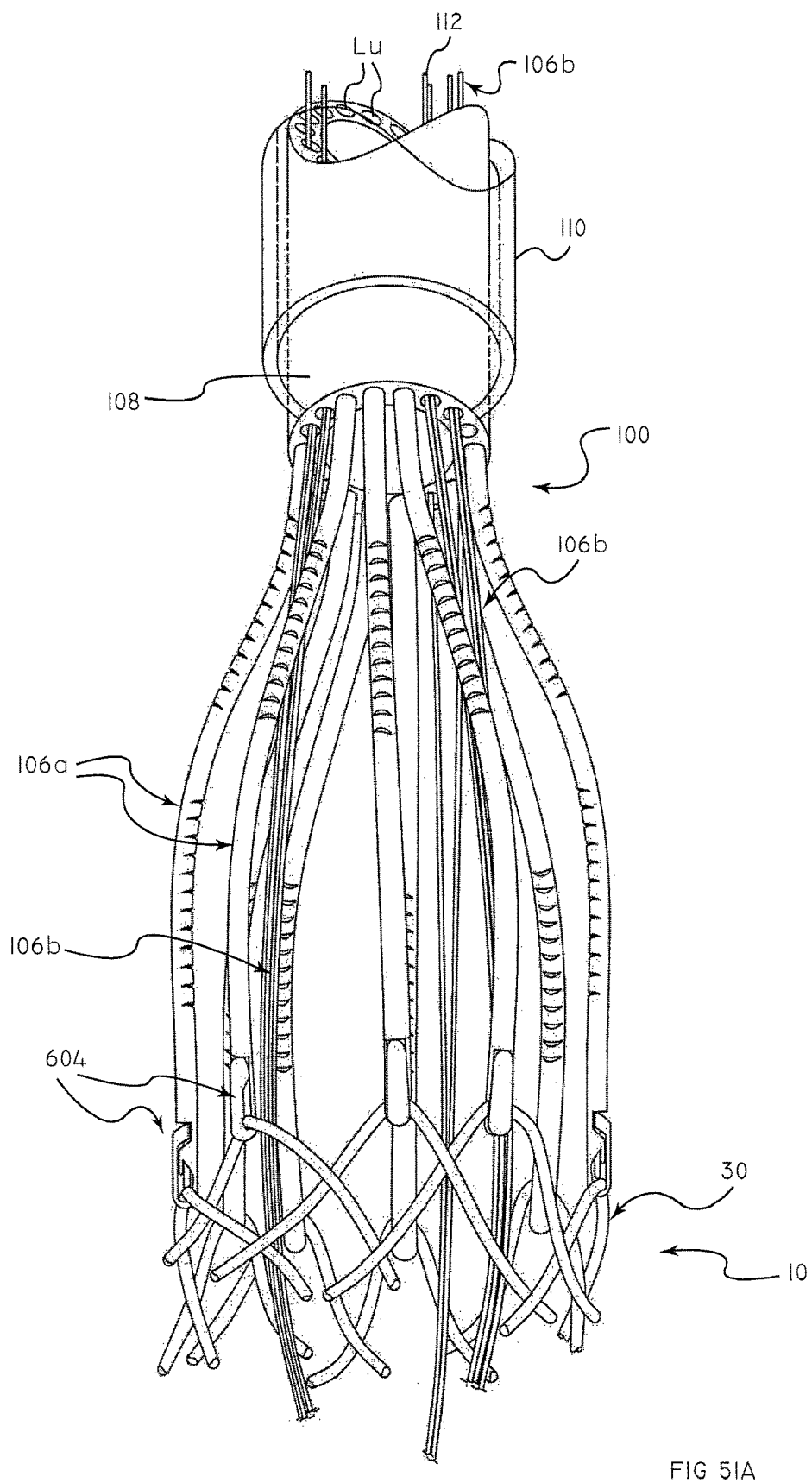
FIGS. 51A and 51B show the delivery system/deployment tool of FIG. 50 releasably attached to apparatus 10, and detached from the apparatus.
Figure 51B:
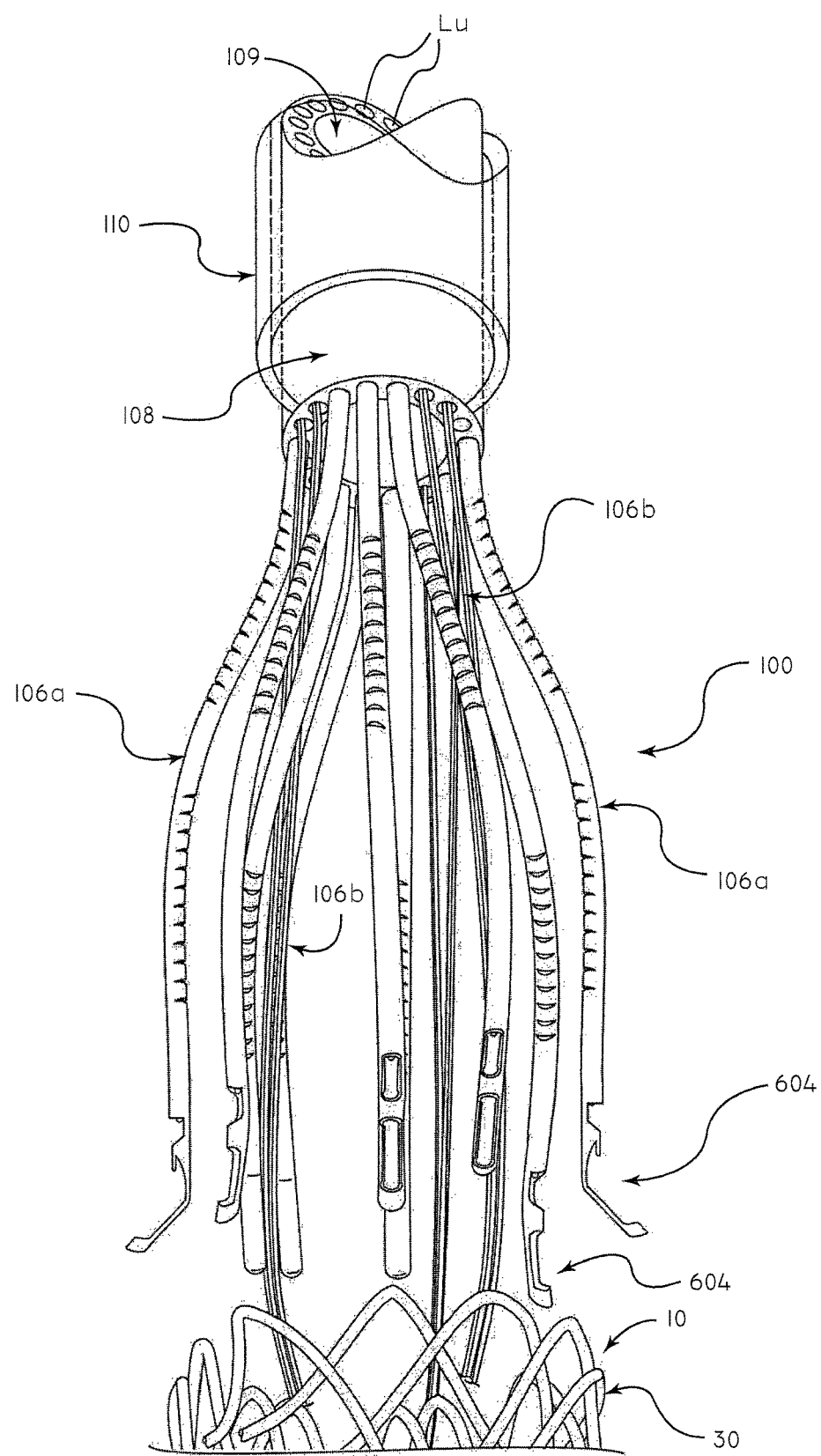

Referring now to FIG. 51, delivery system/deployment tool 100 is shown with a plurality of actuators 106a and actuators 106b for releasable attachment to anchor 30 of apparatus 10. In FIG. 51A, anchor actuation elements 106a are coupled to the anchor. In FIG. 51B, the elements are decoupled from the anchor.

Figure 52A:
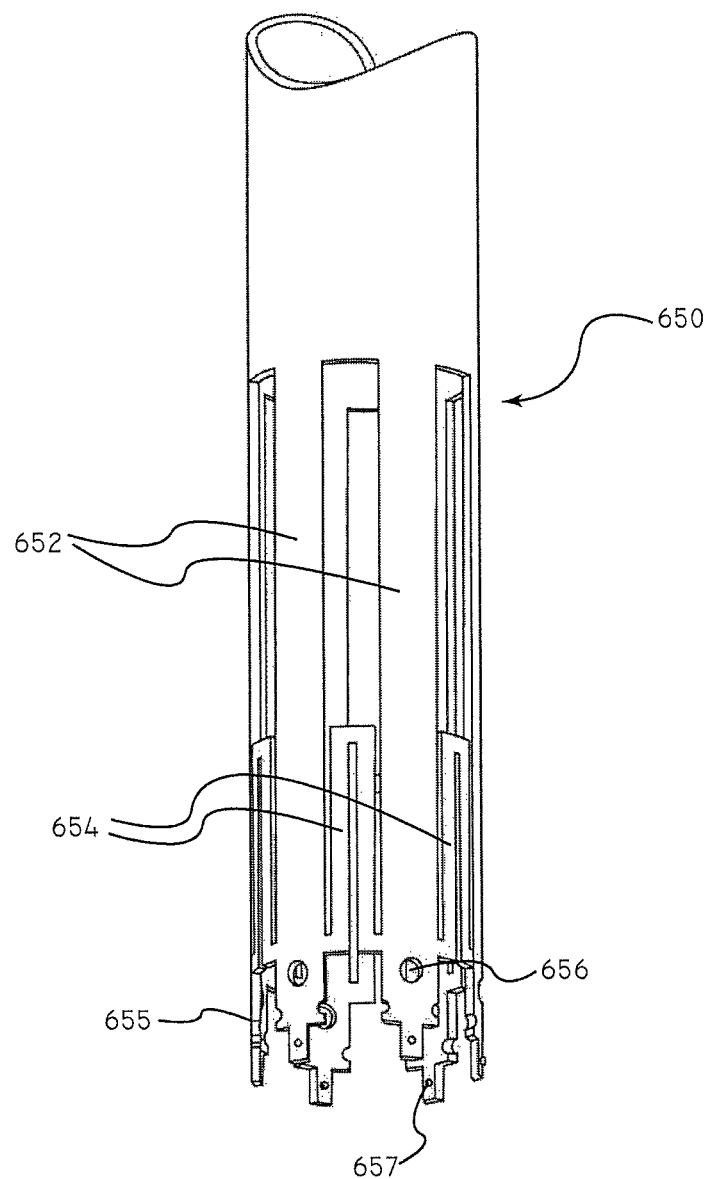
FIGS. 52A and 52B show a variation of the delivery system/deployment tool of FIGS. 50 and 51 wherein the actuators extend from a unitary structure.
Figure 52B:
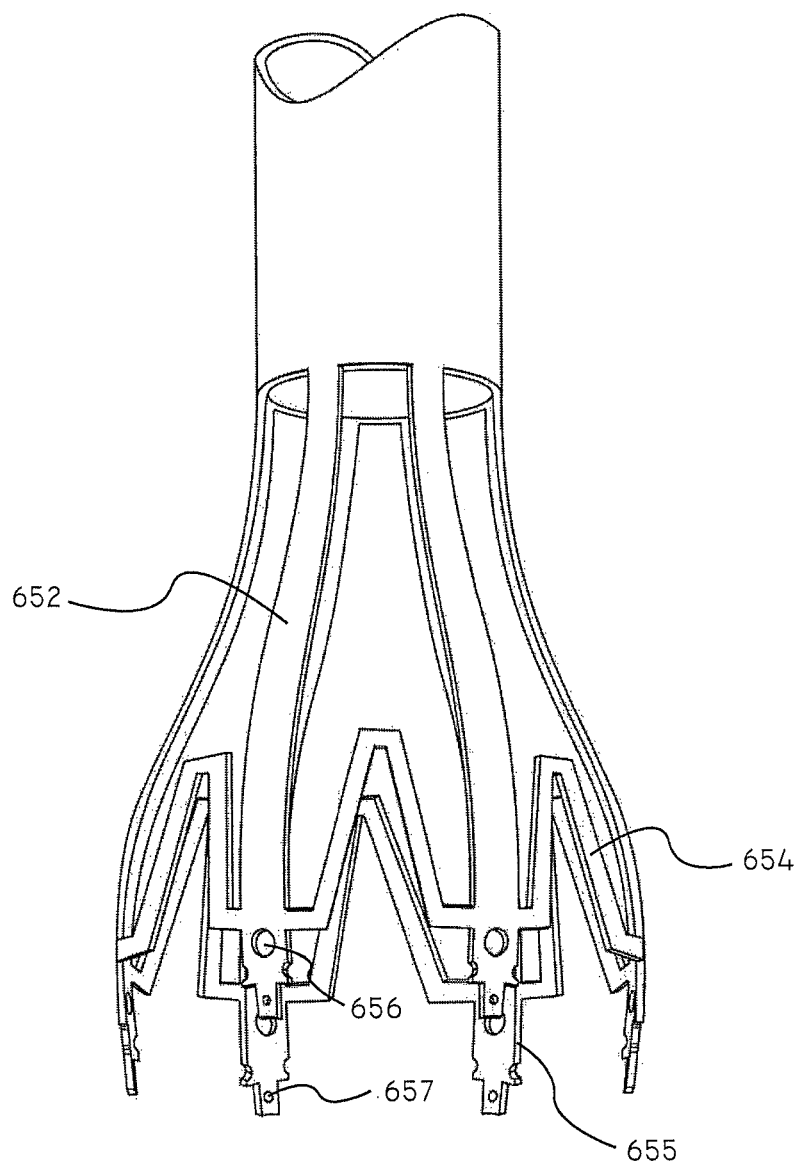

With reference now to FIG. 52, a variation of the delivery system/deployment tool of FIGS. 50 and 51 is described comprising a plurality of arms or actuators that extend from a unitary structure. Unitary structure 650, which may extend from a distal region of multi-lumen shaft 108, is preferably fabricated from a laser-cut tube. Structure 650 comprises a plurality of circumferentially disposed arms 652 that serve as actuators. Expansile elements 654 may be disposed between arms 652 and facilitate constraint of the arms radially outward or inward with respect to other arms as the anchor reshapes. FIG. 52A shows the arms in a radially collapsed configuration, and FIG. 52B shows the arms in a radially expanded configuration. Wrap portions 655 are adapted to wrap around the proximal portion of an anchor braid. Openings 656 and 657 are formed in wrap portions 655 to engage a release actuator, as described in embodiments above.

Figure 53A:
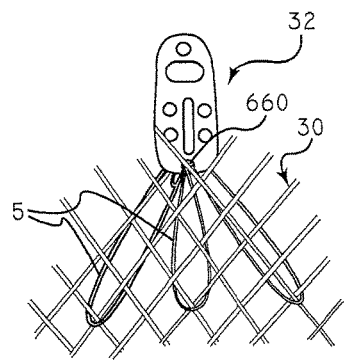
FIGS. 53A-53C show various ways to connect elements to the anchor of the replacement valve apparatus.
Figure 53B:
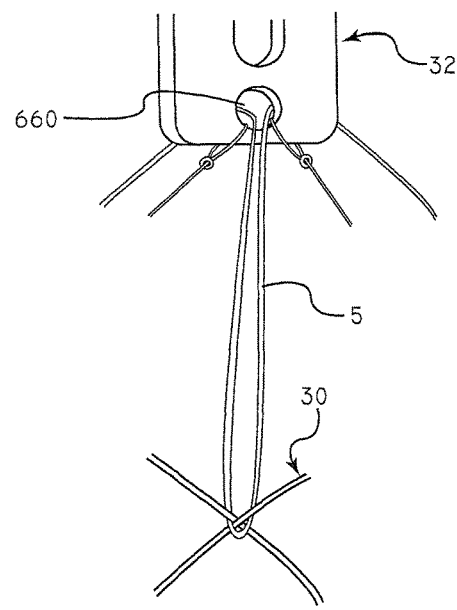
Figure 53C:
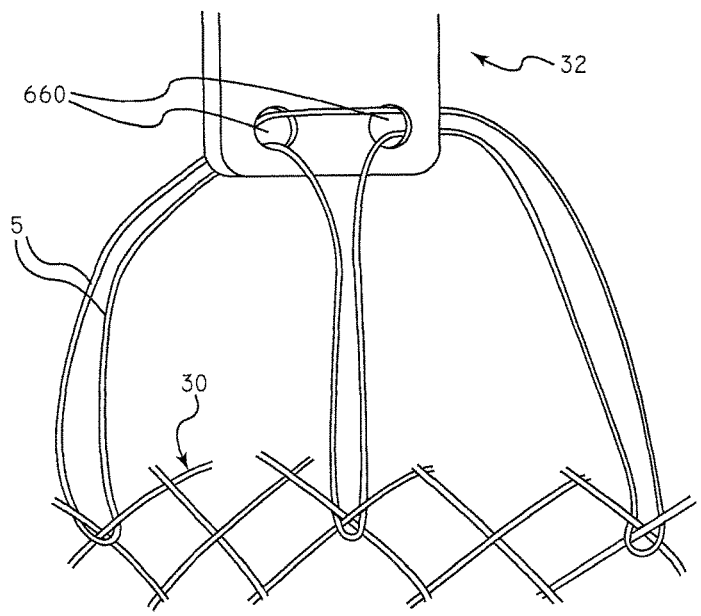

Referring now to FIG. 53, various ways to connect elements to the braid of anchor 30 of replacement valve apparatus 10 are described. In FIG. 53A, a post 32 having a single braid attachment hole 660 is attached to anchor 30 along three separate intersections of the braid via suture S. FIG. 53B provides a detail view of one exemplary technique for routing the suture between hole 660 and anchor 30. FIG. 53C illustrates a variation of the attachment, wherein post 32 comprises multiple braid attachment holes 660. As will be apparent, elements other than posts 32 may be attached to anchor 30 in the manner described, for example, anchor lock elements 34 may be attached in a similar manner.

While preferred embodiments of the present invention are shown and described herein, it will be obvious to those skilled in the art that such embodiments are provided by way of example only. Numerous variations, changes, and substitutions will occur to those skilled in the art without departing from the invention. For example, while the invention was described in connection with the replacement of a natural valve, the invention may also be used to replace an earlier-implanted prosthetic valve. Also, while the preceding discussion described the use of the invention to deliver and deploy replacement heart valves, it should be understood that the invention is not limited to that particular use. Other aspects of the invention include methods and apparatuses for endovascularly, percutaneously and/or endoscopically delivering and deploying expandable devices in a patient and optionally detaching a deployment tool from the device.

It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A replacement valve system, comprising:
   an outer delivery sheath;
   a shaft disposed within a lumen of the outer delivery sheath, the shaft having one or more lumens;
   a post attachment element coupled to the shaft;
   an anchor member including a post coupled to and disposed at a proximal end of the anchor member, the post having an opening within the post and is configured to engage with the post attachment element;
   wherein the post attachment element and the opening within the post have generally the same shape; and
   a plurality of leaflets are disposed within the anchor member.

2. The replacement valve system of claim 1, wherein a tube is disposed within the shaft lumen.

3. The replacement valve system of claim 2, wherein the post attachment element extends longitudinally through the tube.

4. The replacement valve system of claim 2, wherein at least a portion of the post extends through the tube when the opening within the post is engaged with the post attachment element.

5. The replacement valve system of claim 4, wherein proximal axial translation of the tube relative to the opening within the post when the opening within the post is engaged with the post attachment element, permits the opening within the post to disengage from the post attachment element.

6. The replacement valve system of claim 1, wherein a second post is coupled to and disposed at the proximal end of the anchor member, the second post having an opening within the second post and is configured to engage with a second post attachment element.

7. The replacement valve system of claim 1, wherein the post has a first position and a second position.

8. The replacement valve system of claim 1, wherein the anchor member has a radially repeating cell pattern.

9. The replacement valve system of claim 1, wherein the anchor has a first delivery position and a second deployment position.

10. The replacement valve system of claim 1, wherein the post attachment element and the opening within the post have a circular cross-section.

11. A replacement valve system, comprising:
    an outer delivery sheath;
    a shaft disposed within a lumen of the outer delivery sheath, the shaft having one or more lumens;
    a tube disposed with the shaft lumen;
    a post attachment element extending longitudinally within the tube;
    an anchor member including a post coupled to and disposed at a proximal end of the anchor member, the post having an opening within the post and is configured to engage with the post attachment element;
    wherein the post attachment element and the opening within the post have generally the same shape; and
    a plurality of leaflets are disposed within the anchor member.

12. The replacement valve system of claim 11, wherein at least a portion of the post extends through the tube when the opening within the post is engaged with the post attachment element.

13. The replacement valve system of claim 12, wherein proximal axial translation of the tube relative to the opening within the post when the opening within the post is engaged with the post attachment element, permits the opening within the post to disengage from the post attachment element.

14. The replacement valve system of claim 11, wherein the anchor has a first delivery position and a second deployment position.

15. The replacement valve system of claim 11, wherein the opening within the post and the post attachment element have a circular cross-section.

16. The replacement valve system of claim 11, wherein the anchor member has a radially repeating cell pattern.

17. A replacement valve system, comprising:
    an outer delivery sheath;
    a shaft disposed within a lumen of the outer delivery sheath, the shaft having one or more lumens;
    a tube disposed with the shaft lumen;
    a post attachment element extending longitudinally within the tube;
    an anchor member including a post coupled to and disposed at a proximal end of the anchor member, the post having an opening within the post and is configured to engage with the post attachment element;
    wherein the post attachment element and the opening within the post have generally the same shape;
    wherein at least a portion of the post extends through the tube when the opening within the post is engaged with the post attachment element; and
    a plurality of leaflets are disposed within the anchor member.

18. The replacement valve system of claim 17, wherein proximal axial translation of the tube relative to the opening within the post when the opening within the post is engaged with the post attachment element, permits the opening within the post to disengage from the post attachment element.

19. The replacement valve system of claim 17, wherein the anchor member has a radially repeating cell pattern.

20. The replacement valve system of claim 17, wherein the anchor member has a first delivery position and a second deployment position.

* * * * *